United States Patent [19]

Doherty et al.

[11] Patent Number: 5,024,994

[45] Date of Patent: Jun. 18, 1991

[54] RENIN INHIBITORS IV

[75] Inventors: Annette M. Doherty, Ann Arbor, Mich.; James P. Hudspeth, Newbury Park, Calif.; James S. Kaltenbronn, Ann Arbor; Joseph T. Repine, Ann Arbor, Mich.; William H. Roark, Ann Arbor, Mich.; Ila Sircar, Ann Arbor, Mich.; Francis J. Tinney, Ann Arbor, Mich.

[73] Assignee: Warner-Lambert Company, Morris Plains, N.J.

[21] Appl. No.: 233,320

[22] Filed: Aug. 17, 1988

Related U.S. Application Data

[63] Continuation-in-part of Ser. No. 113,278, Nov. 12, 1987, abandoned, which is a continuation-in-part of Ser. No. 945,582, Dec. 23, 1986, abandoned.

[51] Int. Cl.$^5$ .......................... A61K 37/02; C07K 5/00
[52] U.S. Cl. ......................................... 514/18; 514/19; 530/330; 530/331; 544/86; 544/162; 548/561; 558/5; 560/28; 560/39; 564/28; 564/104; 564/108; 564/153
[58] Field of Search .............................. 514/17, 18, 19; 530/330, 331, 332; 544/86, 162; 548/561; 558/5; 560/28, 39; 564/28, 104, 108, 153

[56] References Cited

U.S. PATENT DOCUMENTS 4,609,641  9/1986  Evans et al. ........................... 514/17

FOREIGN PATENT DOCUMENTS 0186977  5/1986  European Pat. Off. .............. 514/18

OTHER PUBLICATIONS

Haber et al., *J. Cardiovasc. Pharmacol.*, 1987, 10(Suppl. 7):554–558.
Burger, *Medicinal Chemistry*, 1960, pp. 565–571, 578–581, 600–601.
Denkewalter et al., *Progress in Drug Research*, vol. 10, 1966, pp. 510–512.
Plattner et al., *J. Med. Chem.*, 31(12), 1988, pp. 2277–2288.

*Primary Examiner*—Lester L. Lee
*Assistant Examiner*—Stephen B. Maebius
*Attorney, Agent, or Firm*—Elizabeth M. Anderson

[57] ABSTRACT

The invention concerns novel renin-inhibitory peptides which are useful for treating renin-assocated hypertension, hyperaldosteronism, and congestive heart failure. Processes for preparing the peptides, compositions containing them and methods of using them are included. Also included is a diagnostic method which uses the compounds to determine the presence of renin-associated hypertension or hyperaldosteronism.

6 Claims, No Drawings

RENIN INHIBITORS IV

CROSS-REFERENCE

This application is a continuation-in-part of application Ser. No. 113,278 filed Nov. 2, 1987, now abandoned, which is a continuation-in-part of application Ser. No. 945,582 filed Dec. 23, 1986, abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

The present invention concerns novel peptides which inhibit renin. It also concerns pharmaceutical compositions containing these novel peptides, methods of treating renin-associated hypertension, congestive heart failure, and hyperaldosteronism, as well as the use of the peptides as diagnostic tools, and the methods for preparing the peptides.

U.S. Pat. No. 4,479,941 covers certain renin-inhibitory peptides of the formula

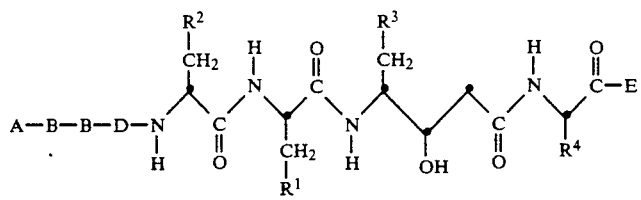

European Application No. 85/308759 covers certain renin-inhibitory dipeptides of the formula

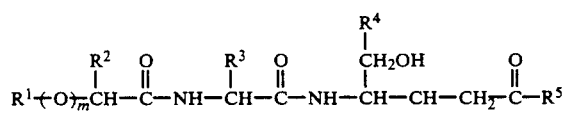

wherein m is 0 or 1 and $R^1-R^5$ are a variety of organic groups.

European Application No. 184,855 covers renin-inhibitory peptides of the formula

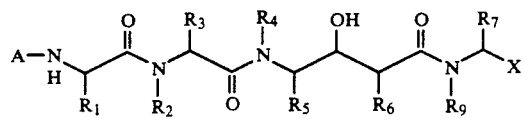

wherein A is an N-protecting group; $R_1$, $R_3$, $R_5$ and $R_7$ are lower alkyl or lipophilic or aromatic amino acid side chains and may be the same or different; $R_2$, $R_4$ and $R_6$ are hydrogen or lower alkyl and may be the same or different; X is hydrogen, lower alkyl or $-CH_2-OR_8$, wherein $R_8$ is hydrogen, lower alkyl or alkaryl; and $R_9$ is lower alkyl, hydroxy, hydroxyalkyl, alkoxy, allyl, alkaryloxy or thioalkyl and pharmaceutically acceptable salts thereof.

SUMMARY OF THE INVENTION

The present invention relates to novel peptides of the formula $$ACYL-X-Y-W-U-V \qquad (I)$$

and the pharmaceutically acceptable acid addition salts thereof wherein ACYL, X, Y, W, U, and V are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

The invention also includes a pharmaceutical composition comprising an effective amount of a peptide of formula I above in admixture with a pharmaceutically acceptable carrier or excipient, and a method for treating congestive heart failure in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above.

DETAILED DESCRIPTION

The following table provides a dictionary of the terms used in the description of the invention.

TABLE I

| Abbreviated Designation | Amino Acid |
|---|---|
| LEU | L-Leucine |
| D-LEU | D-Leucine |
| STA | 4(S)-Amino-3(S)-hydroxy-6-methylheptanoic acid |
| PHSTA | 4(S)-Amino-3(S)-hydroxy-5-phenylpentanoic acid |
| CYSTA | 4(S)-Amino-3(S)-hydroxy-5-cyclohexanepentanoic acid |
| ASTA | 3(RS), 4(S)-Diamino-6-methylheptanoic acid |
| ACYS | 3(RS), 4(S)-Diamino-5-cyclohexanepentanoic acid |
| CHSTA | 4(S)-Amino-3(S)-hydroxy-4-cyclohexanebutanoic acid |

TABLE I-continued

| Abbreviated Designation | |
|---|---|
| DFKSTA | 4(S)-Amino-3-oxo-2,2-difluoro-6-methylheptanoic acid |
| DFSTA | 4(S)-Amino-3(S)-hydroxy-2,2-difluoro-6-methylheptanoic acid |
| DFKCYS | 4(S)-Amino-3-oxo-2,2-difluoro-5-cyclohexanepentanoic acid |
| DFCYS | 4(S)-Amino-3(S)-hydroxy-2,2-difluoro-5-cyclohexanepentanoic acid |
| DFKCHS | 4(S)-Amino-3-oxo-2,2-difluoro-4-cyclohexanebutanoic acid |
| DFCHS | 4(S)-Amino-3(S)-hydroxy-2,2-difluoro-4-cyclohexanebutanoic acid |
| ILE | L-Isoleucine |
| D-ILE | D-Isoleucine |
| N-MeLEU | N-Methylleucine |
| N-MeILE | N-Methylisoleucine |
| PHE | L-Phenylalanine |
| HOMOPHE | Homophenylalanine |
| NLE | Norleucine |
| VAL | L-Valine |
| ORN | L-Ornithine |
| ARG(NO$_2$) | L-Nitroarginine |
| LYS | L-Lysine |
| NAPHTHYLALA | Naphthylalanine |
| CYCLOHEXYLALA | Cyclohexylalanine |
| TYR | L-Tyrosine |
| TRP | L-Tryptophane |
| ASN | L-Asparagine |
| O-MeTYR | O-Methyltyrosine |
| | Acyl Group |
| TOS | p-Toluenesulfonyl |
| PHT | Phthaloyl |
| Z | Benzyloxycarbonyl |
| BOC | Tert-butyloxycarbonyl |
| DNMA | Di-(1-naphthylmethyl)acetyl |
| DNMA-Cl | Di-(1-naphthylmethyl)acetyl chloride |
| BBSP | 2-Benzyl-3-(t-butylsulfonyl)propionyl |
| BMA | 3-Amino-3-methylbutanoyl |
| Z-BMA | 3-(Benzyloxycarbonylamino)-3-methylbutanoyl |
| MNPP | 2-(1-Naphthylmethyl)-3-phenyl-propionyl |
| IVA | Isovaleryl |
| NVA | n-Valeryl |
| | Amides With |
| —NHCH$_2$Ph | Benzylamine |
| —NHCH$_2$-(cyclohexyl) | Cyclohexylmethylamine |
| —NHCH$_2$-(C$_6$H$_4$)-CH$_2$NHZ (BOC) | m-Xylene-di-amine (Z or BOC) |
| —NHCH$_2$-(C$_6$H$_4$)-CH$_2$NH$_2$ | m-Xylene-di-amine |
| —NH$_2$ | Ammonia |
| —NH-(piperidine)-N—CH$_2$Ph | 4-Amino-N-benzyl-piperidine |
| —NH-(piperidine)-NH | 4-Aminopiperidine |
| —NH—CH$_2$-(2-pyridyl) | 2-Aminomethylpyridine |
| —NHCH$_2$CH(CH$_3$)CH$_2$CH$_3$ | 2-Methylbutylamine |
| —NH—CH(CH$_2$OH)—CH(CH$_3$)CH$_2$CH$_3$ | 1-Hydroxymethyl-2-methylbutylamine |
| —NHCH$_2$CH$_2$N(morpholine)O | 4-(2-Aminoethyl)morpholine |
| | Esters With |
| —OCH$_3$ | Methanol |
| —OC$_2$H$_5$ | Ethanol |
| O-t-Bu | t-Butanol |
| O-i-Pr | Isopropanol |
| | Solvents and Reagents |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| Et$_3$N | Triethylamine |
| THF | Tetrahydrofuran |
| EtOH | Ethanol |
| NaOEt | Sodium Ethoxide |
| NaOAc | Sodium Acetate |
| TFA | Trifluoroacetic acid |
| DMAP | 4-Dimethylaminopyridine |

The peptides of the present invention are represented by the formula $$ACYL-X-Y-W-U-V \qquad I$$

or a pharmaceutically acceptable salt thereof, wherein ACYL is BOC, IVA, NVA, DNMA, Z, MNPP, BMA, BBSP, or (naphthyl)-CH$_2$-CH(CO—)-CH$_2$-D(=O)

wherein D is

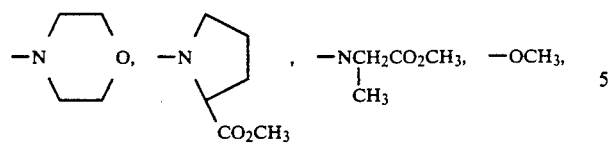
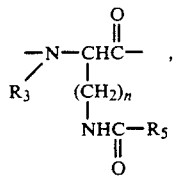
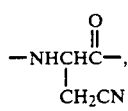
X is absent, PHE, HOMOPHE, NAPHTHYLALA, CYCLOHEXYLALA, O-MeTYR, TYR, or TRP, with the proviso that when ACYL is DNMA, BBSP, MNPP, or
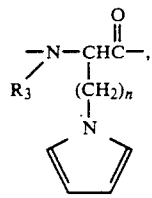
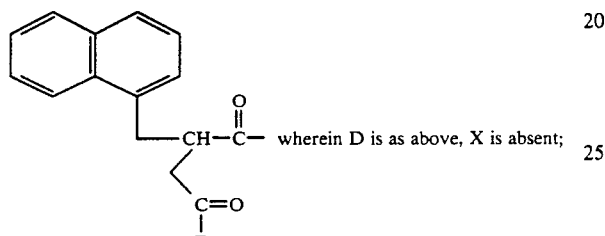 wherein D is as above, X is absent;
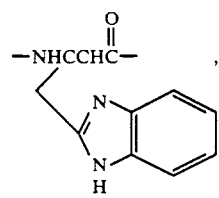
Y is
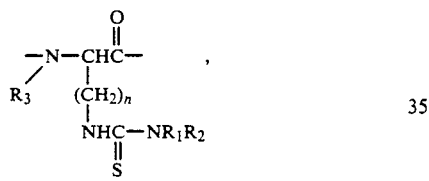
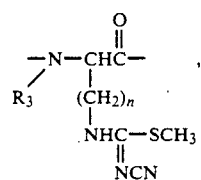
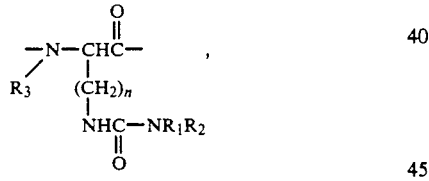
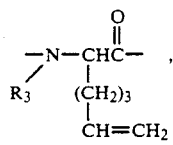
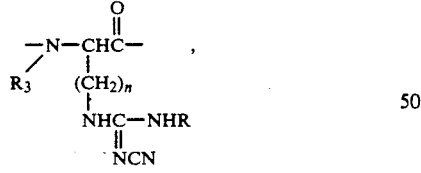
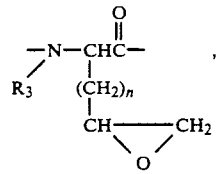
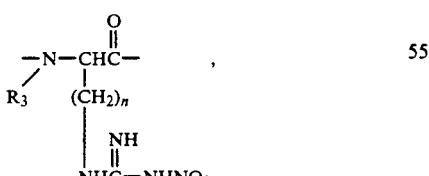
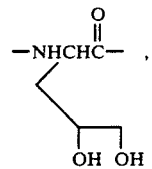
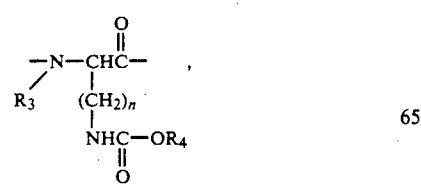
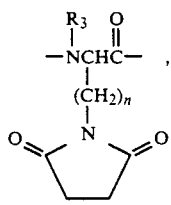

-continued
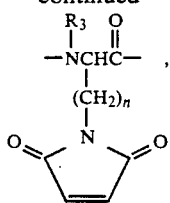
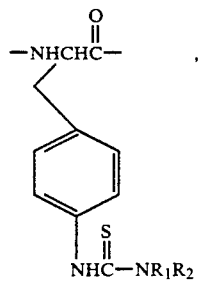
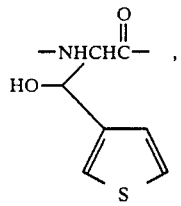
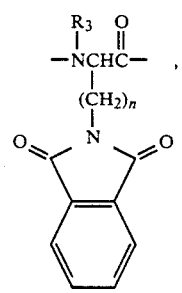
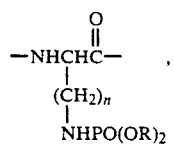
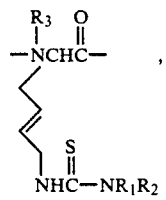
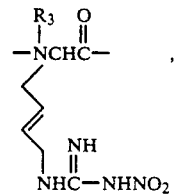
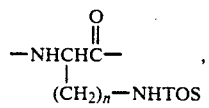
-continued
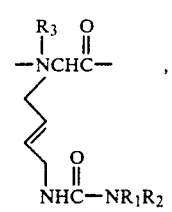
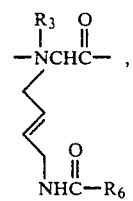
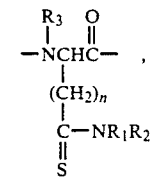
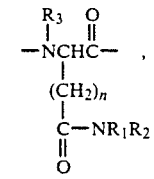
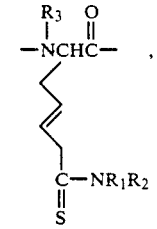
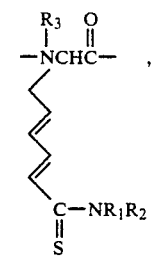
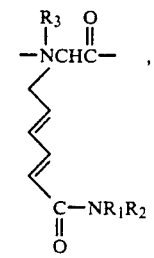

-continued
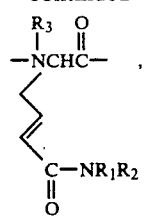
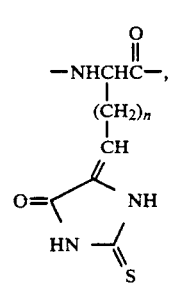
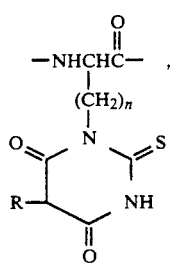
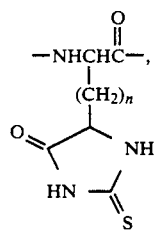
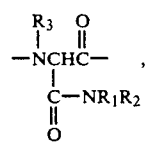
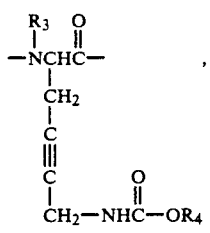
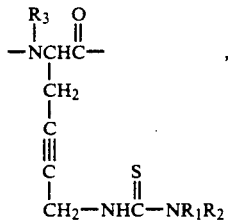
-continued
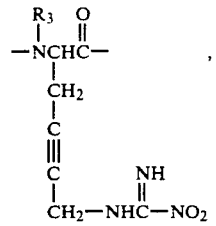
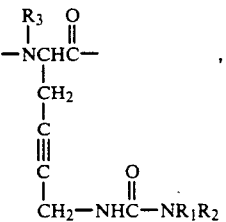
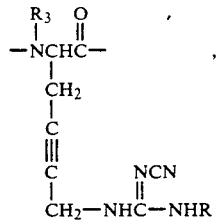
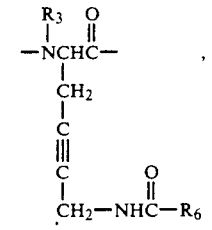
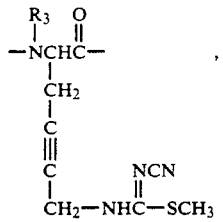
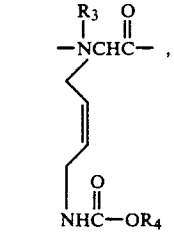
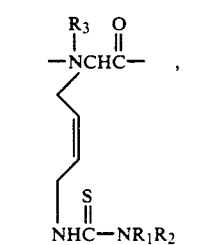

-continued

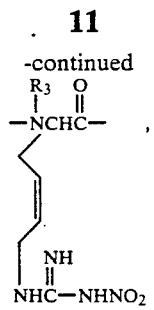

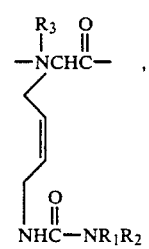

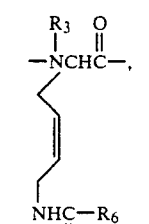

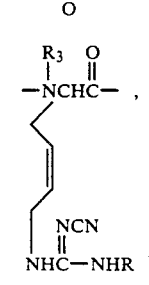

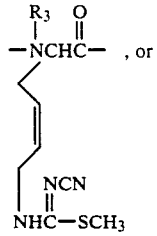

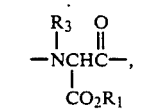

wherein n is an integer from 2 to 8, R is hydrogen or an alkyl of from 1 to 3 carbon atoms, $R_1$ and $R_2$ are each independently hydrogen, lower alkyl of from 1 to 4 carbon atoms, or taken together form a 5 or 6 membered ring with the nitrogen to which they are attached, aralkyl, or aryl, $R_3$ is hydrogen or methyl, $R_4$ is lower alkyl or benzyl, $R_5$ is $CH_2SCH_3$, $CH_2SOCH_3$, or $CH_2SO_2CH_3$, $R_6$ is $R_5$, H, or lower alkyl;

W is STA, PHSTA, CYSTA, ASTA, ACYS, CHSTA, DFSTA, DFKSTA, DFCYS, DFKCYS, DFCHS, or DFKCHS;

U is absent, LEU, ILE, VAL, N-MeLEU, N-MeILE; and

V is

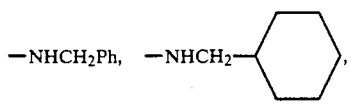

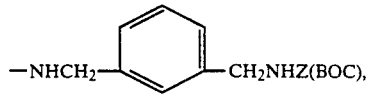

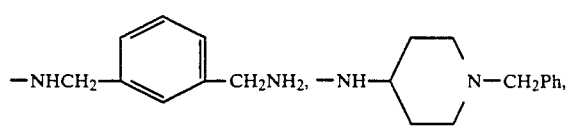

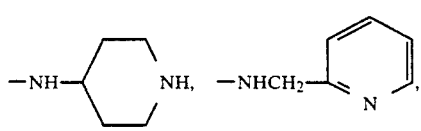

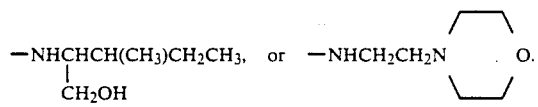

Preferred compounds of the present invention are represented by formula I wherein ACYL is BOC, IVA, DNMA, BMA, BBSP, or

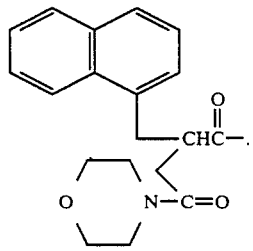

Other preferred compounds are according to formula I wherein

V is 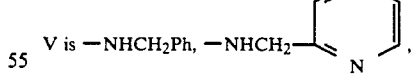

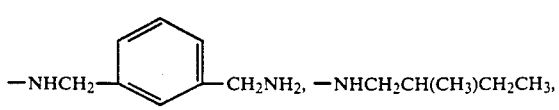

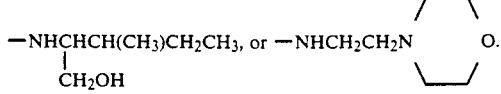

Particularly valuable compounds falling within the scope of the invention include the following:

BOC—PHE—ORN(PHT)—STA—LEU—NHCH₂Ph,

IVA—PHE—NHCHC(=O)—STA—NHCH₂CH(CH₃)CH₂CH₃,
              |
              CH₂CN

BOC—PHE—ARG(NO₂)—STA—LEU—NHCH₂Ph,

DNMA—ORN(C(=S)—NHCH₃)—STA—NHCH₂CH(CH₃)CH₂CH₃,

DNMA—ORN(C(=O)—NHCH₃)—STA—NHCH₂CH(CH₃)CH₂CH₃,

DNMA—NHCHC(=O)—STA—NHCH₂CH(CH₃)CH₂CH₃,
       |
       CH₂-(2-benzimidazolyl)

DNMA—NHCHC(=O)—STA—NHCH₂CH(CH₃)CH₂CH₃,
       |
       CH₂CH(OH)—CH₂OH

DNMA—LYS(C(=S)—NHCH₃)—STA—NHCH₂CH(CH₃)CH₂CH₃,

DNMA—LYS(C(=O)—NHCH₃)—STA—NHCH₂CH(CH₃)CH₂CH₃,

DNMA—LYS(C(=O)—NH₂)—STA—NHCH₂CH(CH₃)CH₂CH₃,

DNMA—NHCHC(=O)—STA—NHCH₂CH(CH₃)CH₂CH₃,
       |
       CO₂CH₃

DNMA—LYS(C(=S)—NH(CH₂)₃CH₃)—STA—NHCH₂CH(CH₃)CH₂CH₃,

DNMA—LYS(C(=S)—NHPh)—STA—NHCH₂CH(CH₃)CH₂CH₃,

DNMA—LYS(C(=S)—NHC(CH₃)₂CH₂CH₃)—STA—NHCH₂CH(CH₃)CH₂CH₃,

DNMA—LYS(C(=S)—NHCH₃)—CYSTA—NHCH₂CH(CH₃)CH₂CH₃,

DNMA—LYS(C(=NH)—NHNO₂)—CYSTA—NHCH₂CH(CH₃)CH₂CH₃,

DNMA—LYS(P(=O)—(OPh)₂)—STA—NHCH₂CH(CH₃)CH₂CH₃,

DNMA—LYS(C(=NCN)—SCH₃)—STA—NHCH₂CH(CH₃)CH₂CH₃,

DNMA—LYS(C(=NCN)—NH₂)—STA—NHCH₂CH(CH₃)CH₂CH₃,

DNMA—LYS(C(=NCN)—NHCH₃)—STA—NHCH₂CH(CH₃)CH₂CH₃,

DNMA—NHCH(CO)—STA—NHCH₂CH(CH₃)CH₂CH₃,
           |
         (CH₂)₄—N⟨pyrrole⟩

DNMA—NHCH(CO)—STA—NHCH₂CH(CH₃)CH₂CH₃,
           |
         (CH₂)₃—N⟨pyrrole⟩

DNMA—LYS(Z)—STA—LEU—NHCH₂Ph,

DNMA—LYS(C(=NH)—NHNO₂)—STA—LEU—NHCH₂Ph,

DNMA—LYS(C(=S)—NHCH₃)—STA—LEU—NHCH₂Ph,

DNMA—LYS(C(=O)—NHCH₃)—STA—LEU—NHCH₂Ph,

DNMA—NHCH(CO)—STA—NHCH₂CH(CH₃)CH₂CH₃,
           |
         (CH₂)₅—NHZ

DNMA—NHCH(CO)—STA—NHCH₂CH(CH₃)CH₂CH₃,
           |
         (CH₂)₅—NHC(=S)—NHCH₃

DNMA—NHCH(CO)—STA—NHCH₂CH(CH₃)CH₂CH₃,
           |
         (CH₂)₅—NHC(=NH)—NHNO₂

DNMA—NHCH(CO)—STA—LEU—NHCH₂Ph,
           |
         (CH₂)₅—NHC(=S)—NHCH₃

DNMA—NHCH(CO)—STA—LEU—NHCH₂Ph,
           |
         (CH₂)₅—NHC(=NH)—NHNO₂

DNMA—NHCH(CO)—STA—NHCH₂CH(CH₃)CH₂CH₃,
           |
         (CH₂)₆—NHZ

DNMA—NHCH(CO)—STA—NHCH₂CH(CH₃)CH₂CH₃,
           |
         (CH₂)₆—NHC(=S)—NHCH₃

DNMA—NHCH(CO)—STA—NHCH₂CH(CH₃)CH₂CH₃,
           |
         (CH₂)₆—NHC(=NCN)—NH₂

DNMA—NHCH(CO)—STA—LEU—NHCH₂Ph,
           |
         (CH₂)₆—NHZ

-continued

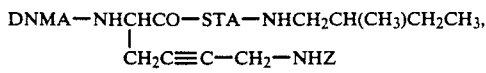
DNMA—NHCHCO—STA—NHCH₂CH(CH₃)CH₂CH₃,
            |
            CH₂C≡C—CH₂—NHZ

BOC—PHE—NHCHCO—STA—NHCH₂CH(CH₃)CH₂CH₃,
              |
              CO₂CH₃

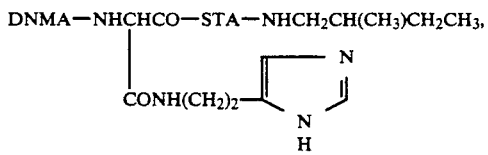
DNMA—NHCHCO—STA—NHCH₂CH(CH₃)CH₂CH₃,
       |
       CONH(CH₂)₂—[imidazole]

DNMA—NHCHCO—STA—NHCH₂CH(CH₃)CH₂CH₃,
       |
       CONH₂

DNMA—NHCHCO—STA—NHCH₂CH(CH₃)CH₂CH₃,
       |
       CONHCH₃

DNMA—NHCHCO—STA—NHCH₂CH(CH₃)CH₂CH₃,
       |
       CON(CH₃)₂

DNMA—LYS(TOS)—STA—NHCH₂CH(CH₃)CH₂CH₃,
DNMA—LYS(CO₂CH₃)—STA—NHCH₂CH(CH₃)CH₂CH₃,

BOC—PHE—NHCHCO—STA—NHCH₂CH(CH₃)CH₂CH₃,
              |
              CO₂C(CH₃)₃

DNMA—NHCHCO—STA—NHCH₂CH(CH₃)CH₂CH₃,
       |
       CO₂C₂H₅

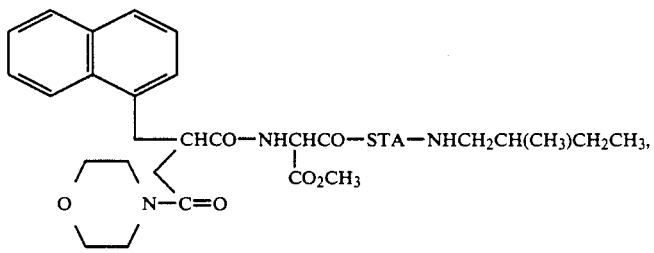

DNMA—NHCHCO—STA—NHCH₂CH(CH₃)CH₂CH₃,
       |
       (CH₂)₅—CONHCH₃

DNMA—NHCH[(CH₂)₃CH=CH₂]CO—STA—LEU—NHCH₂Ph (Isomer A),
DNMA—NHCH[(CH₂)₃CH=CH₂]CO—STA—LEU—NHCH₂Ph (Isomer B),

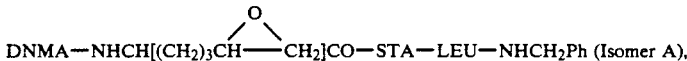
DNMA—NHCH[(CH₂)₃CH——CH₂]CO—STA—LEU—NHCH₂Ph (Isomer A),

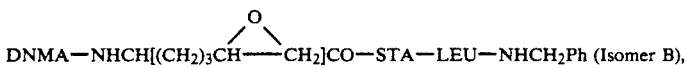
DNMA—NHCH[(CH₂)₃CH——CH₂]CO—STA—LEU—NHCH₂Ph (Isomer B),

DNMA—NHCHCO—STA—NHCH₂CH(CH₃)CH₂CH₃,
       |
       CO₂CH(CH₃)₂

DNMA—NHCHCO—STA—NHCH₂CH(CH₃)CH₂CH₃ (Isomer A),
       |
       CH₂C≡C—CH₂NHCOCH₃

DNMA—NHCHCO—STA—NHCH₂CH(CH₃)CH₂CH₃ (Isomer B),
       |
       CH₂C≡C—CH₂NHCOCH₃

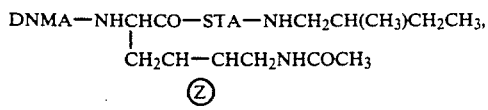
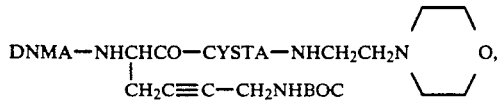
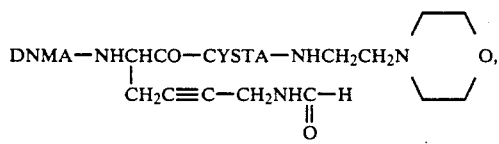
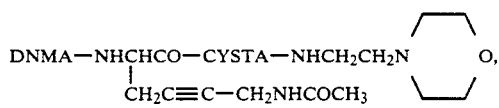
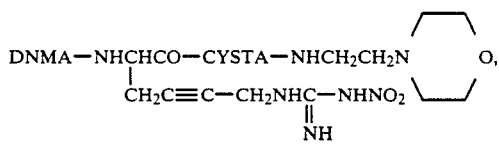
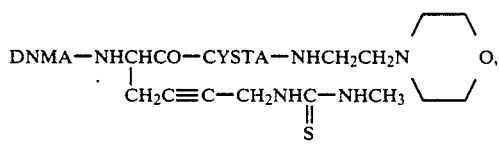
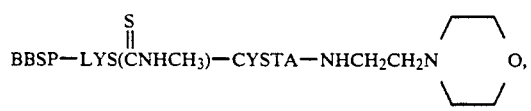
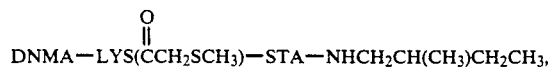
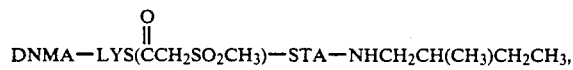
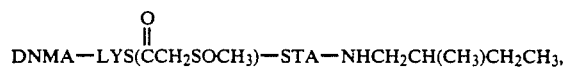
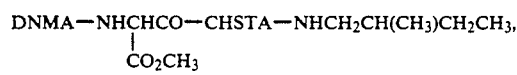
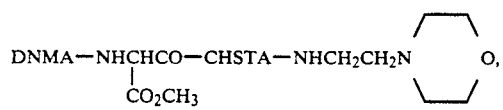

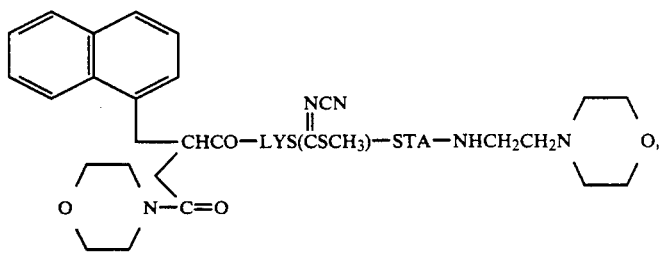
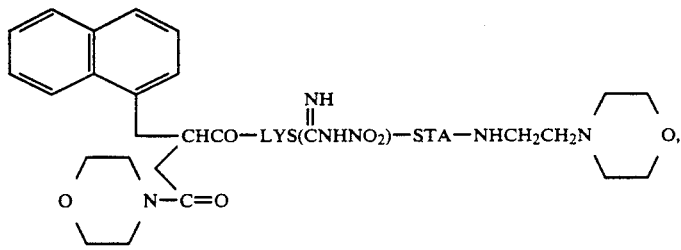
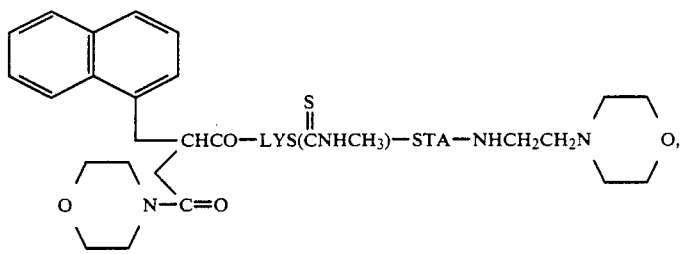
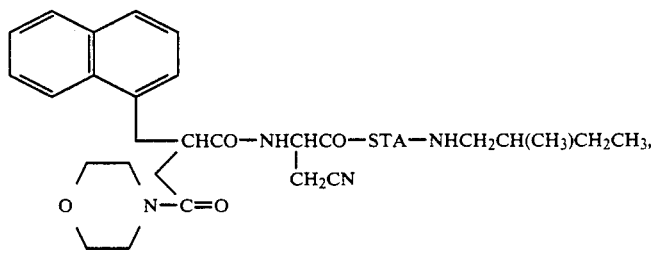
DNMA—NHCHCO—STA—NHCH₂CH(CH₃)CH₂CH₃,
       |
       CH₂CN
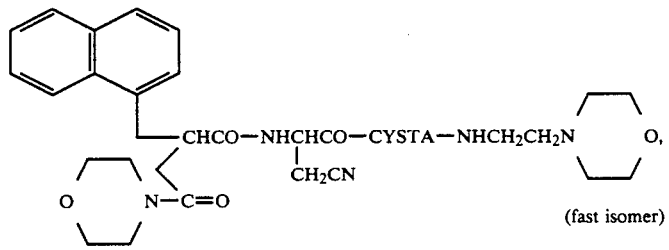
(fast isomer)
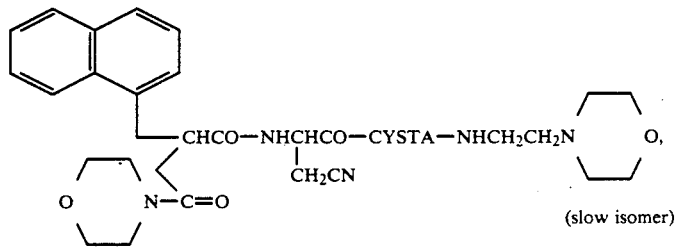
(slow isomer)

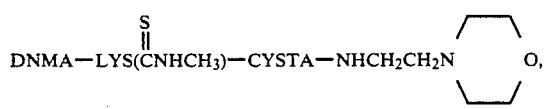
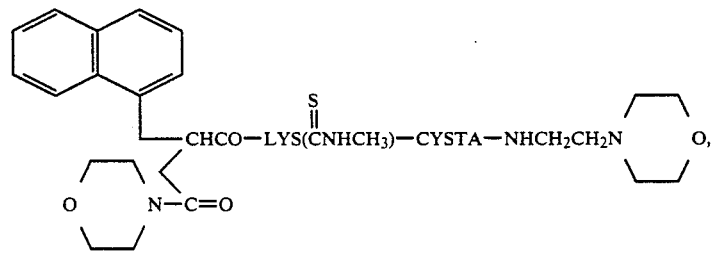
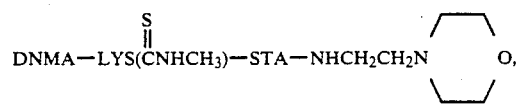
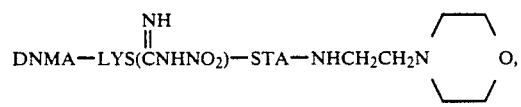
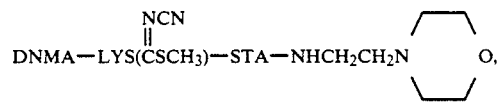
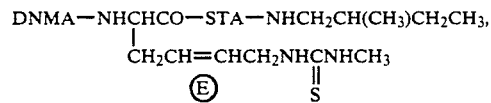
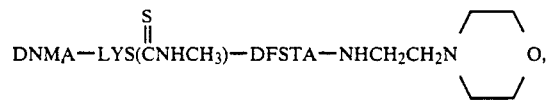
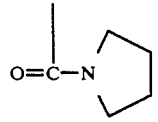
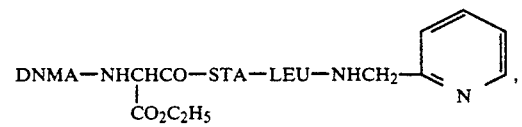
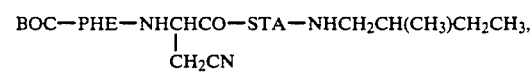
Other valuable compounds falling with the scope of the invention are:
DNMA—ORN(PHT)—STA—LEU—NHCH2Ph,
DNMA—ORN(PHT)—STA—NHCH2CH(CH3)CH2CH3, DNMA—NHCHC(=O)—STA—LEU—NHCH₂Ph,
      |
      CH₂CN DNMA—ARG(NO₂)—STA—LEU—NHCH₂Ph,
DNMA—ARG(NO₂)—STA—NHCH₂CH(CH₃)CH₂CH₃,
DNMA—ORN(C(=S)—NHCH₃)—STA—LEU—NHCH₂Ph, DNMA—ORN(C(=S)—NHCH₃)—STA—LEU—NHCH₂-2-pyridyl, DNMA—ORN(C(=O)—NHCH₃)—STA—LEU—NHCH₂Ph, DNMA—ARG(NO₂)—CYSTA—LEU—NHCH₂-2-pyridyl, BOC—PHE—ORN(C(=O)—NHCH₃)—STA—LEU—NHCH₂Ph,

BOC—PHE—ORN(C(=S)—NHCH₃)—STA—NHCH₂CH(CH₃)CH₂CH₃,

BOC—PHE—NHCHC(=O)—STA—NHCH₂CH(CH₃)CH₂CH₃,
        |
        CH₂-(1H-benzimidazol-2-yl)

DNMA—NHCHC(=O)—STA—LEU—NHCH₂Ph,
      |
      CH₂CH—CH₂
         |    |
         OH  OH

BOC—PHE—NHCHC(=O)—STA—NHCH₂CH(CH₃)CH₂CH₃,
        |
        CH₂CH—CH₂
           |    |
           OH  OH

DNMA—LYS(C(=S)—NHCH₃)—STA—LEU—NHCH₂-2-pyridyl,

BOC—PHE—LYS(C(=S)—NHCH₃)—STA—LEU—NHCH₂Ph,

BOC—PHE—LYS(C(=O)—NHCH₃)—STA—LEU—NHCH₂Ph,

DNMA—LYS(C(=O)—NH₂)—STA—LEU—NHCH₂Ph,

-continued

BOC—PHE—LYS(C—NH₂)—STA—LEU—NHCH₂Ph,
            ‖
            O

DNMA—LYS(C—N(CH₃)₂)—STA—LEU—NHCH₂Ph,
       ‖
       S

DNMA—LYS(C—N(CH₃)₂)—STA—NHCH₂CH(CH₃)CH₂CH₃,
       ‖
       S

```
              O
              ‖
DNMA—NHCHC—STA—LEU—NHCH₂Ph,
      |
      (CH₂)₆
      |
      NHC—NHCH₃
      ‖
      S
```

```
                  O
                  ‖
BOC—PHE—NHCH—C—STA—LEU—NHCH₂Ph,
          |
          (CH₂)₅
          |
          S
          ‖
          NHC—NHCH₃
```

```
              O
              ‖
DNMA—NHCHC—STA—NHCH₂CH(CH₃)CH₂CH₃,
      |
      CH₂
      |
      [C₆H₄]
      |
      S
      ‖
      NHC—N(CH₃)₂
```

DNMA—LYS(PO(OCH₃)₂)—STA—NHCH₂CH(CH₃)CH₂CH₃,

```
              O
              ‖
DNMA—NHCHC—STA—LEU—NHCH₂Ph,
      |
      CH₂CH=CHCH₂
      |
      S
      ‖
      NHC—NHCH₃
```

DNMA—LYS(C—NHNO₂)—STA—NHCH₂CH(CH₃)CH₂CH₃,
       ‖
       NH

BOC—PHE—LYS(C—NHNO₂)—STA—LEU—NHCH₂Ph,
            ‖
            NH

```
                  O
                  ‖
BOC—PHE—NHCHC—STA—LEU—NHCH₂Ph,
          |
          (CH₂)₅
          |
          NHC—NHNO₂
          ‖
          NH
```

```
              O
              ‖
DNMA—NHCHC—STA—NHCH₂CH(CH₃)CH₂CH₃,
      |
      (CH₂)₆
      |
      NHC—NHNO₂
      ‖
      NH
```

-continued
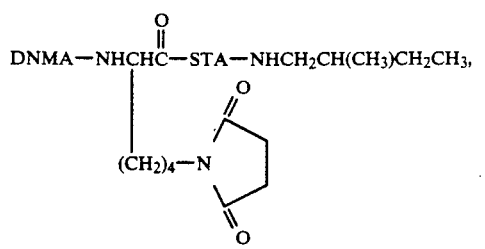
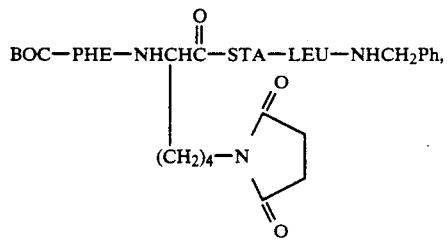
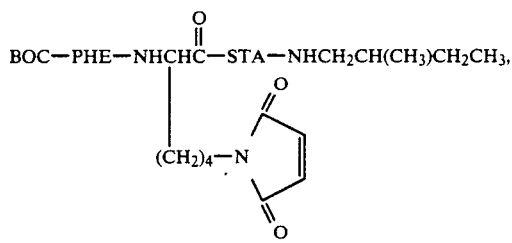
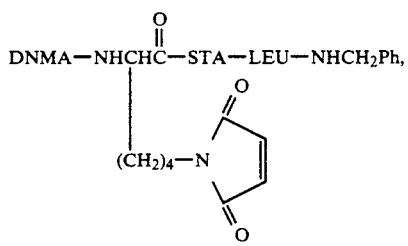
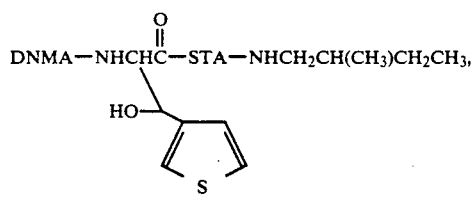
DNMA—LYS(TOS)—STA—LEU—NHCH₂Ph,
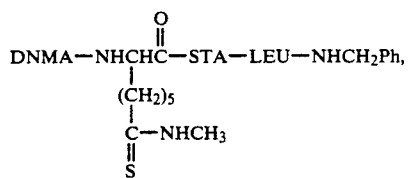
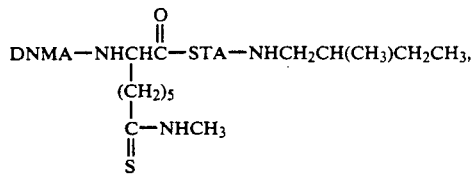

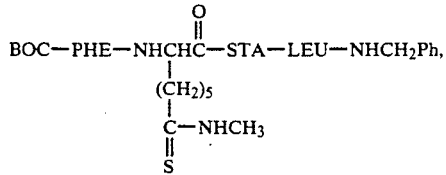
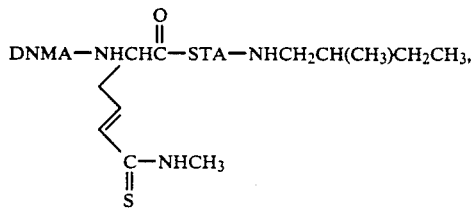
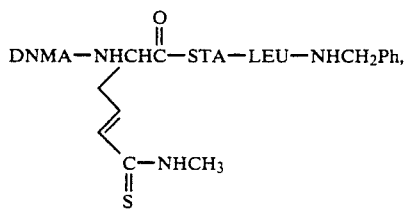
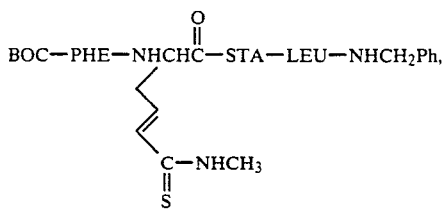
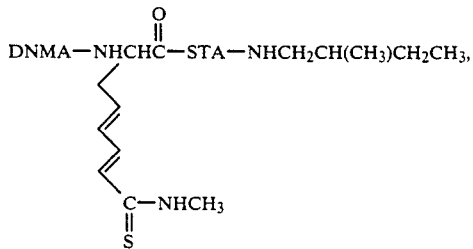
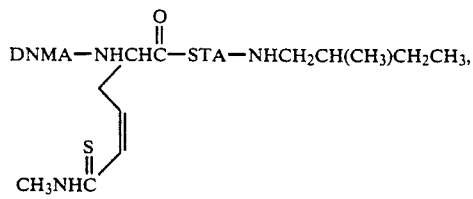
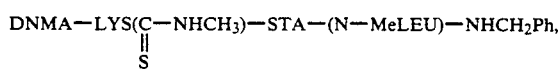
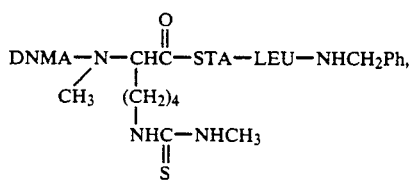
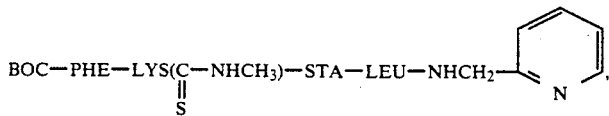

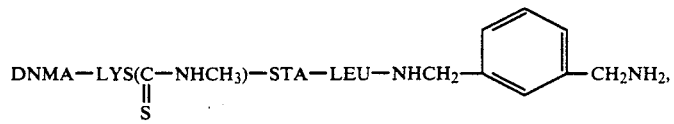
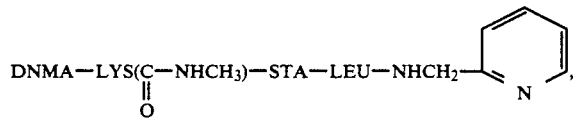
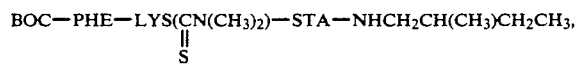
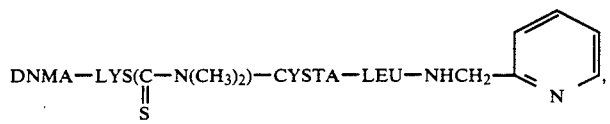
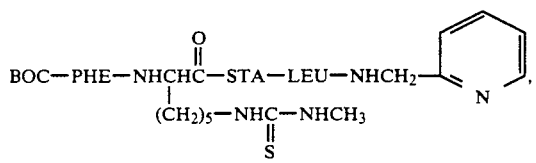
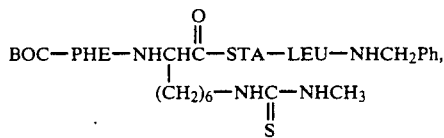
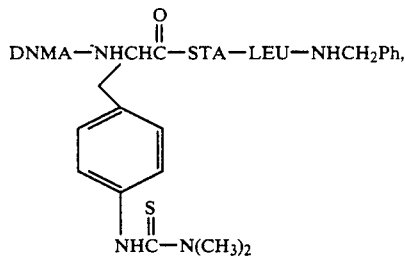
DNMA—LYS(PO(OCH₃)₂)—STA—LEU—NHCH₂Ph,
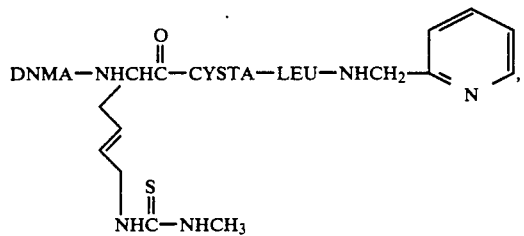
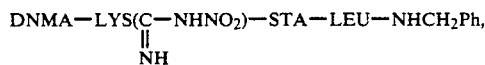
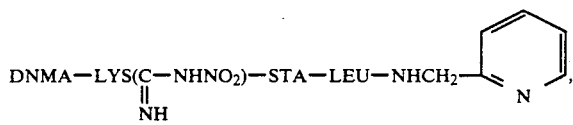

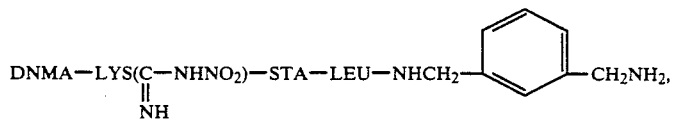
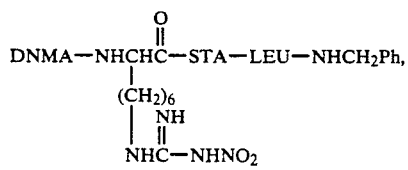
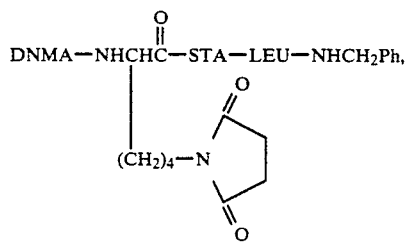
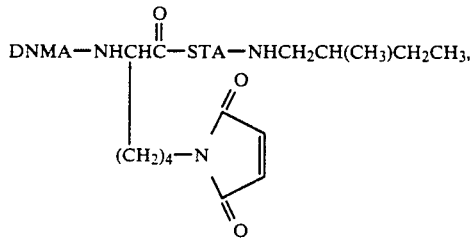
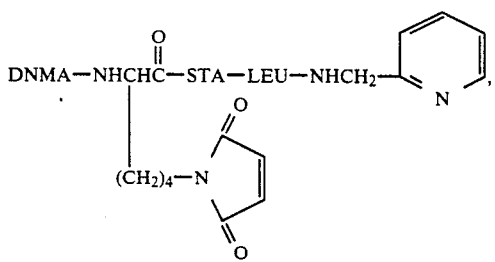
DNMA—LYS(TOS)—STA—ILE—NHCH₂Ph,
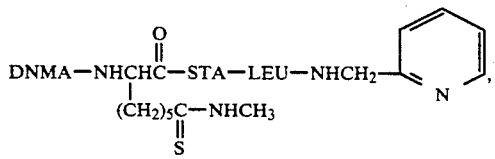
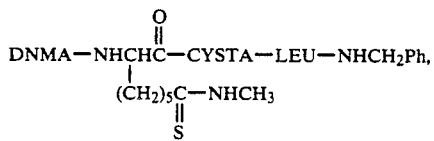
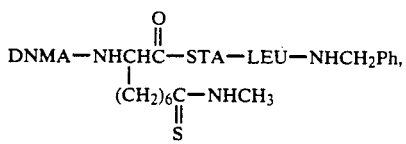

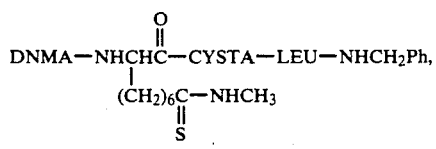
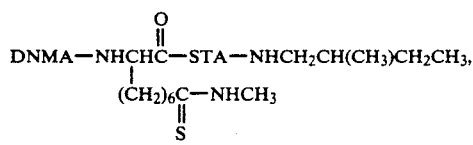
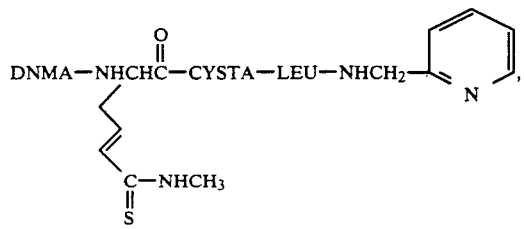
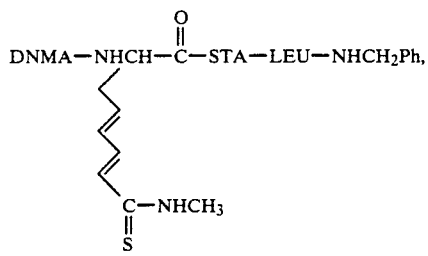
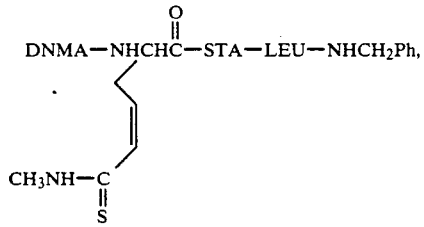
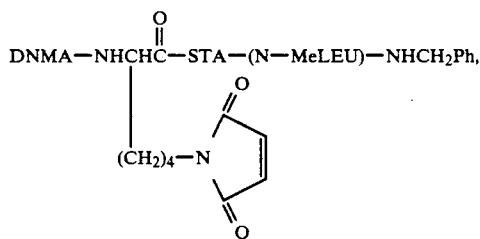
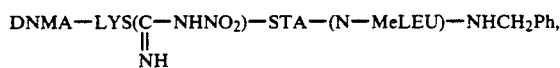
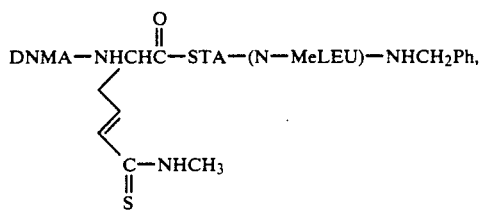

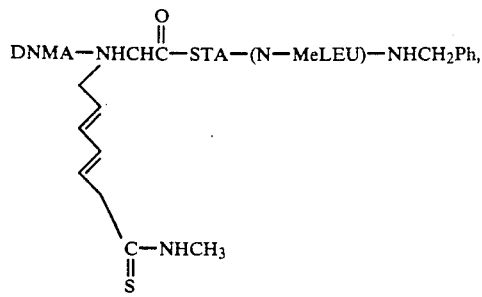
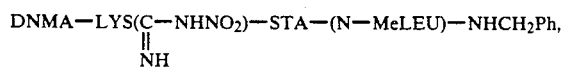
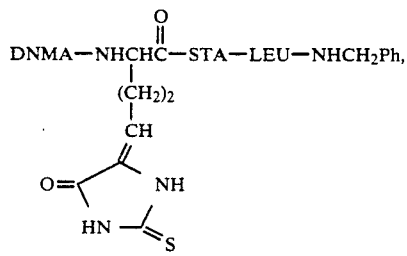
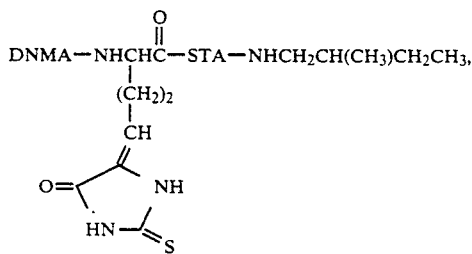
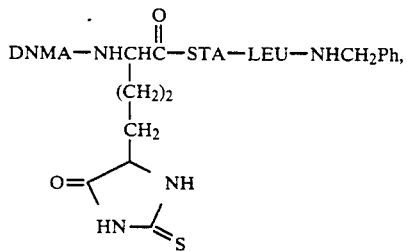
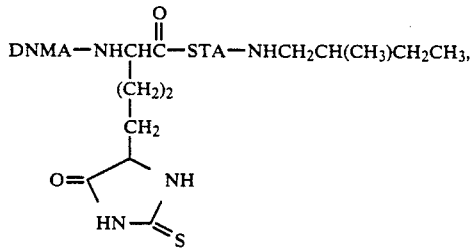
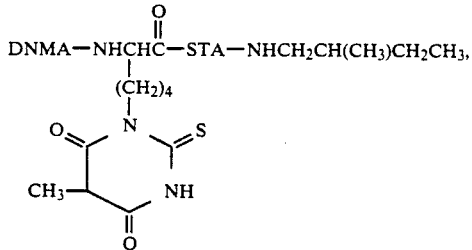

-continued
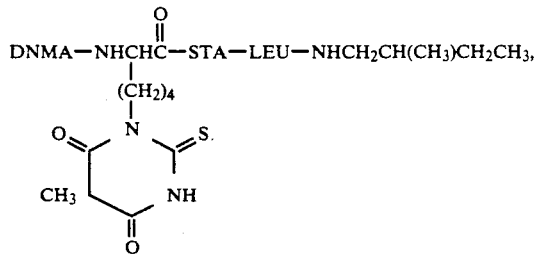
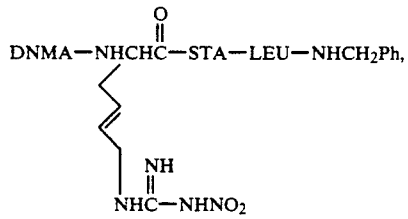
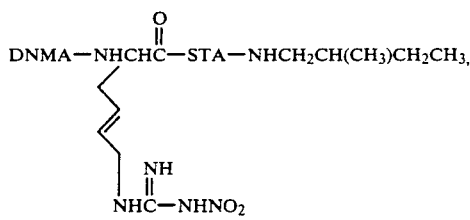
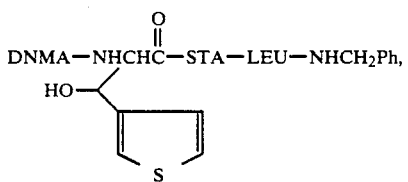
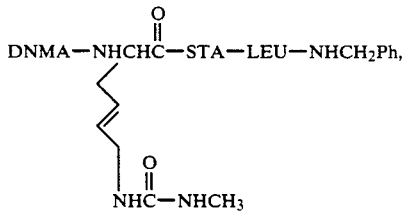
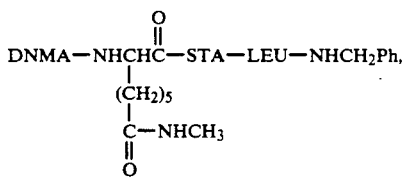
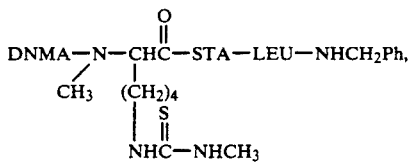
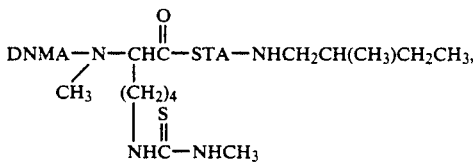

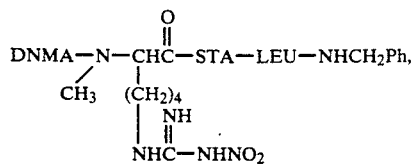
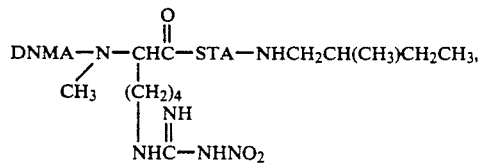
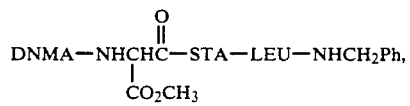
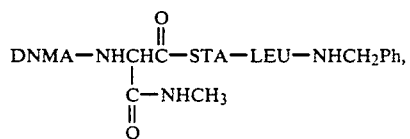
DNMA—ARG(NO₂)—STA—(D-LEU)—NHCH₂Ph,
DNMA—ARG(NO₂)—STA—(D-ILE)—NHCH₂Ph,
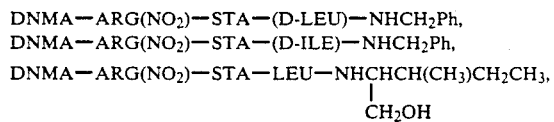
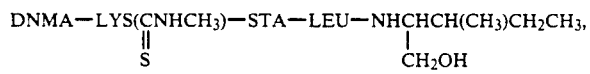
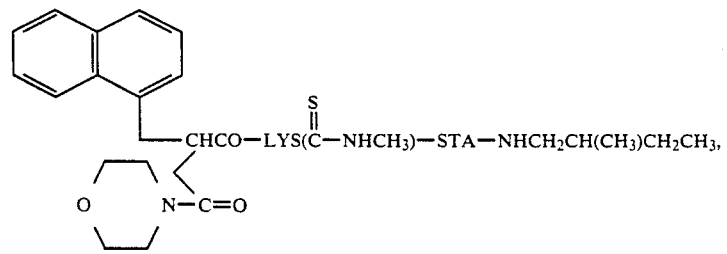
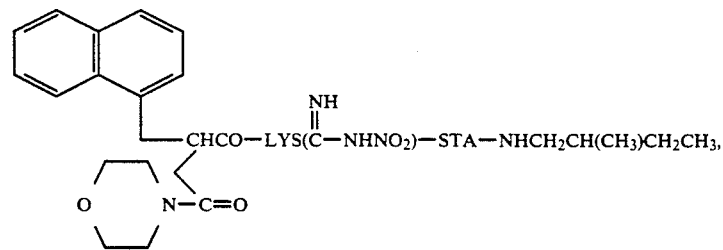
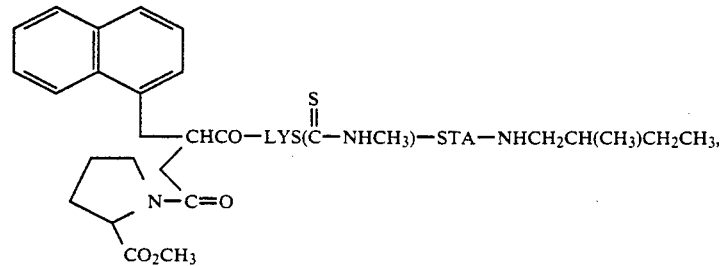

-continued
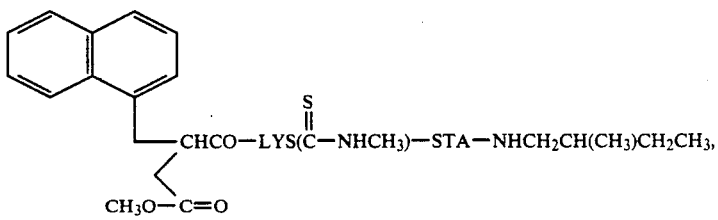
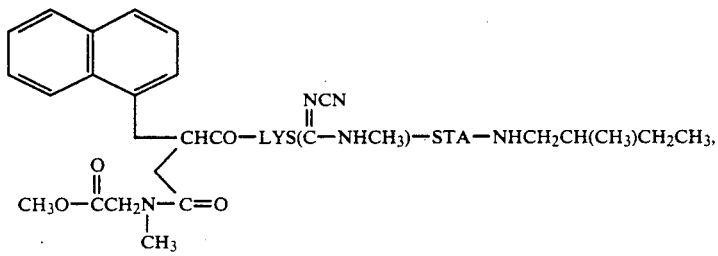
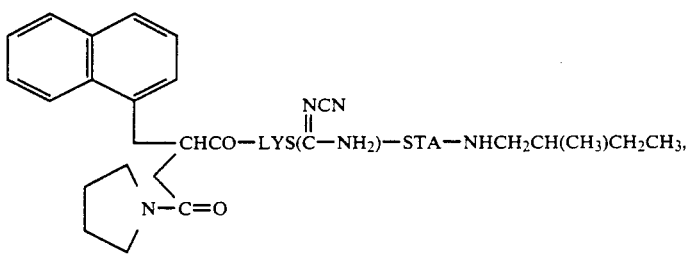
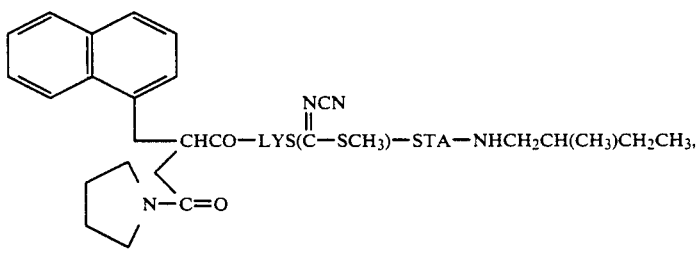
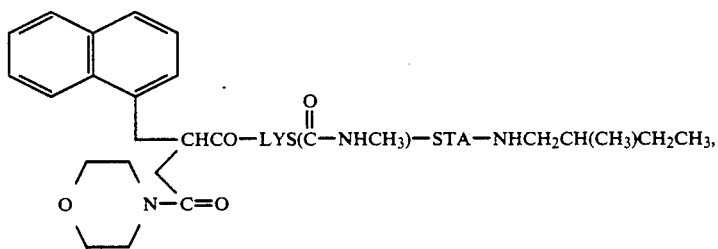
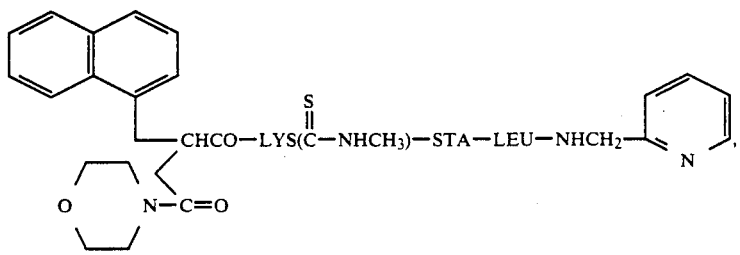

-continued
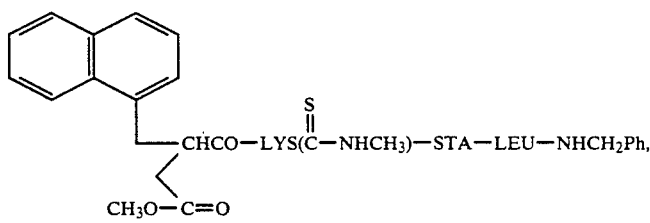
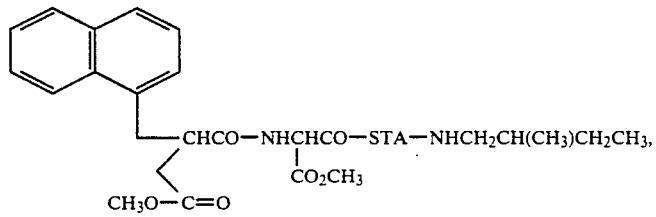
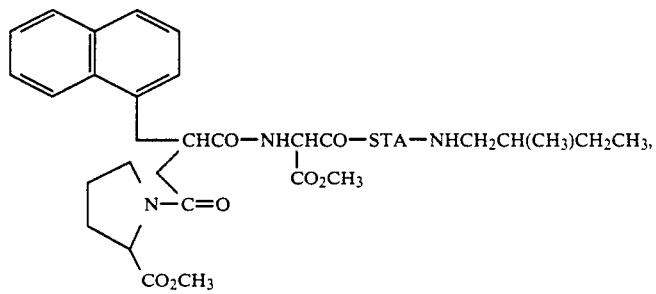
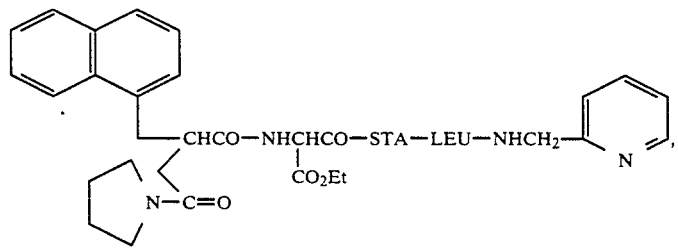
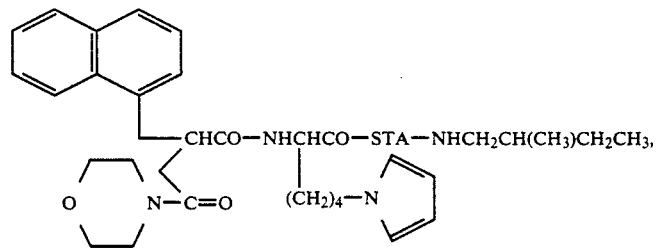
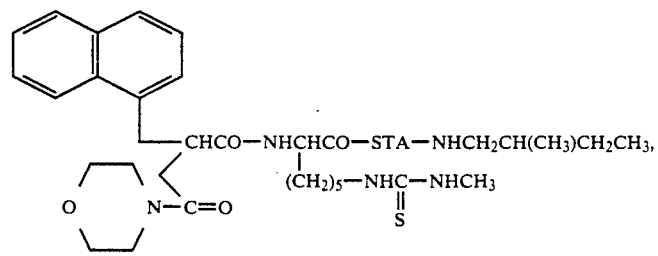

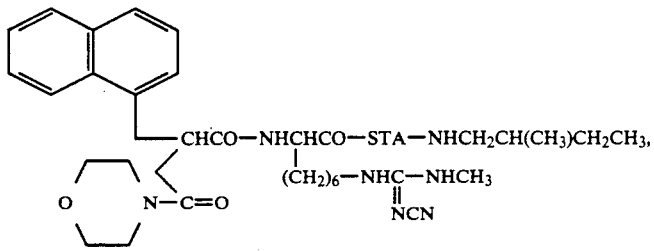
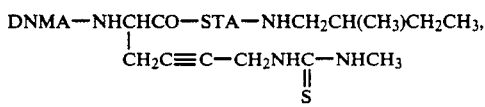
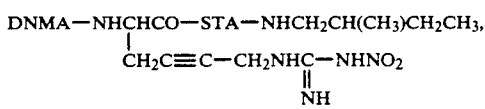
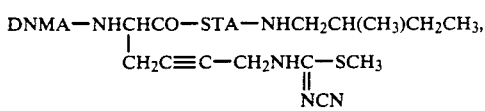
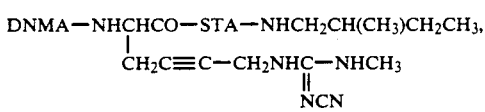
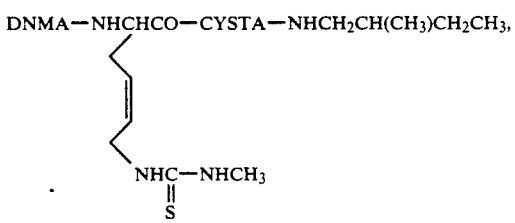
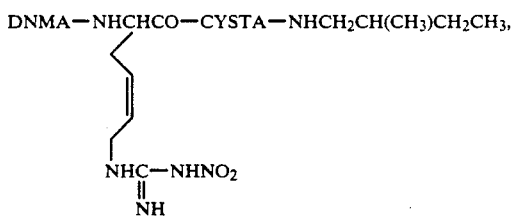
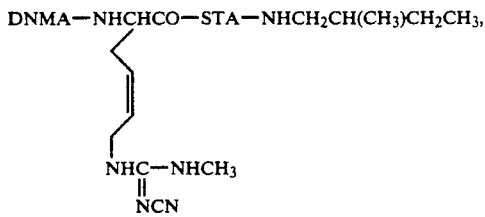
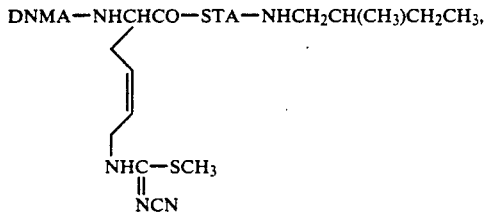

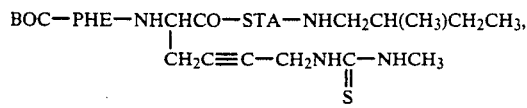
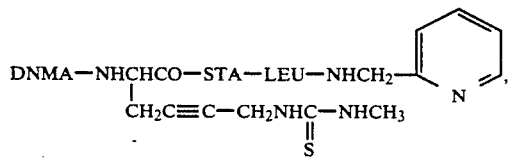
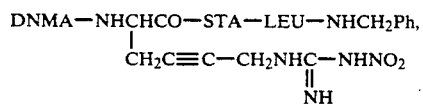
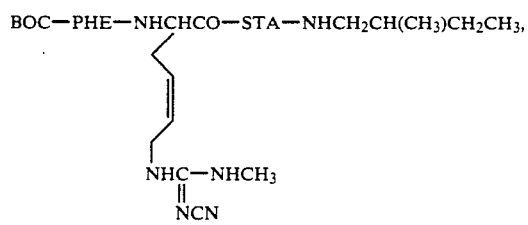
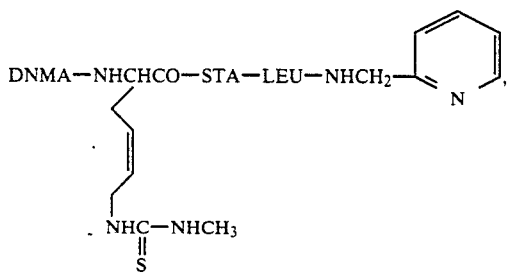
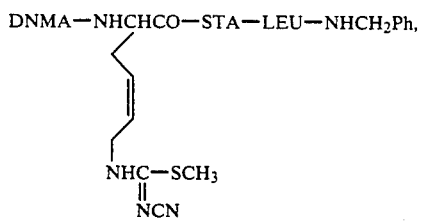
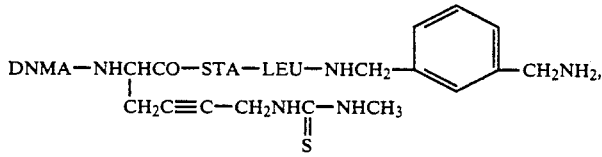
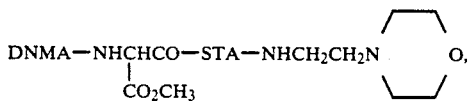
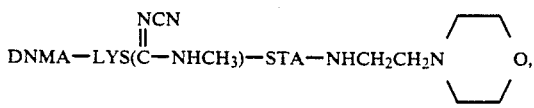

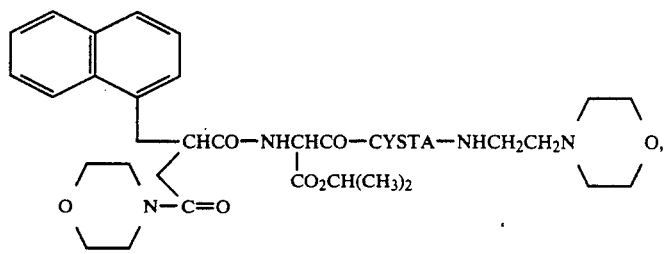
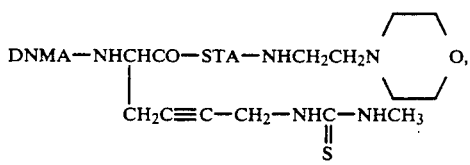
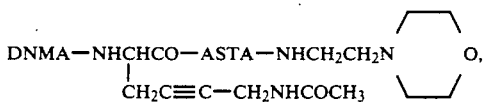
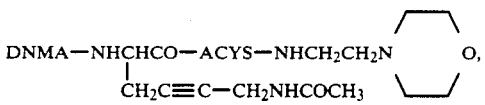
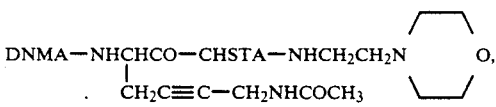
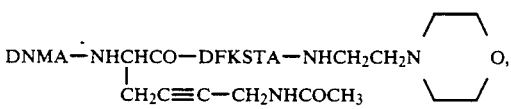
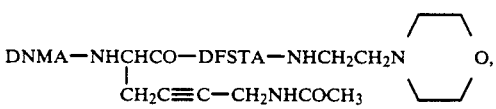
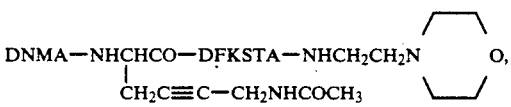
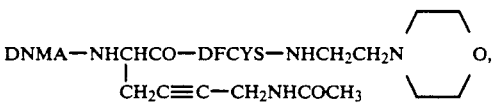
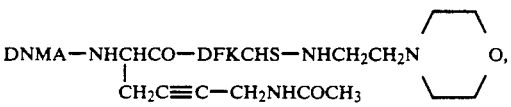
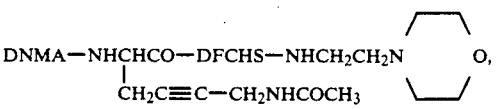

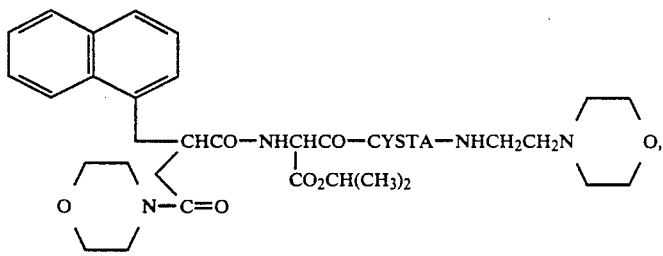
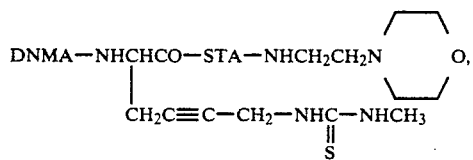
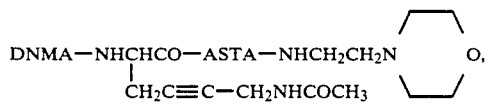
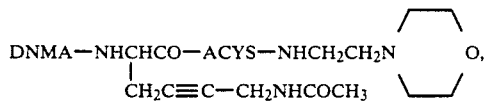
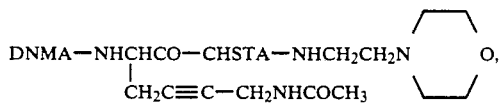
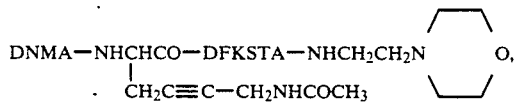
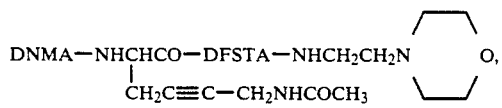
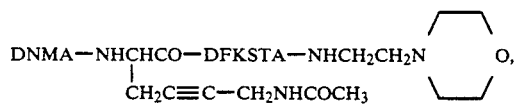
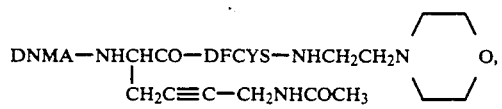
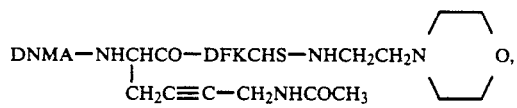
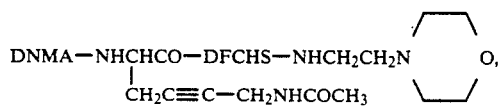
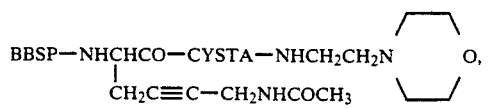

-continued
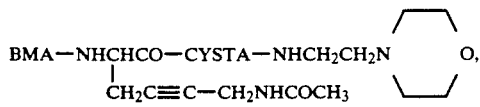
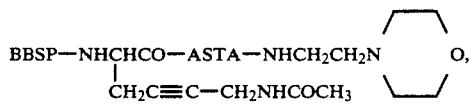
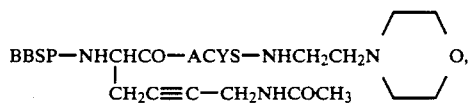
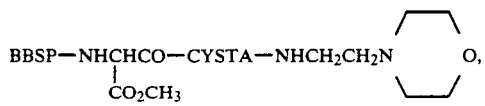
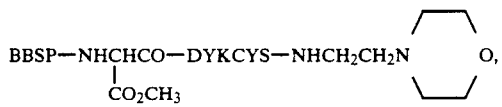
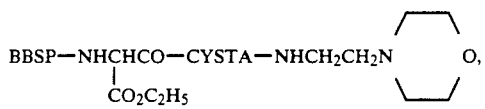
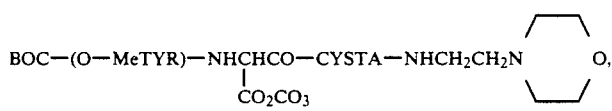
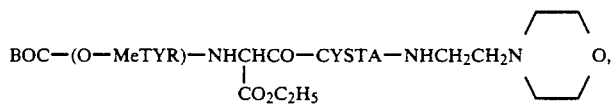
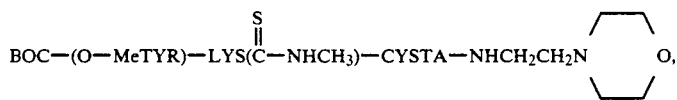
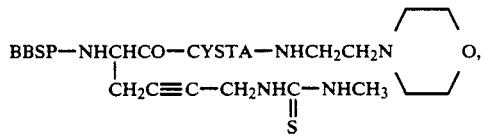
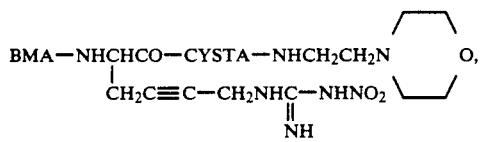
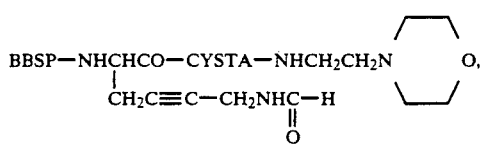

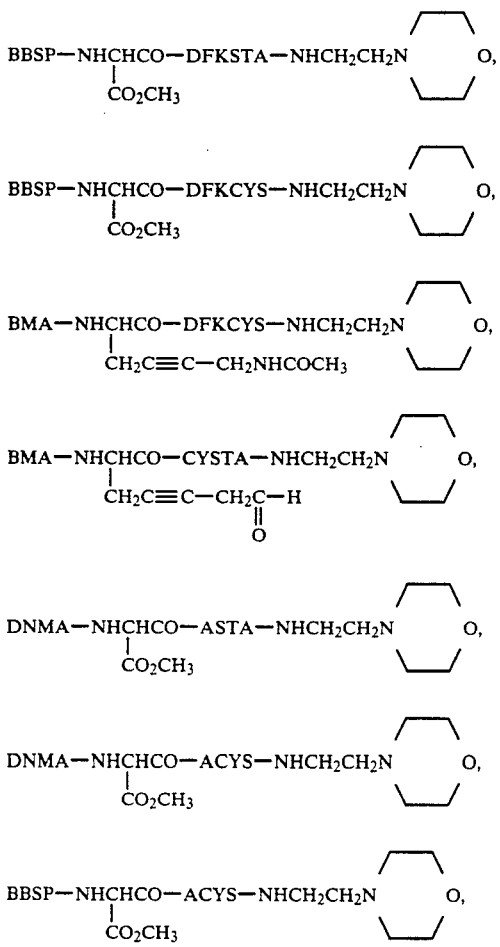

The compounds includes solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following scheme illustrates novel methods of preparing certain peptides of the present invention.

SCHEME I

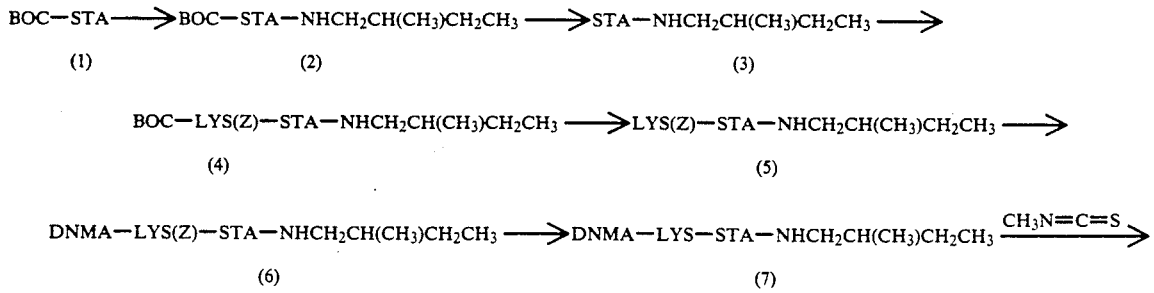

-continued
SCHEME I

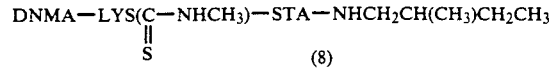

(8)

According to Scheme I above, BOC-protected statine (1) is reacted with a primary amine, for example, 2-methylbutylamine, to form the corresponding BOC-protected compound (2). The reaction takes place in an inert solvent much as methylene chloride, tetrahydrofuran, chloroform, dioxane, or ethyl acetate. The preferred solvent is methylene chloride. The reaction time varies from 1 to 24 hours. Preferably it takes about 2 to 6 hours. The reaction temperature may also vary from about 15° C. to 30° C. Preferably it is approximately 25° C.

The above compound (2) is reacted with a strong acid such as HCl to remove the BOC-protecting group thus forming corresponding compound (3) with a free amino terminus.

The protecting group is removed with a strong acid such as trifluoroacetic, HCl, or BHr. Preferably HCl is used.

The term protecting group refers to those groups intended to protect the N-terminus against undesirable reactions during synthetic procedures or to increase the solubility of the desired final compounds and includes but is not limited to Z and BOC.

Compound 3 is then reacted with BOC-protected LYS(Z) to form the corresponding compound (4). This reaction takes place in an inert solvent, for example DMF, with hydroxybenzotriazole, dicyclohexylcarbodiimide and triethylamine at temperatures of from 0° C. to 25° C. The reaction may take as long as 72 hours.

This compound (4) is reacted with a strong acid, such as trifluoroacetic acid, to form the corresponding compound with a free amino terminus (5). The reaction takes place in an inert solvent, preferably dichloromethane, at about 25° C., taking from 0.5 to 2 hours.

This compound (5) is reacted with di-(1-naphthylmethyl) acetic acid in an inert solvent such as DMF at approximately room temperature for from 4 to 16 hours to form a DNMA-terminated peptide (6). The Z group is then removed by catalytic hydrogenation in a polar, inert solvent such as methanol forming peptide (7). The catalyst is preferably palladium on carbon.

This peptide (7) is reacted with methyl isocyanate or methyl isothiocyanate at about room temperature for from 2 to 16 hours in an inert solvent such as methylene chloride to form a compound of the present invention (8).

For compounds of the types illustrated in Examples 1 and 4 the BOC-protected statine is reacted with LEU-NHCH$_2$Ph.HCl to form the corresponding BOC-protected compound, for example, BOC-STA-LEU-NHCH$_2$Ph. This compound is reacted with HCl to form the corresponding compound with a free amino terminus. This is reacted with BOC-PHE-ARG(NO$_2$) to form a compound of the present invention.

The BOC-PHE-ARG(NO$_2$) is prepared by reacting ARG(NO$_2$)-OCH$_3$.HCl with BOC-PHE to form the corresponding methyl carboxylic acid ester, BOC-PHE-ARG(NO$_2$)-OCH$_3$. This ester is converted to the free carboxylic acid by reaction with a strong base such as sodium hydroxide.

Alternatively the diamide (STA-LEU-NHCH$_2$Ph) with a free amino terminus is reacted with Z-ORN(PHT) to form the corresponding compound, Z-ORN(PHT)-STA-LEU-NHCH$_2$Ph. This compound is hydrogenated thus removing the Z group to form ORN(PHT)-STA-LEU-NHCH$_2$Ph. This peptide is reacted with BOC-PHE to form a desired compound of the present invention.

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, N.Y., 1979, Vol. 1, p. 42–44.

The DCC/HOBT method of coupling is well known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, N.Y., 1979, Vol. 1, p. 241–261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The acyl groups derived from the substituted succinic acid amides may be prepared as follows. 1-Naphthaldehyde is reacted with diethyl succinate in a Stobbe condensation, and the corresponding di-acid is converted to the anhydride with acetic anhydride. Treatment with the appropriate amine gives 2-(1-naphthylmethylene)-3-(substituted aminocarbonyl) propionic acid. Catalytic hydrogenation gives the desired 2-(1-naphthylmethyl)-3-(substituted aminocarbonyl)propionic acid. This acid may be condensed with suitably protected amino acids using the coupling methods known to peptide chemistry, for example, the carbodiimide method. This is discussed in European Application Publication No. 206,807 and European Application Publication No. 200,406.

The compounds of the present invention are useful for treating renin-associated hypertension, congestive heart failure, and hyperaldosteronism. They are also useful as diagnostic tools for determining the presence of renin-associated hypertension or hyperaldosteronism.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

Aryl means phenyl or other aromatic groups, including mono- or bicyclic, which may be substituted, especially monosubstituted, by F, Cl, Br, I, CF$_3$, OH, OR, or R.

Aralkyl is as described above for alkyl and aryl.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

Yet another important aspect of the present invention is a method of treating congestive heart failure in a mammal which comprises administering a pharmaceutical composition containing an effective amount of a compound of the invention in combination with a pharmaceutically acceptable carrier.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the IC$_{50}$, which is the molar concentration of test compound causing a 50% inhibition of the renin activity or as the percent inhibition at $10^{-6}$ molar concentration.

TABLE II

| Compound | IC$_{50}$ (M) |
|---|---|
| BOC—PHE—ORN(PHT)—STA—LEU—NHCH$_2$Ph | $9.1 \times 10^{-7}$ |
| BOC—PHE—ARG(NO$_2$)—STA—LEU—NHCH$_2$Ph | $6.3 \times 10^{-8}$ |
| DNMA—LYS(C(=S)—NHCH$_3$)—STA—NHCH$_2$CH(CH$_3$)CH$_2$CH$_3$ | $9.6 \times 10^{-9}$ |
| DNMA—LYS(C(=O)—NHCH$_3$)—STA—NHCH$_2$CH(CH$_3$)CH$_2$CH$_3$ | $2.9 \times 10^{-8}$ |
| DNMA—LYS(C(=S)—NH(CH$_2$)$_3$CH$_3$)—STA—NHCH$_2$CH(CH$_3$)CH$_2$CH$_3$ | $4.6 \times 10^{-8}$ |
| DNMA—LYS(C(=S)—NHPh)—STA—NHCH$_2$CH(CH$_3$)CH$_2$CH$_3$ | $5.8 \times 10^{-8}$ |
| DNMA—LYS(C(=S)—NHC(CH$_3$)$_2$CH$_2$CH$_3$)—STA—NHCH$_2$CH(CH$_3$)CH$_2$CH$_3$ | $4.5 \times 10^{-7}$ |
| DNMA—LYS(C(=S)—NHCH$_3$)—CYSTA—NHCH$_2$CH(CH$_3$)CH$_2$CH$_3$ | $7.5 \times 10^{-9}$ |
| DNMA—LYS(C(=NH)—NHNO$_2$)—CYSTA—NHCH$_2$CH(CH$_3$)CH$_2$CH$_3$ | $1.5 \times 10^{-8}$ |
| DNMA—LYS(P(=O)—(OPh)$_2$)—STA—NHCH$_2$CH(CH$_3$)CH$_2$CH$_3$ | $7.4 \times 10^{-6}$ |
| DNMA—LYS(C(=NCN)—SCH$_3$)—STA—NHCH$_2$CH(CH$_3$)CH$_2$CH$_3$ | $1.9 \times 10^{-8}$ |
| DNMA—LYS(C(=NCN)—NH$_2$)—STA—NHCH$_2$CH(CH$_3$)CH$_2$CH$_3$ | $1.8 \times 10^{-8}$ |
| DNMA—LYS(C(=NCN)—NHCH$_3$)—STA—NHCH$_2$CH(CH$_3$)CH$_2$CH$_3$ | $1.5 \times 10^{-8}$ |
| DNMA—NHCH(—(CH$_2$)$_4$—N-pyrrolyl)CO—STA—NHCH$_2$CH(CH$_3$)CH$_2$CH$_3$ | $8.7 \times 10^{-8}$ |
| DNMA—NHCH(—(CH$_2$)$_3$—N-pyrrolyl)CO—STA—NHCH$_2$CH(CH$_3$)CH$_2$CH$_3$ | $5.4 \times 10^{-7}$ |

TABLE II-continued

| Compound | IC$_{50}$ (M) |
|---|---|
| DNMA—LYS(Z)—STA—LEU—NHCH$_2$Ph | $2.9 \times 10^{-6}$ |
| DNMA—LYS(C(=NH)—NHNO$_2$)—STA—LEU—NHCH$_2$Ph | $1.5 \times 10^{-8}$ |
| DNMA—LYS(C(=S)—NHCH$_3$)—STA—LEU—NHCH$_2$Ph | $6.0 \times 10^{-8}$ |
| DNMA—LYS(C(=O)—NHCH$_3$)—STA—LEU—NHCH$_2$Ph | $8.4 \times 10^{-8}$ |
| DNMA—NHCH((CH$_2$)$_5$—NHZ)CO—STA—NHCH$_2$CH(CH$_3$)CH$_2$CH$_3$ | $2.9 \times 10^{-7}$ |
| DNMA—NHCH((CH$_2$)$_5$—NHC(=S)—NHCH$_3$)CO—STA—NHCH$_2$CH(CH$_3$)CH$_2$CH$_3$ | $4.0 \times 10^{-8}$ |
| DNMA—NHCH((CH$_2$)$_5$—NHC(=NH)—NHNO$_2$)CO—STA—NHCH$_2$CH(CH$_3$)CH$_2$CH$_3$ | $2.6 \times 10^{-8}$ |
| DNMA—NHCH((CH$_2$)$_5$—NHC(=S)—NHCH$_3$)CO—STA—LEU—NHCH$_2$Ph | 49% @ $10^{-6}$ |
| DNMA—NHCH((CH$_2$)$_5$—NHC(=NH)—NHNO$_2$)CO—STA—LEU—NHCH$_2$Ph | $1.1 \times 10^{-7}$ |
| DNMA—NHCH((CH$_2$)$_6$—NHZ)CO—STA—NHCH$_2$CH(CH$_3$)CH$_2$CH$_3$ | 28% @ $10^{-6}$ |
| DNMA—NHCH((CH$_2$)$_6$—NHC(=S)—NHCH$_3$)CO—STA—NHCH$_2$CH(CH$_3$)CH$_2$CH$_3$ | $4.5 \times 10^{-8}$ |
| DNMA—NHCH((CH$_2$)$_6$—NHC(=NCN)—NH$_2$)CO—STA—NHCH$_2$CH(CH$_3$)CH$_2$CH$_3$ | $4.5 \times 10^{-8}$ |
| DNMA—NHCH((CH$_2$)$_6$—NHZ)CO—STA—LEU—NHCH$_2$Ph | $5.9 \times 10^{-8}$ |
| DNMA—NHCH(CH$_2$C≡C—CH$_2$—NHZ)CO—STA—NHCH$_2$CH(CH$_3$)CH$_2$CH$_3$ | $1.5 \times 10^{-7}$ |
| DNMA—ORN(C(=S)—NHCH$_3$)—STA—NHCH$_2$CH(CH$_3$)CH$_2$CH$_3$ | $2.8 \times 10^{-7}$ |
| DNMA—ORN(C(=O)—NHCH$_3$)—STA—NHCH$_2$CH(CH$_3$)CH$_2$CH$_3$ | $8.9 \times 10^{-7}$ |
| DNMA—LYS(C(=O)—NH$_2$)—STA—NHCH$_2$CH(CH$_3$)CH$_2$CH$_3$ | $5.0 \times 10^{-8}$ |

TABLE II-continued

| Compound | IC$_{50}$ (M) |
|---|---|
| DNMA—NHCHCO—STA—NHCH$_2$CH(CH$_3$)CH$_2$CH$_3$<br>    \|<br>    CH$_2$CH(OH)CH$_2$OH | 6.6 × 10$^{-7}$ |
| DNMA—NHCHCO—STA—NHCH$_2$CH(CH$_3$)CH$_2$CH$_3$<br>    \|<br>    CO$_2$CH$_3$ | 2.3 × 10$^{-8}$ |
| BOC—PHE—NHCHCO—STA—NHCH$_2$CH(CH$_3$)CH$_2$CH$_3$<br>    \|<br>    CO$_2$CH$_3$ | 4.1 × 10$^{-8}$ |
| DNMA—NHCHCO—STA—NHCH$_2$CH(CH$_3$)CH$_2$CH$_3$<br>    \|<br>    CONH(CH$_2$)$_2$—[imidazole] | 3.1 × 10$^{-6}$ |
| DNMA—NHCHCO—STA—NHCH$_2$CH(CH$_3$)CH$_2$CH$_3$<br>    \|<br>    CONH$_2$ | 24% @ 10$^{-6}$ |
| DNMA—NHCHCO—STA—NHCH$_2$CH(CH$_3$)CH$_2$CH$_3$<br>    \|<br>    CONHCH$_3$ | 26% @ 10$^{-6}$ |
| DNMA—NHCHCO—STA—NHCH$_2$CH(CH$_3$)CH$_2$CH$_3$<br>    \|<br>    CON(CH$_3$)$_2$ | 2.0 × 10$^{-7}$ |
| DNMA—NHCHCO—STA—NHCH$_2$CH(CH$_3$)CH$_2$CH$_3$<br>    \|<br>    CH$_2$—[benzimidazole] | 2.8 × 10$^{-6}$ |
| DNMA—LYS(TOS)—STA—NHCH$_2$CH(CH$_3$)CH$_2$CH$_3$ | 3.0 × 10$^{-6}$ |
| DNMA—LYS(GO$_2$CH$_3$)—STA—NHCH$_2$CH(CH$_3$)CH$_2$CH$_3$ | 6.0 × 10$^{-8}$ |
| IVA—PHE—NHCHCO—STA—NHCH$_2$CH(CH$_3$)CH$_2$CH$_3$<br>    \|<br>    CH$_2$CN | 5.7 × 10$^{-7}$ |
| BOC—PHE—NHCHCO—STA—NHCH$_2$CH(CH$_3$)CH$_2$CH$_3$<br>    \|<br>    CO$_2$C(CH$_3$)$_3$ | 9.5 × 10$^{-7}$ |
| DNMA—NHCHCO—STA—NHCH$_2$CH(CH$_3$)CH$_2$CH$_3$<br>    \|<br>    CO$_2$C$_2$H$_5$ | 2.3 × 10$^{-8}$ |
| [naphthyl-CH$_2$]CHCO—NHCHCO—STA—NHCH$_2$CH(CH$_3$)CH$_2$CH$_3$<br>    \|                              \|<br>    CH$_2$-N(morpholine)-C=O           CO$_2$CH$_3$ | 9.8 × 10$^{-8}$ |
| DNMA—NHCHCO—STA—NHCH$_2$CH(CH$_3$)CH$_2$CH$_3$<br>    \|<br>    (CH$_2$)$_5$—CONHCH$_3$ | 1.2 × 10$^{-6}$ |
| DNMA—NHCH[(CH$_2$)$_3$CH=CH$_2$]CO—STA—LEU—NHCH$_2$Ph<br>(Isomer A) | 9.1 × 10$^{-8}$ |
| DNMA—NHCH[(CH$_2$)$_3$CH=CH$_2$]CO—STA—LEU—NHCH$_2$Ph<br>(Isomer B) | 3.5 × 10$^{-6}$ |

TABLE II-continued

| Compound | IC$_{50}$ (M) |
|---|---|
| DNMA—NHCH[(CH$_2$)$_3$CH—O—CH$_2$]CO—STA—LEU—NHCH$_2$Ph (Isomer A) | 5.7 × 10$^{-8}$ |
| DNMA—NHCH[(CH$_2$)$_3$CH—O—CH$_2$]CO—STA—LEU—NHCH$_2$Ph (Isomer B) | 47% @ 10$^{-6}$ |
| DNMA—NHCHCO—STA—NHCH$_2$CH(CH$_3$)CH$_2$CH$_3$<br>\|<br>CO$_2$CH(CH$_3$)$_2$ | 3.3 × 10$^{-8}$ |
| DNMA—NHCHCO—STA—NHCH$_2$CH(CH$_3$)CH$_2$CH$_3$<br>\|<br>CH$_2$C≡C—CH$_2$NHCOOCH$_3$ | 2.0 × 10$^{-9}$ |
| DNMA—NHCHCO—STA—NHCH$_2$CH(CH$_3$)CH$_2$CH$_3$ (Isomer B),<br>\|<br>CH$_2$C≡C—CH$_2$NHCOCH$_3$ | 2.9 × 10$^{-8}$ |
| DNMA—NHCHCO—STA—NHCH$_2$CH(CH$_3$)CH$_2$CH$_3$,<br>\|<br>CH$_2$CH=CHCH$_2$NHCOCH$_3$<br>(Z) | 1.0 × 10$^{-7}$ |
| DNMA—NHCHCO—CYSTA—NHCH$_2$CH$_2$N⟨O⟩<br>\|<br>CH$_2$C≡C—CH$_2$NHBOC | 7.0 × 10$^{-7}$ |
| DNMA—NHCHCO—CYSTA—NHCH$_2$CH$_2$N⟨O⟩,<br>\|<br>CH$_2$C≡C—CH$_2$NHC—H<br>‖<br>O | 8.0 × 10$^{-9}$ |
| DNMA—NHCHCO—CYSTA—NHCH$_2$CH$_2$N⟨O⟩,<br>\|<br>CH$_2$C≡C—CH$_2$NHCOCH$_3$ | 8.6 × 10$^{-9}$ |
| DNMA—NHCHCO—CYSTA—NHCH$_2$CH$_2$N⟨O⟩,<br>\|<br>CH$_2$C≡C—CH$_2$NHC—NHNO$_2$<br>‖<br>NH | 1.2 × 10$^{-8}$ |
| DNMA—NHCHCO—CYSTA—NHCH$_2$CH$_2$N⟨O⟩,<br>\|<br>CH$_2$C≡C—CH$_2$NHC—NHCH$_3$<br>‖<br>S | 4.8 × 10$^{-8}$ |
| BBSP—LYS(C̈NHCH$_3$)—CYSTA—NHCH$_2$CH$_2$N⟨O⟩,<br>S‖ | 2.7 × 10$^{-8}$ |
| DNMA—LYS(C̈CH$_2$SCH$_3$)—STA—NHCH$_2$CH(CH$_3$)CH$_2$CH$_3$,<br>O‖ | 9.8 × 10$^{-8}$ |
| DNMA—LYS(C̈CH$_2$SO$_2$CH$_3$)—STA—NHCH$_2$CH(CH$_3$)CH$_2$CH$_3$,<br>O‖ | 6.8 × 10$^{-8}$ |
| DNMA—LYS(C̈CH$_2$SOCH$_3$)—STA—NHCH$_2$CH(CH$_3$)CH$_2$CH$_3$,<br>O‖ | 4.1 × 10$^{-8}$ |

TABLE II-continued

| Compound | IC$_{50}$ (M) |
|---|---|
| DNMA—NHCHCO—CHSTA—NHCH$_2$CH(CH$_3$)CH$_2$CH$_3$,<br>　　　　　｜<br>　　　　CO$_2$CH$_3$ | $5.2 \times 10^{-8}$ |
| DNMA—NHCHCO—CHSTA—NHCH$_2$CH$_2$N⟨morpholine⟩O,<br>　　　　　｜<br>　　　　CO$_2$CH$_3$ | $1.4 \times 10^{-7}$ |
| 　　　　　　S<br>　　　　　　‖<br>DNMA—LYS(CNHCH$_3$)—CHSTA—NHCH$_2$CH(CH$_3$)CH$_2$CH$_3$, | $2.3 \times 10^{-8}$ |
| [1-Naphthylmethyl-(morpholinyl-N-C=O)CH]CHCO—LYS(CSCH$_3$, =NCN)—STA—NHCH$_2$CH$_2$N⟨morpholine⟩O, | $3.5 \times 10^{-7}$ |
| [1-Naphthylmethyl-(morpholinyl-N-C=O)CH]CHCO—LYS(CNHNO$_2$, =NH)—STA—NHCH$_2$CH$_2$N⟨morpholine⟩O, | $4.2 \times 10^{-7}$ |
| [1-Naphthylmethyl-(morpholinyl-N-C=O)CH]CHCO—LYS(CNHCH$_3$, =S)—STA—NHCH$_2$CH$_2$N⟨morpholine⟩O, | $5.6 \times 10^{-7}$ |
| [1-Naphthylmethyl-(morpholinyl-N-C=O)CH]CHCO—NHCHCO—STA—NHCH$_2$CH(CH$_3$)CH$_2$CH$_3$,<br>　　　　　　　　　　　　　｜<br>　　　　　　　　　　　CH$_2$CN | $2.5 \times 10^{-7}$ |
| DNMA—NHCHCO—STA—NHCH$_2$CH(CH$_3$)CH$_2$CH$_3$,<br>　　　　｜<br>　　CH$_2$CN | $1.7 \times 10^{-7}$ |

TABLE II-continued

| Compound | $IC_{50}$ (M) |
|---|---|
| [naphthyl-CH(CH₂-N(morpholine)C=O)-CHCO]—NHCHCO—CYSTA—NHCH₂CH₂N(morpholine), with CH₂CN branch (fast isomer) | 5.4% inhib @ $10^{-8}$ M |
| [naphthyl-CH(CH₂-N(morpholine)C=O)-CHCO]—NHCHCO—CYSTA—NHCH₂CH₂N(morpholine), with CH₂CN branch (slow isomer) | $1.2 \times 10^{-7}$ |
| DNMA—LYS(C(=S)NHCH₃)—CYSTA—NHCH₂CH₂N(morpholine), | $2.9 \times 10^{-8}$ |
| [naphthyl-CH(CH₂-N(morpholine)C=O)-CHCO]—LYS(C(=S)NHCH₃)—CYSTA—NHCH₂CH₂N(morpholine), | $2.0 \times 10^{-8}$ |
| DNMA—LYS(C(=S)NHCH₃)—STA—NHCH₂CH₂N(morpholine), | $1.2 \times 10^{-7}$ |
| DNMA—LYS(C(=NH)NHNO₂)—STA—NHCH₂CH₂N(morpholine), | $4.5 \times 10^{-8}$ |
| DNMA—LYS(C(=NCN)SCH₃)—STA—NHCH₂CH₂N(morpholine), | $9.0 \times 10^{-8}$ |
| DNMA—NHCHCO—STA—NHCH₂CH(CH₃)CH₂CH₃, with CH₂CH=CHCH₂NHC(=S)NHCH₃ branch (E) | $4.1 \times 10^{-8}$ |
| DNMA—LYS(C(=S)NHCH₃)—DFSTA—NHCH₂CH₂N(morpholine), | $2.4 \times 10^{-7}$ |
| MNPP—LYS(C(=S)NHCH₃)—STA—NHCH₂CH(CH₃)CH₂CH₃, | $1.4 \times 10^{-7}$ |

TABLE II-continued

| Compound | IC$_{50}$ (M) |
|---|---|
| BOC—PHE—NHCHCO—STA—NHCH$_2$CH(CH$_3$)CH$_2$CH$_3$, with O=C—N(pyrrolidine) substituent on the NHCHCO | $4.0 \times 10^{-7}$ |
| DNMA—NHCHCO—STA—LEU—NHCH$_2$—(pyridine), with CO$_2$C$_2$H$_5$ substituent on the NHCHCO | $1.3 \times 10^{-8}$ |
| BOC—PHE—NHCHCO—STA—NHCH$_2$CH(CH$_3$)CH$_2$CH$_3$, with CH$_2$CN substituent on the NHCHCO | $2.6 \times 10^{-7}$ |

As can be seen from the above table, the compounds of the present invention have a significant effect on the activity of renin and thus are useful for the treatment of hypertension, congestive heart failure, and hyperaldosteronism.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient.

The compositions can, if desired, also contain other compatible therapeutic agents.

In therapeutic use as renin inhibitors, the mammalian dosage range for a 70 kg subject is from 1 to 1500 mg per day or preferably 25 to 750 mg per day optionally in divided portions. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

BOC-PHE-ARG(NO$_2$)-STA-LEU-NHCH$_2$Ph

A solution of 1.06 g of STA-LEU-NHCH$_2$Ph.HCl, 1.2 g BOC-PHE-ARG(NO$_2$), and 0.37 g HOBT in 80 ml of a 5/3 solution of CH$_2$Cl$_2$/DMF was cooled in ice and treated with 0.7 ml of Et$_3$N. DCC (0.59 g) was then added and the solution kept at 0° for one hour, then at room temperature overnight. The solvent was removed under reduced pressure, and the residue taken up in EtOAc. Insolubles were filtered off and the filtrate was washed with Na$_2$CO$_3$ solution, citric acid solution, and brine. After drying over MgSO$_4$ and removal of the solvent under reduced pressure, the residue was chromatographed on silica gel, eluting with a gradient of CH$_2$Cl$_2$/MeOH (97/3) to CH$_2$Cl$_2$/MeOH (92/8). Combining the appropriate fractions gave 1.74 g (82%) of the product as a white foam.

Calcd. for C$_{41}$H$_{63}$N$_9$O$_9$ (MW 826.01): C, 59.62; H, 7.69; N, 15.26 Found C, 59.49; H, 7.48; N, 14.59.

EXAMPLE 2

DNMA—LYS(CNHCH$_3$)—STA—NHCH$_2$CH(CH$_3$)CH$_2$CH$_3$

DNMA-LYS-STA-NHCH$_2$CH(CH$_3$)CH$_2$CH$_3$ (0.5 g) was dissolved in dichloromethane (15 ml) and cooled to 0°. Methyl isothiocyanate (0.053 g) was added, and the mixture was allowed to warm to 25° and stir for six hours. The solvent was evaporated and the crude product was purified by chromatography on silica gel, eluting with a gradient of EtOAc/hexane (1:1) to pure EtOAc. The appropriate fractions were combined to give 0.3 g of product.

Calcd. for C$_{45}$H$_{61}$N$_5$O$_4$S..0.25 C$_4$H$_8$O$_2$0.5 H$_2$O: C, 69.13; H, 8.07; N, 8.76 Found C, 69.13; H, 8.19; N, 8.84.

EXAMPLE 3

DNMA—LYS(CNHCH$_3$)—STA—NHCH$_2$CH(CH$_3$)CH$_2$CH$_3$

DNMA-LYS-STA-NHCH$_2$CH(CH$_3$)CH$_2$CH$_3$ (0.5 g) was dissolved in dichloromethane (15 ml) and cooled to 0°. Methyl isocyanate (0.042 ml) was added, and the mixture was allowed to warm to 25° and stir for 4 hours. EtOAc was added to the white suspension and the mixture was filtered and the solid dried to give 0.3 g of product.

Calcd. for C$_{45}$H$_{66}$N$_5$O$_5$.0.33 C$_4$H$_8$O$_2$.0.5 H$_2$O: C, 70.41; H, 8.25; N, 8.86 Found C, 70.26; H, 8.35; N, 8.82.

EXAMPLE 4

BOC-PHE-ORN(PHT)-STA-LEU-NHCH$_2$Ph

BOC-PHE (0.587 g, 2.21 mmole) and HOBT.H$_2$O (0.314 g, 2.32 mmole) was dissolved in 2 ml DMF, diluted with 20 ml CH$_2$Cl$_2$, and cooled to −5°. DCC (0.48 g, 2.32 mmole) was added as a solution in 5 ml CH$_2$Cl$_2$, followed by a cooled solution of ORN(PHT)-STA-LEU-NHCH$_2$Ph (1.35 g, 2.17 mmole) in 10 ml CH$_2$Cl$_2$. After stirring at 25° overnight, the mixture was filtered, stripped, and resuspended in EtOAc. The suspension was filtered, and the filtrate was washed with 1N citric acid, giving a precipitate. The suspension was washed with brine, saturated NaHCO$_3$ solution and brine. The solids were dissolved by the addition of CHCl$_3$ and warming. Residual aqueous phase was separated, and the organic phase was dried over MgSO$_4$, filtered, and stripped to an oil. The oil was dissolved in CHCl$_3$, and a precipitate was obtained by the addition of Et$_2$O. The solid was filtered, washed with Et$_2$O, and dried giving 1.64 g of product. IR, NMR, and mass spectral analyses confirmed the structure.

Calcd. for C$_{48}$H$_{64}$N$_6$O$_9$ (MW 869.08): C, 66.34; H, 7.42; N, 9.67 Found C, 66.34; H, 7.57; N, 9.86.

EXAMPLE 5

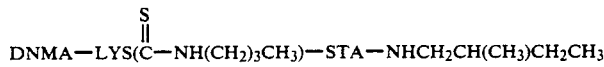
DNMA—LYS(C—NH(CH$_2$)$_3$CH$_3$)—STA—NHCH$_2$CH(CH$_3$)CH$_2$CH$_3$

Using the procedure of Example 2, but substituting n-butyl isothiocyanate for methyl isothiocyanate gave the title compound. It was purified by chromatography on silica gel, eluting with EtOAc/hexane (3/1). The structure was confirmed by NMR and mass spectroscopy.

Calcd. for C$_{48}$H$_{67}$N$_5$O$_4$S (MW 810.06): C, 71.17; H, 8.34; N, 8.65 Found C, 70.92; H, 8.33; N, 8.55.

EXAMPLE 6

DNMA—LYS(C—NHPh)—STA—NHCH$_2$CH(CH$_3$)CH$_2$CH$_3$

Using the procedure of Example 2 but substituting phenyl isothiocyanate for methyl isothiocyanate gave the title compound. It was purified by chromatography on silica gel, eluting with EtOAc/hexane (3/1). The material was transferred to a vial with the aid of CH$_2$Cl$_2$. The structure was confirmed by NMR and mass spectroscopy.

Calcd. for $C_{50}H_{63}N_5O_4S.0.2CH_2Cl_2$ (MW 847.03): C, 71.18; H, 7.54; N, 8.27 Found C, 70.94; H, 7.56; N, 8.19.

EXAMPLE 7

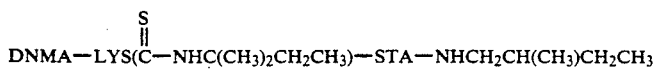
DNMA—LYS(C—NHC(CH$_3$)$_2$CH$_2$CH$_3$)—STA—NHCH$_2$CH(CH$_3$)CH$_2$CH$_3$ (with S double-bonded to C)

Using the procedure of Example 2 but substituting 2,2-dimethylpropyl isothiocyanate for methyl isothiocyanate gave the title compound. It was purified by chromatography on silica gel, eluting with EtOAc/hexane (1/1), then EtOAc. The structure was confirmed by NMR and mass spectroscopy.

Calcd. for $C_{49}H_{69}N_5O_4S$ (MW 824.08): C, 71.41; H, 8.44; N, 8.50 Found C, 71.50; H, 8.50; N, 8.43.

EXAMPLE 8

DNMA—LYS(C—NHCH$_3$)—CYSTA—NHCH$_2$CH(CH$_3$)CH$_2$CH$_3$ (with S double-bonded to C)

A solution of 500 mg (0.68 mmole) of DNMA-LYS-CYSTA-NHCH$_2$CH(CH$_3$)CH$_2$CH$_3$ in 10 ml CH$_2$Cl$_2$ was cooled in ice and 50 mg (0.68 mmole) of methyl isothiocyanate added. The solution was stirred for four days at room temperature, the solvent removed under reduced pressure, and the residue chromatographed on silica gel, eluting with EtOAc/hexane (1/1), then EtOAc. There was obtained 0.4 g of product. The structure was confirmed by NMR and mass spectroscopy.

Calcd. for $C_{48}H_{65}N_5O_4S.0.44C_4H_8O_2$ (MW 846.80): C, 70.57; H, 8.16; N, 8.27 Found C, 70.92; H, 8.24; N, 8.41.

EXAMPLE 9

DNMA—LYS(C—NHNO$_2$)—CYSTA—NHCH$_2$CH(CH$_3$)CH$_2$CH$_3$ (with NH double-bonded to C)

A solution of 400 mg (0.54 mmole) of DNMA-LYS-CYSTA-NHCH$_2$CH(CH$_3$)CH$_2$CH$_3$ in 10 ml EtOH was treated with 74 mg (0.54 mmole) of 2-methyl-1-nitro-2-thiopseudourea (J. Am. Chem. Soc. 76, 1877 (1954)) and stirred at room temperature for four days. The solvent was removed under reduced pressure and the residue chromatographed on silica gel, eluting with EtOAc/hexane (1/1), then EtOAc. There was obtained 0.35 g of product. The structure was confirmed by NMR and mass spectroscopy.

Calcd. for $C_{47}H_{63}N_7O_6.0.4C_4H_8O_2$ (MW 857.27): C, 68.09; H, 7.78; N, 11.44 Found C, 67.58; H, 7.78; N, 11.58.

EXAMPLE 10

DNMA—LYS(P—(OPh)$_2$)—STA—NHCH$_2$CH(CH$_3$)CH$_2$CH$_3$ (with O double-bonded to P)

A solution of 500 g (0.72 mmole) of DNMA-LYS-STA-NHCH$_2$CH(CH$_3$)CH$_2$CH$_3$ in 15 ml of CH$_2$Cl$_2$/THF (4/1) was cooled in ice and 0.1 ml (0.72 mmole) of Et$_3$N added, followed by 0.15 ml (0.72 mmole) of diphenyl chlorophosphate. The solution was stirred at 0° for three hours and the solvent then removed under reduced pressure. The residue was taken up in EtOAc and washed with saturated NaHCO$_3$ and saturated NaCl. Drying and removal of the solvent under reduced pressure gave the crude product which was purified by chromatography on silica gel, eluting with EtOAc/hexane (1/1) to EtOAc/hexane (5/1). There was obtained 0.46 g of product. The structure was confirmed by NMR and mass spectroscopy.

Calcd. for $C_{55}H_{67}N_4O_7P.H_2O$ (MW 945.10): C, 69.89; H, 7.36; N, 5.93 Found C, 69.64; H, 7.17; N, 6.06.

EXAMPLE 11

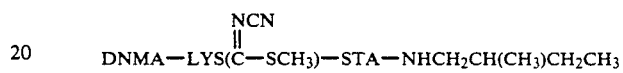
DNMA—LYS(C—SCH$_3$)—STA—NHCH$_2$CH(CH$_3$)CH$_2$CH$_3$ (with NCN double-bonded to C)

A solution of 0.31 g (0.44 mmole) of DNMA-LYS-STA-NHCH$_2$CH(CH$_3$)CH$_2$CH$_3$ in 10 ml CHCl$_3$ was treated with 70 mg (0.57 mmole) of dimethylcyanimidodithiocarbonate (Synthesis 332 (1975)) and stirred at room temperature overnight. The solvent was removed under reduced pressure and the residue chromatographed on silica gel, eluting with EtOAc/hexane (1/1), then EtOAc. There was obtained 0.3 g of product. The structure was confirmed by NMR and mass spectroscopy.

Calcd. for $C_{46}H_{60}N_6O_4S.H_2O$ (MW 811.00): C, 68.12; H, 7.71; N, 10.36 Found C, 68.23; H, 7.36; N, 10.25.

EXAMPLE 12

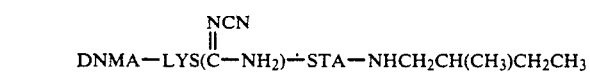
DNMA—LYS(C—NH$_2$)—STA—NHCH$_2$CH(CH$_3$)CH$_2$CH$_3$ (with NCN double-bonded to C)

A solution of 0.3 g (0.43 mmole) of DNMA-LYS-STA-NHCH$_2$CH(CH$_3$)CH$_2$CH$_3$ in 10 ml CHCl$_3$ was treated with 0.11 g (0.5 mmole) of diphenyl cyanocarboimidate and allowed to stir at room temperature overnight. The solvent was removed under reduced pressure and the residue taken up in 10 ml MeOH and ammonia bubbled through until saturated. The solution was allowed to stir at room temperature for twenty-four hours, then at 30° for five hours. The solvent was removed under reduced pressure and the residue chromatographed on silica gel, eluting with EtOAc, then EtOAc/MeOH (9/1). There was obtained 0.25 g of product. The structure was confirmed by NMR and mass spectroscopy.

Calcd. for $C_{45}H_{59}N_7O_4.1.2H_2O$ (MW 783.60): C, 68.97; H, 7.90; N, 12.51 Found C, 68.71; H, 7.57; N, 12.20.

EXAMPLE 13

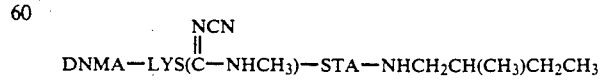
DNMA—LYS(C—NHCH$_3$)—STA—NHCH$_2$CH(CH$_3$)CH$_2$CH$_3$ (with NCN double-bonded to C)

A solution of 0.3 g (0.43 mmole) of DNMA-LYS-STA-NHCH$_2$CH(CH$_3$)CH$_2$CH$_3$ in 10 ml CHCl$_3$ was treated with 0.11 g (0.5 mmole) of diphenyl cyanocarboimidate and stirred at room temperature for one hour. The solvent was removed under reduced pressure and the residue taken up in 10 ml MeOH and methylamine gas was bubbled through the solution until saturated. After stirring for one hour, the solvent was removed under reduced pressure and the residue chromatographed on silica gel, eluting with EtOAc, then EtOAc/MeOH (9/1). There was obtained 0.26 g of product. The structure was confirmed by NMR and mass spectroscopy.

Calcd. for $C_{46}H_{61}N_7O_4 \cdot H_2O$ (MW 794.02): C, 69.58; H, 8.00; N, 12.35 Found C, 69.13; H, 7.91; N, 12.31.

EXAMPLE 14

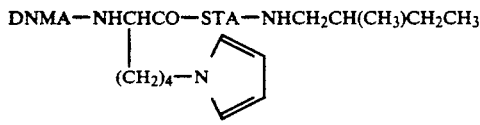

A solution of 0.5 g (1.2 mmole) of

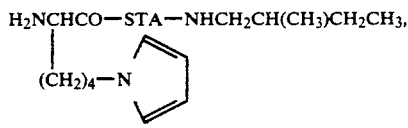

0.4 g (1.2 mmole) of di-(1-naphthylmethyl)acetic acid, and 0.16 g (1.2 mmole) of HOBT in 15 ml DMF was cooled in ice and 0.25 g (1.2 mmole) of DCC added. The solution was allowed to warm to room temperature and was stirred overnight. The mixture was filtered and the filtrate diluted with EtOAc and washed with H$_2$O, saturated NaHCO$_3$, then saturated NaCl. Drying and removal of the solvent under reduced pressure gave the crude product which was chromatographed on silica gel, eluting with EtOAc/hexane (1/1), then EtOAc/hexane (3/1). There was obtained 0.3 g of product. The structure was confirmed by NMR and mass spectroscopy.

Calcd. for $C_{47}H_{60}N_4O_4$ (MW 744.98): C, 75.77; H, 8.12; N, 7.52 Found C, 75.82; H, 8.15; N, 7.41.

EXAMPLE 15

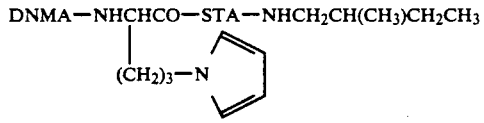

A solution of 0.51 g (1.5 mmole) of di-(1-naphthylmethyl)acetic acid, 0.61 g (1.5 mmole) of

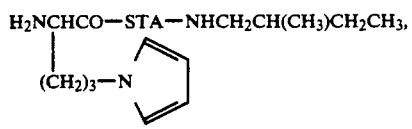

and 0.2 g (1.5 mmole) of HOBT in 15 ml DMF was cooled in ice and 0.31 g (1.5 mmole) of DCC added. The solution was allowed to stir at room temperature overnight. The mixture was filtered and the filtrate diluted with EtOAc. This was washed with H$_2$O, saturated NaHCO$_3$, H$_2$O, and saturated NaCl. Drying and removal of the solvent under reduced pressure gave the crude product which was chromatographed on silica gel, eluting with EtOAc/hexane (1/1). There was obtained 0.4 g of product. The structure was confirmed by NMR and mass spectroscopy.

Calcd. for $C_{46}H_{58}N_4O_4 \cdot 0.5H_2O$ (MW 739.96): C, 74.66; H, 8.04; N, 7.57 Found C, 74.73; H, 8.02; N, 7.66.

EXAMPLE 16

DNMA-LYS(Z)-STA-LEU-NHCH$_2$Ph

A solution of 5.6 g (8.7 mmole) of LYS(Z)-STA-LEU-NHCH$_2$Ph, 3.0 g (8.8 mmole) of di-(1-naphthylmethyl)acetic acid, and 1.18 g (8.7 mmole) of HOBT in 50 ml DMF was cooled in ice and 1.8 g (8.7 mmole) of DCC added. The solution was allowed to warm to room temperature and stir overnight. The mixture was filtered and the filtrate diluted with EtOAc and washed with H$_2$O, saturated NaHCO$_3$, and saturated NaCl. Drying and removal of the solvent under reduced pressure gave the crude product which was chromatographed on silica gel, eluting with EtOAc/CHCl$_3$ (1/1), then EtOAc/CHCl$_3$ (4/1). There was obtained 5.5 g of the product. The structure was confirmed by NMR and mass spectroscopy.

Calcd. for $C_{59}H_{71}N_5O_7$ (MW 962.20): C, 73.64; H, 7.44; N, 7.28 Found C, 73.81; H, 7.46; N, 7.40.

EXAMPLE 17

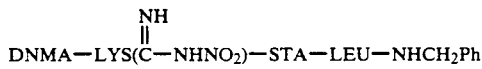

A solution of 1.0 g (1.2 mmole) of DNMA-LYS-STA-LEU-NHCH$_2$Ph in 50 ml EtOH was treated with 0.18 g (1.3 mmole) of 2-methyl-1-nitro-2-thiopseudourea and stirred for three days at room temperature with periodic warming to dissolve the white solid which formed. The solvent was then removed under reduced pressure and the residue chromatographed on silica gel, eluting with EtOAc/CHCl$_3$ (1/1), then EtOAc/CHCl$_3$ (3/1). There was obtained 0.5 g of product. The structure was confirmed by NMR and mass spectroscopy.

Calcd. for $C_{52}H_{66}N_8O_7 \cdot 0.4CHCl_3$ (MW 962.87): C, 65.36; H, 6.95; N, 11.64 Found C, 65.43; H, 7.09; N, 11.49.

EXAMPLE 18

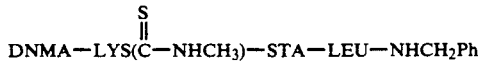

A suspension of 1.5 g (1.8 mmole) of DNMA-LYS-STA-LEU-NHCH$_2$Ph in 20 ml of CHCl$_3$ was treated with a small amount of DMF to effect solution, and then treated with 90 mg (1.23 mmole) of methyl isothiocyanate and 0.25 ml (1.8 mmole) of Et$_3$N and stirred at room temperature overnight. The solvent was removed under reduced pressure and the residue chromatographed on silica gel, eluting with CHCl$_3$. There was obtained 1.2 g of product. The structure was confirmed by NMR and mass spectroscopy.

Calcd. for $C_{53}H_{68}N_6O_5S \cdot 0.4CHCl_3$ (MW 948.88): C, 67.59; H, 7.27; N, 8.86 Found C, 67.37; H, 7.39; N, 8.94.

EXAMPLE 19

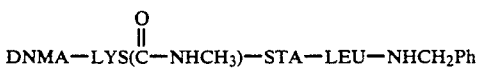

A solution of 1.0 g (1.2 mmole) of DNMA-LYS-STA-LEU-NHCH$_2$Ph in 20 ml DMF was treated with 0.08 ml (1.4 mmole) of methyl isocyanate and 0.2 ml (1.4 mmole) of Et$_3$N and stirred at room temperature for two days. The solvent was removed under high vacuum and the residue chromatographed on silica gel, eluting with CHCl$_3$/EtOAc (9/1). Since the product was contaminated with a little DMF, it was taken up in EtOAc and washed with H$_2$O. Drying and removal of the solvent under reduced pressure gave 0.9 g of the product. The structure was confirmed by NMR and mass spectroscopy.

Calcd. for C$_{53}$H$_{68}$N$_6$O$_6$.1.3H$_2$O (MW 908.54): C, 70.06; H, 7.83; N, 9.25 Found C, 70.08; H, 7.70; N, 9.37.

EXAMPLE 20

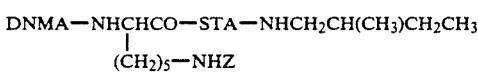

A solution of 2.1 g (3.4 mmole) of

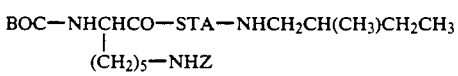

in 20 ml CH$_2$Cl$_2$ was treated with 3 ml TFA and stirred for three hours at room temperature. The solvent was removed under reduced pressure and the residue mixed with sodium carbonate solution and extracted with EtOAc. The EtOAc was washed with saturated NaCl, dried, and the solvent removed under reduced pressure leaving the intermediate

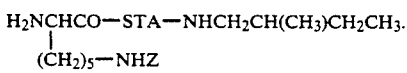

This was taken up in 15 ml DMF and treated with 1.15 g (3.4 mmole) of di-(1-naphthylmethyl)acetic acid and 0.46 g (3.4 mmole) of HOBT. The solution was cooled in ice and 0.7 g (3.4 mmole) of DCC added and the solution allowed to stir at room temperature overnight. The mixture was filtered and the filtrate diluted with EtOAc and washed with H$_2$O, saturated NaHCO$_3$, and saturated NaCl. Drying and removal of the solvent under reduced pressure gave the crude product which was chromatographed on silica gel, eluting with hexane/EtOAc (3/1), then hexane/EtOAc (1/1). There was obtained 1.6 g of product. The structure was confirmed by NMR and mass spectroscopy.

Calcd. for C$_{52}$H$_{66}$N$_4$O$_6$.0.5H$_2$O (MW 852.09): C, 73.29; H, 7.93; N, 6.58 Found C, 72.92; H, 7.65; N, 6.40.

EXAMPLE 21

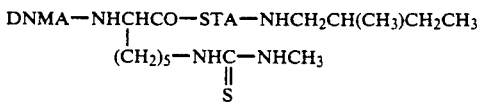

A solution of 0.3 g (0.4 mmole) of

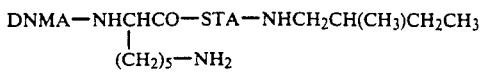

in 10 ml CHCl$_3$ was treated with 34 mg (0.46 mmole) of methyl isothiocyanate and stirred at room temperature overnight. The solvent was removed under reduced pressure and the crude product chromatographed on silica gel, eluting with EtOAc. There was obtained 0.3 g of product. The product was transferred to a vial with the aid of CH$_2$Cl$_2$. The structure was confirmed by NMR and mass spectroscopy.

Calcd. for C$_{46}$H$_{63}$N$_5$O$_4$S.0.3CH$_2$Cl$_2$ (MW 807.49): C, 68.86; H, 7.94; N, 8.67 Found C, 68.73; H, 8.03; N, 8.46.

EXAMPLE 22

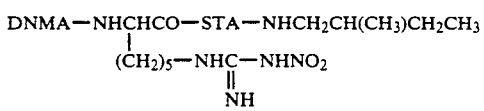

A solution of 0.42 g (0.6 mmole) of

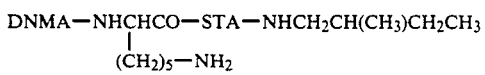

in 15 ml EtOH was treated with 0.1 g (0.7 mmole) of 2-methyl-1-nitro-2-thiopseudourea and stirred at room temperature overnight. The solvent was then removed under reduced pressure and the residue chromatographed on silica gel, eluting with hexane/EtOAc (1/1). The material was transferred to a vial with the aid of CH$_2$Cl$_2$ giving 0.4 g of product. The structure was confirmed by NMR and mass spectroscopy.

Calcd. for C$_{45}$H$_{61}$N$_7$O$_6$.0.3CH$_2$Cl$_2$ (MW 821.48): C, 66.23; H, 7.56; N, 11.94 Found C, 66.07; H, 7.73; N, 11.86.

EXAMPLE 23

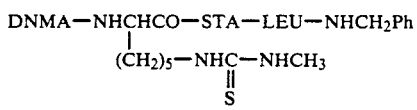

A solution of 0.5 g (0.6 mmole) of

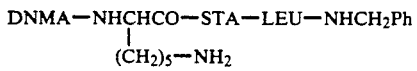

in 15 ml of CH$_2$Cl$_2$/THF (3/1) was cooled to 0° and 44 mg (0.6 mmole) of methyl isothiocyanate added together with a few drops of Et$_3$N. The solution was allowed to warm to room temperature and was stirred overnight. The solvent was removed under reduced pressure and the residue chromatographed on silica gel, eluting with EtOAc. The material was transferred to a vial with the aid of CH$_2$Cl$_2$. There was obtained 0.5 g of product. The structure was confirmed by NMR and mass spectroscopy.

Calcd. for C$_{54}$H$_{70}$N$_6$O$_5$S.0.33C$_4$H$_8$O$_2$.0.1CH$_2$Cl$_2$ (MW 952.72): C, 69.86; H, 7.71; N, 8.82 Found C, 69.59; H, 7.54; N, 9.03.

EXAMPLE 24

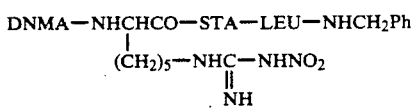

A solution of 0.5 g (0.6 mmole) of

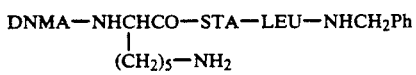

in 10 ml EtOH was treated with 0.13 g (1.0 mmole) of 2-methyl-1-nitro-2-thiopseudourea and stirred at room temperature overnight. The solvent was removed under reduced pressure and the residue chromatographed on silica gel, eluting with EtOAc/hexane (1/1), then EtOAc. The material was transferred to a vial with the aid of $CH_2Cl_2$ to give 0.4 g of product. The structure was confirmed by NMR and mass spectroscopy.

Calcd. for $C_{53}H_{68}N_8O_7 \cdot 0.33C_4H_8O_2 \cdot 0.33CH_2Cl_2$ (MW 986.12): C, 66.55; H, 7.29; N, 11.36 Found C, 66.26; H, 7.22; N, 11.58.

EXAMPLE 25

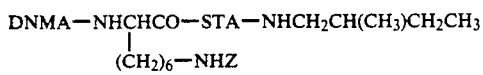

A solution of 1.3 g (2.0 mmole) of

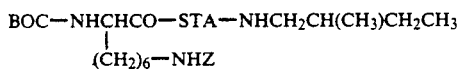

in 20 ml $CH_2Cl_2$ was treated with 3 ml TFA and allowed to st for three hours. The solvent was removed under reduced pressure, mixed with sodium carbonate solution, and extracted with EtOAc. The EtOAc was washed with saturated NaCl, dried, and the solvent removed under reduced pressure to give

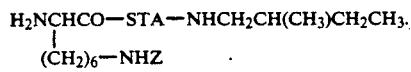

This was dissolved in 15 ml DMF and 0.7 g (2.1 mmole) of di-(1-naphthylmethyl)acetic acid and 0.28 (2.1 mmole) of HOBT added. The solution was cooled in ice and 0.42 g (2.0 mmole) of DCC added. The solution was stirred at room temperature overnight. The mixture was filtered and the filtrate diluted with EtOAc. The EtOAc was washed with $H_2O$, saturated $NaHCO_3$, and saturated NaCl. Drying and removal of the solvent under reduced pressure gave the crude product which was chromatographed on silica gel, eluting with hexane/EtOAc (3/1), then hexane/EtOAc (1/1). There was obtained 1.4 g of product. The structure was confirmed by NMR and mass spectroscopy.

Calcd. for $C_{53}H_{68}N_4O_6 \cdot 0.14C_4H_8O_2$ (MW 869.44): C, 73.99; H, 8.01; N, 6.44 Found C, 73.29; H, 8.08; N, 6.42.

EXAMPLE 26

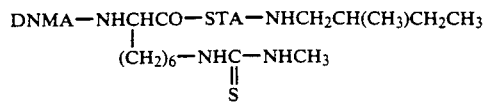

A solution of 0.42 g (0.6 mmole) of

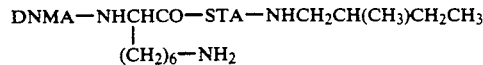

in 10 ml $CHCl_3$ was cooled in ice and treated with 48 mg (0.66 mmole) of methyl isothiocyanate, and the solution then stirred at room temperature overnight. The solvent was removed under reduced pressure and the residue chromatographed on silica gel, eluting with EtOAc. There was obtained 0.34 g of product. The structure was confirmed by NMR and mass spectroscopy.

Calcd. for $C_{47}H_{65}N_5O_4S \cdot 0.33C_4H_8O_2$ (MW 825.10): C, 70.33; H, 8.26; N, 8.49 Found C, 69.94; H, 8.24; N, 8.56.

EXAMPLE 27

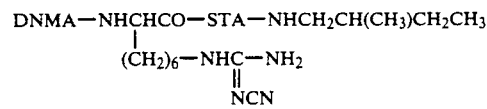

A solution of 0.67 g (0.9 mmole) of

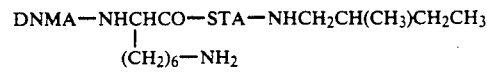

in 10 ml $CHCl_3$ was treated with 0.2 g (0.8 mmole) of diphenyl cyanocarboimidate and allowed to stir at room temperature overnight. The solvent was evaporated under reduced pressure and the residue taken up in 20 ml MeOH and ammonia bubbled through until saturated. The solution was allowed to stir at room temperature overnight, the solvent removed under reduced pressure, and the residue chromatographed on silica gel, eluting with EtOAc/MeOH (9/1). There was obtained 0.6 g of product. The structure was confirmed by NMR and mass spectroscopy.

Calcd. for $C_{47}H_{63}N_7O_4 \cdot 0.75CH_3OH$ (MW 814.06): C, 70.45; H, 8.17; N, 12.05 Found C, 70.34; H, 8.31; N, 12.10.

EXAMPLE 28

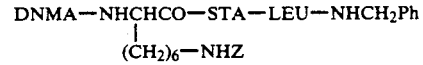

A solution of 1.0 g (1.3 mmole) of

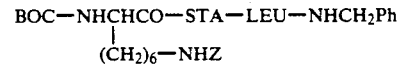

in 20 ml of $CH_2Cl_2$ was treated with 4 ml of TFA and allowed to stir at room temperature for two hours. The solvent was removed under reduced pressure and the residue taken up in EtOAc and washed with saturated NaHCO$_3$ and saturated NaCl. Drying and removal of the solvent under reduced pressure gave

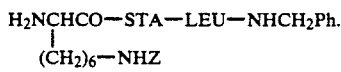

This was taken up in 15 ml DMF and 0.44 g (1.3 mmole) of di-(1-naphthylmethyl)acetic acid and 0.18 g (1.3 mmole) of HOBT added. The solution was cooled in ice and 0.27 g (1.3 mmole) DCC was added and the solution allowed to stir at room temperature for three days. The mixture was filtered and the filtrate diluted with EtOAc and washed with H$_2$O, saturated NaHCO$_3$, and saturated NaCl. Drying and removal of the solvent under reduced pressure gave the crude product which was chromatographed on silica gel, eluting with EtOAc/hexane (1/1). There was obtained 1.0 g of product. The structure was confirmed by NMR and mass spectroscopy.

Calcd. for C$_{61}$H$_{75}$N$_5$O$_7$ (MW 990.25): C, 73.98; H, 7.63; N, 7.07 Found C, 73.67; H, 7.87; N, 7.24.

EXAMPLE 29

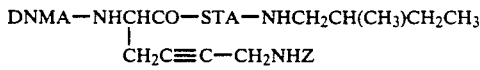

A solution of 1.3 g (2.4 mmole) of

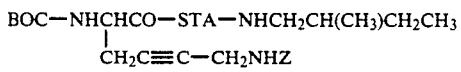

in 30 ml CH$_2$Cl$_2$ was treated with 4 ml of TFA and allowed to stir at room temperature for two hours. The solvent was removed under reduced pressure and the residue mixed with sodium carbonate solution and extracted with EtOAc. The EtOAc was washed with H$_2$O and saturated NaCl. Drying and removal of the solvent under reduced pressure gave

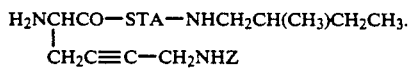

This was taken up in 15 ml DMF and 0.81 g (2.4 mmole) of di-(1-naphthylmethyl)acetic acid and 0.32 g (2.4 mmole) of HOBT added. The solution was cooled in ice and 0.49 g (2.4 mmole) of DCC added and the solution stirred at room temperature overnight. The mixture was filtered and the filtrate diluted with EtOAc and washed with H$_2$O, saturated NaHCO$_3$, and saturated NaCl. Drying and removal of the solvent under reduced pressure gave the crude product which was chromatographed on silica gel, eluting with EtOAc/hexane (1/1). There was obtained 0.2 g of product. The structure was confirmed by NMR and mass spectroscopy.

Calcd. for C$_{51}$H$_{60}$N$_4$O$_6$.0.33C$_4$H$_8$O$_2$ (MW 854.10): C, 73.57; H, 7.39; N, 6.56 Found C, 73.04; H, 7.36; N, 6.71.

EXAMPLE 30

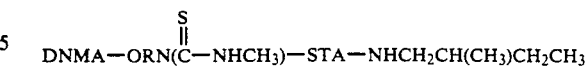

A solution of 0.47 g (0.7 mmole) of DNMA-ORN-STA-NHCH$_2$CH(CH$_3$)CH$_2$CH$_3$ in 30 ml CH$_2$Cl$_2$ was cooled to 0° and 51 mg (0.7 mmole) of methyl isothiocyanate added, and the solution allowed to stir at room temperature overnight. The solvent was then removed under reduced pressure and the residue chromatographed on silica gel, eluting with EtOAc. The material was transferred to a vial with the aid of CH$_2$Cl$_2$. There was obtained 0.3 g of product. The structure was confirmed by NMR and mass spectroscopy.

Calcd. for C$_{44}$H$_{59}$N$_5$O$_4$S.0.33C$_4$H$_8$O$_2$.0.25CH$_2$Cl$_2$ (MW 804.26): C, 68.05; H, 7.79; N, 8.71 Found C, 67.71; H, 7.80; N, 8.74.

EXAMPLE 31

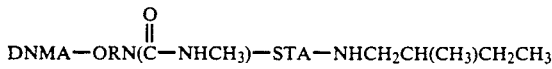

A solution of 0.47 g (0.7 mmole) of DNMA-ORN-STA-NHCH$_2$CH(CH$_3$)CH$_2$CH$_3$ in 30 ml CH$_2$Cl$_2$ was cooled in ice and 0.041 ml (0.7 mmole) of methyl isocyanate added and the solution allowed to stir at room temperature overnight. The solvent was removed under reduced pressure and the residue chromatographed on silica gel, eluting with EtOAc/MeOH (9/1). There was obtained 0.3 g of product. The structure was confirmed by NMR and mass spectroscopy.

Calcd. for C$_{44}$H$_{59}$N$_5$O$_5$.CH$_3$OH (MW 769.99): C, 70.19; H, 8.25; N, 9.10 Found C, 69.79; H, 8.06; N, 9.44.

EXAMPLE 32

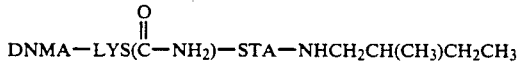

A solution of 0.3 g (0.4 mmole) of DNMA-LYS-STA-NHCH$_2$CH(CH$_3$)CH$_2$CH$_3$ in 15 ml dioxane was treated with 0.03 ml of HOAc followed by 30 mg (0.46 mmole) of NaOCN in 1 ml H$_2$O. The solution was warmed to 45° for four hours, cooled, and partitioned between EtOAc and saturated NaHCO$_3$. The EtOAc was washed with saturated NaCl, dried, and the solvent removed under reduced pressure giving the crude product which was chromatographed on silica gel, eluting with EtOAc, then EtOAc/MeOH (9/1). There was obtained 0.2 g of product, mp 134°-137°. The structure was confirmed by NMR and mass spectroscopy.

Calcd. for C$_{44}$H$_{59}$N$_5$O$_5$.CH$_3$OH (MW 769.99): C, 70.19; H, 8.25; N, 9.10 Found C, 70.27; H, 8.23; N, 9.15.

EXAMPLE 33

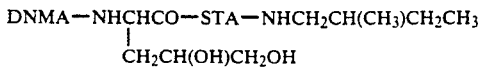

A solution of 350 mg (0.53 mmole) of

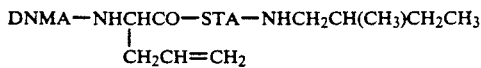

in 10 ml dioxane was treated with 8.1 ml (0.63 mmole) of a 2% solution of osmium tetroxide in dioxane. The solution was allowed to stir at room temperature for three days, then treated with hydrogen sulfide gas. The mixture was filtered and the solvent removed under reduced pressure. The residue was chromatographed on silica gel, eluting with CHCl₃/MeOH (97/3). The material was taken up in CHCl₃ and precipitated with hexane. There was obtained 131 mg of the product as a white solid. The structure was confirmed by NMR and mass spectroscopy.

Calcd. for $C_{42}H_{55}N_3O_6 \cdot 0.8H_2O$ (MW 712.30): C, 70.82; H, 8.01; N, 5.90 Found C, 70.91; H, 8.12; N, 5.81.

EXAMPLE 34

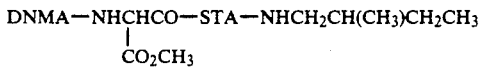

A solution of 1.80 g (5.29 mmole) di-(1-naphthylmethyl) acetic acid, 1.90 g (5.29 mmole) of

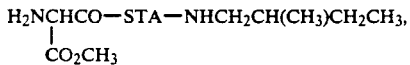

0.75 g (5.55 mmole) of HOBT, and 1.14 g (5.55 mmole) of DCC 50 ml DMF was stirred at 25° for six hours. The mixture was then filtered, and the solvent removed under high vacuum. The residue was taken up in EtOAc and washed with 1N citric acid, saturated NaCl, saturated NaHCO₃, and saturated NaCl. After drying, the solvent was evaporated under reduced pressure to a glass, 3.98 g. The product was chromatographed on silica gel, eluting with EtOAc. Combination of the appropriate fractions gave a solid, 2.18 g. The structure was confirmed by NMR, IR, and mass spectroscopy.

Calcd. for $C_{41}H_{51}N_3O_6 \cdot 0.33H_2O$ (MW 687.88): C, 71.59; H, 7.57; N, 6.11; H₂O, 0.87 Found C, 71.95; H, 7.61; N, 6.19; H₂O, 1.00.

EXAMPLE 35

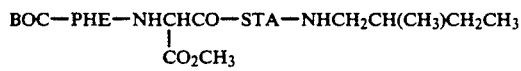

A solution of 4.37 g (16.5 mmole) of BOC-PHE, 5.92 g (16.5 mmole) of

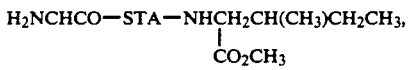

and 2.29 g (17.0 mmole) of HOBT in 150 ml DMF was cooled to 0°. 3.50 g (17 mmole) of DCC was added, and the mixture was stirred at 4° overnight. The mixture was filtered, and the solvent was removed under high vacuum. The residue was taken up in EtOAc and washed with 1N citric acid, saturated NaCl, saturated NaHCO₃, and saturated NaCl. After drying, the solution was evaporated under reduced pressure to an oil, which was chromatographed on silica gel, eluting with EtOAc. Combination of the appropriate fractions gave a white solid, 4.88 g. The structure was confirmed by NMR and mass spectroscopy.

Calcd. for $C_{31}H_{50}N_4O_8$ (MW 606.77): C, 61.36; H, 8.31; N, 9.23 Found C, 60.95; H, 8.23; N, 9.16.

EXAMPLE 36

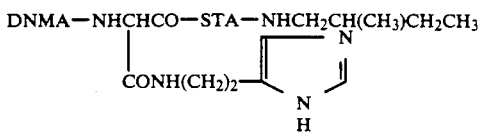

A solution of 0.96 g (1.44 mmole) of

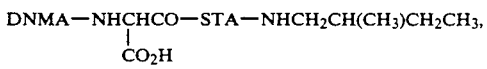

0.2 g (1.48 mmole) of HOBT, and 0.30 g (1.48 mmole) of DCC in 20 ml DMF was cooled to 0°. A solution of 0.27 g (1.48 mmole) of histamine.2HCl and 0.32 g (2.97 mmole) of Et₃N in 10 ml DMF was added. After stirring overnight at 4°, the mixture was filtered, and the solvent removed under high vacuum. The residue was taken up in EtOAc, filtered, and washed with 1N citric acid, saturated NaCl, saturated NaHCO₃, and saturated NaCl. After drying, the solvent was removed under reduced pressure and the residue was chromatographed on silica gel, eluting with a gradient of 2 to 10% MeOH in CHCl₃. Combination of the appropriate fractions gave the product as a foam, 0.89 g. The structure was confirmed by NMR and mass spectroscopy.

Calcd. for $C_{45}H_{56}N_6O_5 \cdot 0.25CHCl_3$ (MW 790.83): C, 68.72; H, 7.17; N, 10.62; Cl, 3.36 Found C, 68.39; H, 7.19; N, 10.60; Cl, 3.13.

EXAMPLE 37

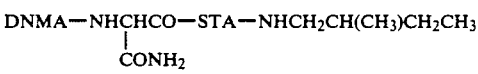

A solution of 0.6 g (0.88 mmole) of

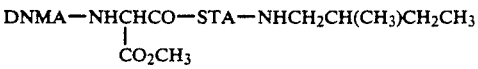

in 20 ml MeOH was cooled to −30° and saturated with NH₃ gas. The mixture was allowed to warm to room temperature over three hours, and the solvent was removed under reduced pressure. The residue was suspended in Et₂O, filtered, and the solvent evaporated. The residue was chromatographed on silica gel, eluting with CHCl₃/MeOH (98/2). The appropriate fractions were combined to give a solid, 0.35 g. The structure was confirmed by NMR and mass spectroscopy.

Calcd. for $C_{40}H_{50}N_4O_5 \cdot 0.125CHCl_3$ (MW 681.79): C, 70.69; H, 7.41; N, 8.22; Cl, 1.95 Found C, 70.75; H, 7.66; N, 8.27; Cl, 1.92.

EXAMPLE 38

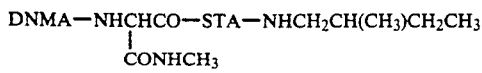

A solution of 0.6 g (0.88 mmole) of

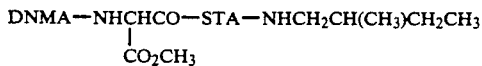

in 15 ml MeOH was cooled to −30° and saturated with liquid CH$_3$NH$_2$. After one hour, the solvent was removed in vacuo and the residue was chromatographed on silica gel, eluting with CHCl$_3$/MeOH (98/2). The appropriate fractions were combined to give a white foam, 0.50 g. The structure was confirmed by NMR and mass spectroscopy.

Calcd. for C$_{41}$H$_{52}$N$_4$O$_5$.0.08 CHCl$_3$ (MW 690.44): C, 71.46; H, 7.60; N, 8.11; Cl, 1.23 Found C, 71.09; H, 7.70; N, 8.15; Cl, 1.10.

EXAMPLE 39

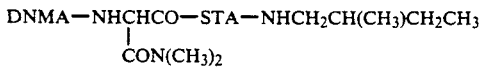

A solution of 0.92 g (1.35 mmole) of

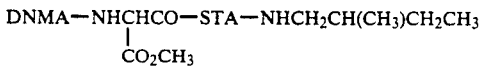

in 10 ml MeOH was saturated with liquid dimethylamine. After stirring for 3 hours, the solvent was removed under reduced pressure. The residue was chromatographed on silica gel, eluting with EtOAc. The appropriate fractions were combined to a solid, 0.41 g. The structure was confirmed by NMR and mass spectroscopy.

Calcd. for C$_{42}$H$_{54}$N$_4$O$_5$.0.6 H$_2$O (MW 705.73): C, 71.48; H, 7.88; N, 7.94; H$_2$O, 1.53 Found C, 71.17; H, 7.78; N, 7.73; H$_2$O, 1.18.

EXAMPLE 40

A solution of 0.55 g (1.62 mmole) of di-(1-naphthylmethyl)acetic acid, 0.69 g (1.62 mmole) of

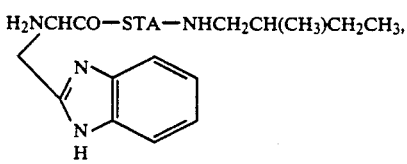

and 0.23 g (1.7 mmole) of HOBT in 20 ml DMF was treated with 0.35 g (1.7 mmole) of DCC and stirred at room temperature overnight. The mixture was filtered and the DMF removed under high vacuum. The residue was taken up in EtOAc and washed with 1N citric acid, saturated NaCl, saturated NaHCO$_3$, and saturated NaCl. Drying and removal of the solvent under reduced pressure gave the crude product which was chromatographed on silica gel, eluting with EtOAc. Combining the appropriate fractions gave material which was taken up in CH$_2$Cl$_2$ and precipitated by addition to Et$_2$O. The solid was collected to give 0.28 g of product. The structure was confirmed by NMR and mass spectroscopy.

Calcd. for C$_{47}$H$_{55}$N$_5$O$_4$ (MW 753.95): C, 74.87; H, 7.35; N, 9.29 Found C, 74.47; H, 7.35; N, 9.01.

EXAMPLE 41

DNMA-LYS(TOS)-STA-NHCH$_2$CH(CH$_3$)CH$_2$CH$_3$

A solution of 0.44 g (1.3 mmole) of di-(1-naphthylmethyl)acetic acid, 0.63 g (1.22 mmole) of LYS(TOS)-STA-NHCH$_2$CH(CH$_3$)CH$_2$CH$_3$, and 0.185 g (1.37 mmole) of HOBT in 35 ml of DMF was treated with 0.28 g (1.37 mmole) of DCC and the solution stirred at room temperature overnight. The mixture was filtered, and the solvent removed under high vacuum. The residue was taken up in EtOAc and washed with 1N citric acid, saturated NaCl, saturated NaHCO$_3$, and saturated NaCl. After drying, the solution was evaporated under reduced pressure and the residue chromatographed on silica gel, eluting with a gradient of 0 to 5% MeOH in CHCl$_3$. Combination of the appropriate fractions gave the product as a white foam, 0.99 g. The structure was confirmed by NMR and mass spectroscopy.

Calcd. for C$_{50}$H$_{64}$N$_4$O$_6$S.0.07CHCl$_3$ (MW 857.51): C, 70.13; H, 7.53; N, 6.53; Cl, 0.87 Found C, 69.78; H, 7.49; N, 6.40; Cl, 0.90.

EXAMPLE 42

DNMA-LYS(CO$_2$CH$_3$)-STA-NHCH$_2$CH(CH$_3$)CH$_2$CH$_3$

A solution of 0.124 g (0.7 mmole) of N-methyloxycarbonylsuccinimide and 0.50 g (0.72 mmole) of DNMA-LYS-STA-NHCH$_2$CH(CH$_3$)CH$_2$CH$_3$ in 2 ml DMF was stirred overnight at room temperature. The solvent was removed under high vacuum and the residue was taken up in EtOAc. The solution was washed with 1N citric acid, saturated NaCl, saturated NaHCO$_3$, and saturated NaCl. After drying, the solvent was removed under reduced pressure, and the residue triturated with EtO$_2$, giving the crude product as a solid. This was chromatographed on silica gel, eluting with a gradient of 0 to 1% MeOH in CHCl$_3$. The crude product was taken up in CHCl$_3$ and added to excess Et$_2$O giving a solid which was collected and dried. There was obtained 0.24 g of the product as a white solid. The structure was confirmed by NMR and mass spectroscopy.

Calcd. for C$_{45}$H$_{60}$N$_4$O$_6$ (MW 753.00): C, 71.77; H, 8.03; N, 7.44 Found C, 71.57; H, 8.07; N, 7.44.

EXAMPLE 43

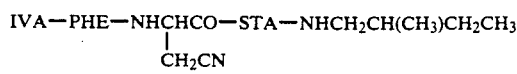

A solution of 0.92 g (3.7 mmole) of IVA-PHE and 0.53 g (3.89 mmole) of HOBT in 4 ml DMF and 30 ml CH$_2$Cl$_2$ was cooled to −5° and 0.8 g (3.89 mmole) of DCC added followed by 1.26 g (3.7 mmole) of

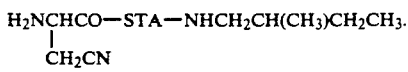
H₂NCHCO—STA—NHCH₂CH(CH₃)CH₂CH₃.
|
CH₂CN

The solution was stirred at room temperature overnight, filtered, and the solvent removed under reduced pressure. The residue was taken up in EtOAc and washed with 1N citric acid, saturated NaCl, saturated NaHCO₃, and saturated NaCl. The solution was dried, the volume reduced under reduced pressure, and the solution diluted with Et₂O. A precipitate formed which was collected giving the crude product. This was chromatographed on silica gel, eluting with CHCl₃/MeOH (98/2). The product was taken up in CHCl₃ and precipitated by the addition of Et₂O. There was obtained 1.04 g of product. The structure was confirmed by NMR and mass spectroscopy.

Calcd. for C₃₁H₄₉N₅O₅ (MW 571.74): C, 65.12; H, 8.64; N, 12.25 Found C, 65.00; H, 8.40; N, 12.21.

EXAMPLE 44

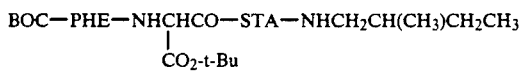
BOC—PHE—NHCHCO—STA—NHCH₂CH(CH₃)CH₂CH₃
|
CO₂-t-Bu

To a solution of 2.11 g (5 mmole) of

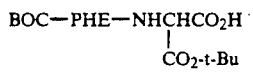
BOC—PHE—NHCHCO₂H
|
CO₂-t-Bu and 1.12 g (5.0 mmole) of STA-NHCH₂CH(CH₃)CH₂CH₃ in 155 ml CH₂Cl₂ was added a solution of 0.69 g (5.1 mmole) of HOBT in 8 ml DMF. The mixture was cooled to 0° and 1.05 g (5.1 mmole) of DCC was added. After warming to 25° overnight, the mixture was filtered and the solvent removed under reduced pressure. The residue was taken up in EtOAc and washed with 1N citric acid, saturated NaCl, saturated NaHCO₃, and saturated NaCl. Drying and removal of the solvent under reduced pressure gave the crude product which was chromatographed on silica gel, eluting with CHCl₃/EtOAc (50/50). Combining the appropriate fractions gave 3.34 g of the product as a white foam. The structure was confirmed by NMR and mass spectroscopy.

Calcd. for C₃₄H₅₆N₄O₈.0.6H₂O (MW 659.65): C, 61.91; H, 8.74; N, 8.49; H₂O, 1.64 Found C, 61.74; H, 8.56; N, 8.54; H₂O, 1.82.

EXAMPLE 45

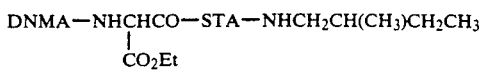
DNMA—NHCHCO—STA—NHCH₂CH(CH₃)CH₂CH₃
|
CO₂Et

To a solution of 2.29 g (4.88 mmole) of

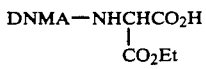
DNMA—NHCHCO₂H
|
CO₂Et and 1.09 g (4.88 mmole) of STA-NHCH₂CH(CH₃)CH₂CH₃ in 50 ml CH₂Cl₂ was added a solution of 0.68 g (5.02 mmole) of HOBT in 3 ml DMF. After cooling to 0°, 1.04 g (5.02 mmole) of DCC was added, and the mixture was stirred at room temperature overnight. The mixture was filtered, and the solvent removed under reduced pressure. The residue was taken up in Et₂O and washed with 1N citric acid, saturated NaCl, saturated NaHCO₃, and saturated NaCl. After drying, the solvent was removed under reduced pressure and the residue was chromatographed on silica gel, eluting with EtOAc/hexane (50/50). Combination of the appropriate fractions gave a solid, 2.33 g. The structure was confirmed by NMR and mass spectroscopy.

Calcd. for C₄₂H₅₃N₃O₆.0.4H₂O (MW 703.11): C, 71.75; H, 7.71; N, 5.98; H₂O, 1.02 Found C, 71.65; H, 7.63; N, 5.64; H₂O, 0.93.

EXAMPLE 46

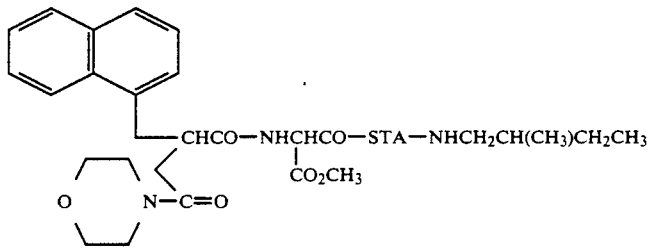

To a solution of 1.08 g (3.3 mmole) of

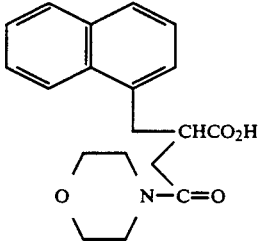

and 1.2 g (3.3 mmole) of

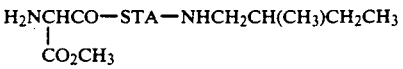
H₂NCHCO—STA—NHCH₂CH(CH₃)CH₂CH₃
|
CO₂CH₃ in 65 ml CH₂Cl₂ was added a solution of 0.46 g (3.4 mmole) of HOBT in 8 ml DMF. The mixture was cooled to 0° and 0.7 g (3.4 mmole) of DCC was added. After stirring overnight at room temperature, the mixture was filtered, and the solvent removed under reduced pressure. The residue was taken up in EtOAc and washed with 1N citric acid, saturated NaCl, saturated NaHCO₃, and saturated NaCl. After drying, the solvent was removed under reduced pressure and the residue was chromatographed on silica gel, eluting with EtOAc/CHCl₃/MeOH (45/45/10). Combination of the appropriate fractions gave a white foam, 1.18 g. The structure was confirmed by NMR and mass spectroscopy.

Calcd. for $C_{36}H_{52}N_4O_8 \cdot 1.0H_2O \cdot 0.0625CHCl_3$ (MW 695.28): C, 62.30; H, 7.85; N, 8.07; Cl, 0.96; H₂O, 2.59 Found C, 62.64; H, 7.86; N, 8.16; Cl, 1.03; H₂O, 2.76.

EXAMPLE 47

A solution of 0.4 g (1.0 mmole) of

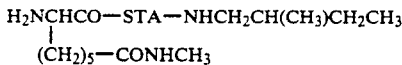

and 0.32 g (1.0 mmole) of di-(1-naphthylmethyl)acetic acid in 20 ml of CH₂Cl₂ was cooled in ice and 203 mg (2.0 mmole) of Et₃N added, followed by 280 mg (1.1 mmole) of bis(2-oxo-3-oxazolidinyl)phosphinic chloride. After stirring at room temperature overnight, the mixture was washed with 1N HCl, saturated NaHCO₃, and saturated NaCl. Drying and removal of the solvent under reduced pressure gave the crude product which was chromatographed on silica gel, eluting with EtOAc, then EtOAc/EtOH (1/1). There was obtained 0.46 g of product, mp 127°–131°.

EXAMPLE 48

DNMA-NHCH(CH₂CH₂CH₂CH=CH₂)CO-STA-LEU-NHCH₂Ph (ISOMER A)

To a solution of 4.9 g (10.4 mmole) of H₂NCH(CH₂CH₂CH₂CH=CH₂)CO-STA-LEU-NHCH₂Ph and 3.54 g (10.4 mmole) of di-(1-naphthylmethyl)acetic acid in 100 ml DMF was added 1.47 g (10.9 mmole) of HOBT followed by 2.25 g (10.9 mmole) of DCC. The mixture was stirred for fifteen hours at room temperature and the urea filtered off. The DMF was removed under reduced pressure and the residue taken up in EtOAc. The organic solution was washed with saturated NaHCO₃, dried, and concentrated under reduced pressure to afford the crude product. Chromatography on silica gel, eluting with a gradient of 0–2% MeOH in CHCl₃ gave 1.8 g of the desired product. The structure was confirmed by NMR spectroscopy.

Calcd. for $C_{52}H_{64}N_4O_5 \cdot 0.25CHCl_3$ (MW 854.91): C, 73.40; H, 7.58; N, 6.55 Found C, 73.09; H, 7.72; N, 6.79.

EXAMPLE 49

DNMA-NHCH(CH₂CH₂CH₂CH=CH₂)CO-STA-LEU-NHCH₂Ph (ISOMER B)

Continued elution from the chromatography column described in Example 48 gave 2.2 g of Isomer B, epimeric at the alpha carbon of the 5-pentenyl amino acid. The structure was confirmed by NMR spectroscopy.

Calcd. for $C_{52}H_{64}N_4O_5$ (MW 825.06): C, 75.69; H, 7.82; N, 6.79 Found C, 75.52; H, 8.04; N, 6.75.

EXAMPLE 50

To a solution of 1.55 g (1.88 mmole) of DNMA-NHCH(CH₂₂CH₂CH=CH₂)CO-STA-LEU-NHCH₂Ph (Isomer A) in 20 ml of CH₂Cl₂ was added 0.486 g (2.82 mmole) of m-chloroperbenzoic acid. The solution was stirred for twelve hours, diluted with EtOAc, washed with saturated NaHCO₃, dried, and concentrated under reduced pressure to give the crude product. Chromatography on silica gel, eluting with a gradient of 0–2% MeOH in CHCl₃ gave the pure product. The structure was confirmed by NMR spectroscopy.

Calcd. for $C_{52}H_{64}N_4O_6$ (MW 841.06): C, 74.25; H, 7.67; N, 6.66 Found C, 74.07; H, 7.78; N, 6.45.

EXAMPLE 51

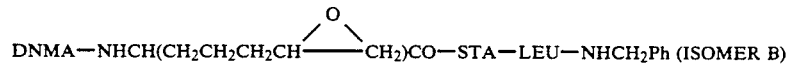

In a manner similar to Example 50, 2.2 g. (2.67 mmole) of DNMA-NHCH(CH₂CH₂CH₂CH=CH₂)CO-STA-LEU-NHCH₂Ph (Isomer B) gave 1.5 g of product. The structure was confirmed by NMR spectroscopy.

Cacld. for $C_{52}H_{64}N_4O_6$ (MW 841.06): C, 74.25; H, 7.67; N, 6.66 Found C, 74.21; H, 7.57; N, 6.62.

EXAMPLE 52

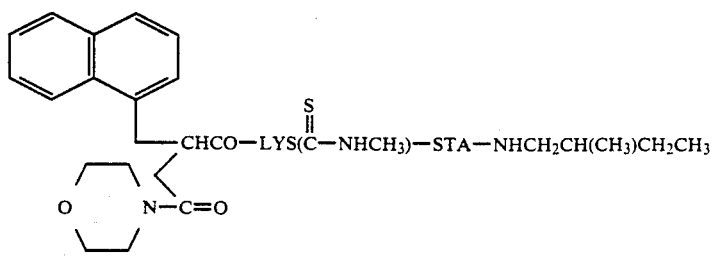

Following the procedure of Example 2, but using
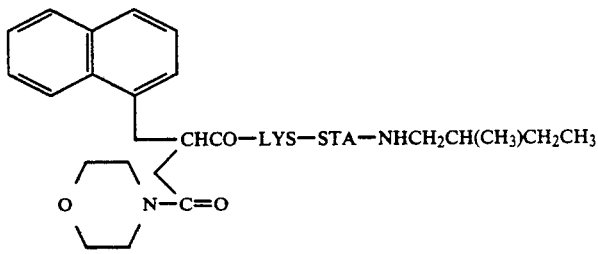
gives the title compound.
EXAMPLE 53
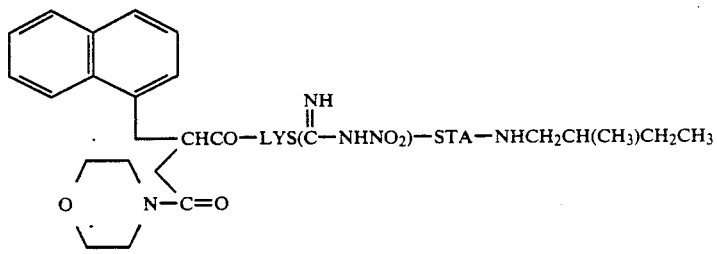
Following the procedure of Example 9, but using
Following the procedure of Example 13, but using
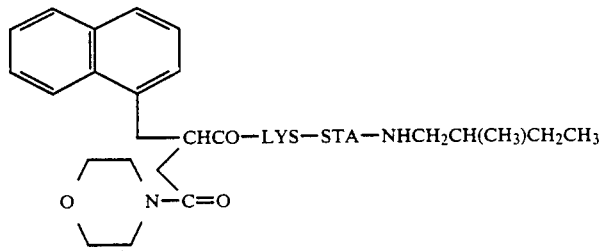
gives the title compound.
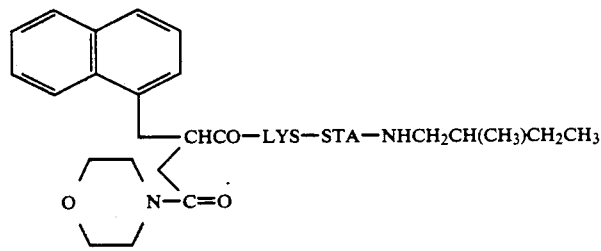
gives the title compound.
EXAMPLE 54
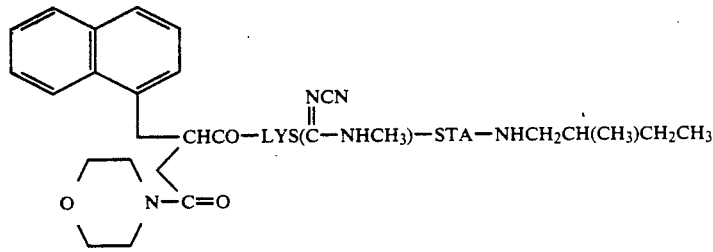

EXAMPLE 55

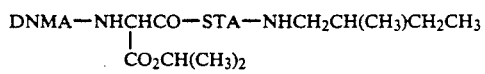

Following the procedure of Example 45, but substituting

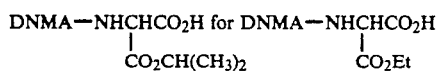

gave the title compound as a solid foam. The structure was confirmed by NMR and mass spectroscopy.

Calcd. for $C_{43}H_{55}N_3O_6 \cdot 0.25H_2O \cdot 0.03CHCl_3$ (MW 718.02): C, 71.98; H, 7.80; N, 5.85; $H_2O$, 0.63; Cl, 0.44 Found C, 72.10; H, 7.66; N, 5.66; $H_2O$, 0.69; Cl, 0.57.

EXAMPLES 56 AND 57

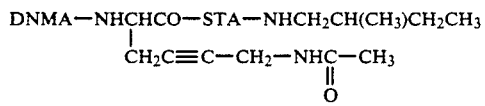

A solution of 1.7 g (3.4 mmole) of

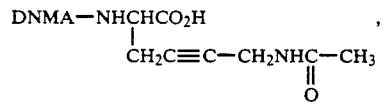, 454 mg (3.4 mmole)

of HOBT, and 821 mg (3.4 mmole) of STA-NHCH$_2$CH(CH$_3$)CH$_2$CH$_3$ in 25 ml of DMF was cooled in ice and treated with a solution of 700 mg (3.4 mmole) of DCC in 10 ml of DMF. After 0.5 hour at 0°, the mixture was allowed to stir at room temperature overnight. The mixture was filtered and the solvent was removed under reduced pressure. Adding EtOAc to the residue caused the less soluble isomer to precipitate. It was collected and washed with EtOAc to give 1.58 g of the product (Isomer A), mp 164°–166°. The structure was confirmed by NMR and mass spectroscopy.

Calcd. for $C_{45}H_{56}N_4O_5 \cdot 0.1$ CHCl$_3$ (MW 744.87): C, 72.72; H, 7.59; N, 7.52 Found C, 72.74; H, 7.78; N, 7.76.

The filtrate from filtering off the less soluble isomer was washed with 1N HCl, H$_2$O, saturated NaHCO$_3$, and saturated NaCl. Drying and removal of the solvent under reduced pressure left 1.72 g of a yellow foam. Chromatography on silica gel, eluting with CHCl$_3$/MeOH (95/5) gave 1.7 g of a foam. Dissolving in CHCl$_3$ and gradually adding hexane caused the more soluble isomer to precipitate. It was collected and washed with hexane to give 1.24 g of Isomer B, mp 147°–155°. The structure was confirmed by NMR and mass spectroscopy.

Calcd. for $C_{45}H_{56}N_4O_5 \cdot 0.05$ CHCl$_3$ (MW 739.01): C, 73.22; H, 7.65; N, 7.58 Found C, 73.12; H, 7.82; N, 7.67.

EXAMPLE 58

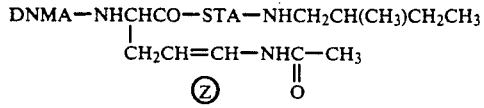

A solution of 430 mg of Isomer A (Example 56) in 70 ml MeOH and 5 ml pyridine was treated with 0.04 g 5% Pd/CaCO$_3$ and shaken under an atmosphere of hydrogen until the calculated amount of hydrogen was taken up. The mixture was then filtered and the solvent removed under reduced pressure. The residue was taken up in EtOAc and washed twice with 1N HCl, then H$_2$O, saturated NaHCO$_3$, and saturated NaCl. On concentrating the EtOAc, a solid started to precipitate. Addition of hexane and filtration gave 203 mg of the completely reduced side product. Stripping the filtrate to dryness and trituration with hexane gave 78 mg of the unsaturated product. The structure was confirmed by NMR and mass spectroscopy.

Calcd. for $C_{45}H_{58}N_4O_5 \cdot 0.5$ CH$_3$OH (MW 750.97): C, 72.77; H, 8.05; N, 7.46 Found C, 72.41; H, 8.38; N, 8.00.

EXAMPLE 59

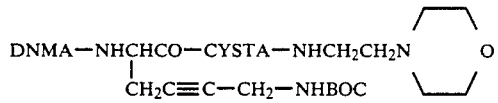

A solution of 5.0 g (8.9 mmole) of

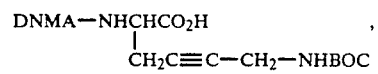, 1.2 g (8.9 mmole) of HOBT, and 2.9 g (8.9 mmole) of

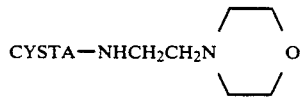

in 50 ml DMF was cooled in ice and treated with a solution of 1.89 g (8.9 mmole) of DCC in 10 ml of DMF. After 0.5 hour at 0°, the mixture was allowed to stir at room temperature for four days. The mixture was filtered and the solvent removed under high vacuum. The residue was taken up in EtOAc, filtered, and washed with saturated NaHCO$_3$, then saturated NaCl. Drying over MgSO$_4$ and removal of the solvent under reduced pressure gave the crude product which was purified by chromatography on silica gel, eluting with CHCl$_3$/MeOH (97/3). There was obtained 4.5 g of product. The structure was confirmed by NMR and mass spectroscopy.

Calcd. for $C_{52}H_{67}N_5O_7 \cdot 0.75$ CHCl$_3$ (MW 963.64): C, 65.74; H, 7.09; N, 7.27 Found C, 65.75; H, 7.11; N, 7.15.

EXAMPLE 60

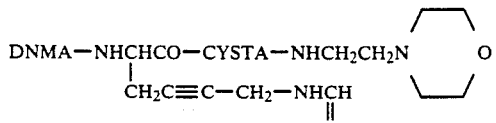

A solution of 749 mg (0.97 mmole) of

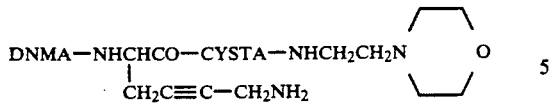

in 10 ml of CH$_2$Cl$_2$ was cooled in ice and 0.1 ml (1.02 mmole) of formic-acetic anhydride added, followed by 0.2 ml (1.02 mmole) of Et$_3$N. After 15 minutes at 0°, the solution was allowed to stir at room temperature overnight. The solvent was removed under reduced pressure and the residue taken up in EtOAc. This was washed with saturated NaHCO$_3$, saturated NaCl, then dried and the solvent removed under reduced pressure leaving the crude product. Chromatography on silica gel, eluting with CHCl$_3$/MeOH (93/7) gave 0.67 g of product. The structure was confirmed by NMR and mass spectroscopy.

Dissolving in a small amount of EtOH, adding the required amount of 1N citric acid, diluting with H$_2$O, and freeze-drying gave the product as the citrate salt.

Calcd for C$_{48}$H$_{59}$N$_5$O$_6$·C$_6$H$_8$O$_7$·1.5 H$_2$O·0.2 CHCl$_3$ (MW 1045.02): C, 62.29; H, 6.77; N, 6.70; Cl, 2.04 Found C, 62.19; H, 6.55; N, 6.18; Cl, 1.80.

EXAMPLE 61

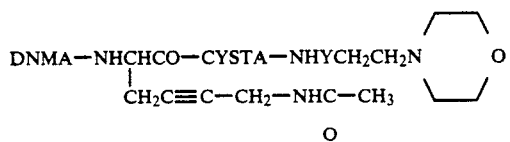

A solution of 840 mg (1.08 mmole) of

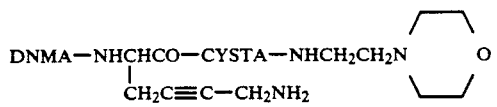

in 20 ml of CH$_2$Cl$_2$ was cooled in ice and 135 mg (1.19 mmole) of 1-acetylimidazole added followed by 0.3 ml (2.3 mmole) of Et$_3$N. After stirring at room temperature overnight, the solvent was removed under reduced pressure and the residue taken up in EtOAc. The EtOAc was washed with saturated NaHCO$_3$, H$_2$O, then saturated NaCl. Drying and removal of the solvent under reduced pressure gave the crude product which was purified by chromatography on silica gel, eluting with CHCl$_3$/MeOH (95/5). There was obtained 0.76 g of product. The structure was confirmed by NMR and mass spectroscopy.

Dissolving in a small amount of EtOH, adding the required amount of 1N citric acid, diluting with H$_2$O, and freeze-drying gave the product as the citrate salt.

Calcd. for C$_{49}$H$_{61}$N$_5$O$_6$·C$_6$H$_8$O$_7$·2.2 H$_2$O (MW 1047.78): C, 63.04; H, 7.06; N, 6.68 Found C, 63.04; H, 6.95; N, 6.35.

EXAMPLE 62

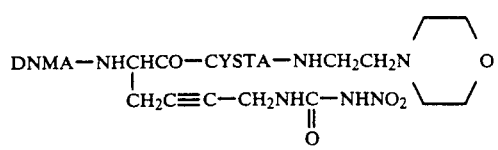

A solution of 900 mg (1.16 mmole) of

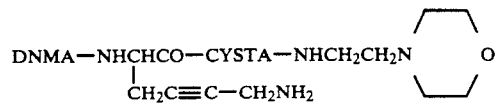

in 20 ml of ab. EtOH was treated with 181 mg (1.34 mmole) of 2-methyl-1-nitro-2-thiopseudourea followed by 0.33 ml (2.3 mmole) of Et$_3$N. After stirring at room temperature for four days, the solvent was removed under reduced pressure and the residue taken up in EtOAc. The EtOAc was washed with saturated NaHCO$_3$, H$_2$O, and saturated NaCl. Drying and removal of the solvent under reduced pressure gave the crude product which was purified by chromatography on silica gel, eluting with CHCl$_3$/MeOH (95/5). There was obtained 0.78 g of the product. The structure was confirmed by NMR and mass spectroscopy.

Dissolving in a small amount of EtOH, adding the required amount of 1N citric acid, diluting with H$_2$O, and freeze-drying gave the product as the citrate salt.

Calcd. for C$_{48}$H$_{60}$N$_8$O$_7$·C$_6$H$_8$O$_7$·0.2 CHCl$_3$ (MW 1077.03): C, 60.44; H, 6.38; N, 10.40; Cl, 1.98 Found C, 60.44; H, 6.43; N, 10.17; Cl, 2.00.

EXAMPLE 63

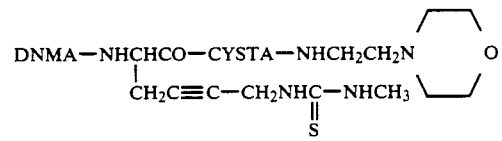

A solution of 900 mg (1.16 mmole) of

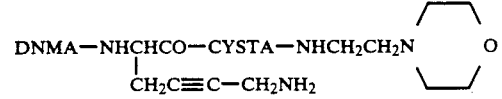

in 20 ml CHCl$_3$ was treated with 87 mg (1.16 mmole) of methyl isothiocyanate followed 0.3 ml (2.3 mmole) of Et$_3$N, and the solution stirred at room temperature for two days. The solvent was removed under reduced pressure and the residue taken up in EtOAc. The EtOAc was washed with saturated NaHCO$_3$, H$_2$O, and saturated NaCl. Drying and removal of the solvent under reduced pressure gave the crude product which was chromatographed on silica gel, eluting with CHCl$_3$/MeOH (95/5). There was obtained 0.59 g of the product. The structure was confirmed by NMR and mass spectroscopy.

Dissolving in a small amount of EtOH, adding the required amount of 1N citric acid, and diluting with H$_2$O caused the citrate salt to form a milky suspension. Freeze-drying the suspension gave the citrate salt.

Calcd. for C$_{49}$H$_{62}$N$_6$O$_5$S.C$_6$H$_8$O$_7$.3.0 H$_2$O.0.2 CHCl$_3$ (MW 1117.08): C, 59.35; H, 6.88; N, 7.52; Cl, 1.90 Found C, 59.37; H, 6.64; N, 7.36; Cl, 1.68.

EXAMPLE 64

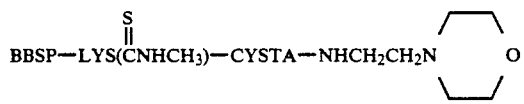

A solution of 1.34 g (2.23 mmole) of

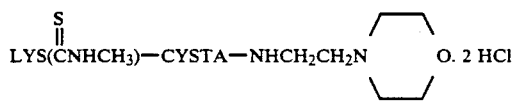

in 50 ml DMF was cooled in ice and 0.63 ml (4.46 mmole) of Et$_3$N added, followed by 0.63 g (2.23 mmole) of (+)-2-benzyl-3-(t-butylsulfonyl)propionic acid, 0.3 g (2.23 mmole) of HOBT, and 0.46 g (2.23 mmole) of DCC. The solution was stirred at room temperature for 48 hours, filtered, and the solvent removed under high vacuum. The residue was taken up in EtOAc and washed with saturated NaHCO$_3$, then brine. Drying and removal of the solvent under reduced pressure gave the crude product which was chromatographed on silica gel, eluting with a gradient of 2-8% MeOH in CHCl$_3$. There was obtained 1.08 g of the product as a white foam. The structure was confirmed by NMR and mass spectroscopy.

The product was converted to the citrate salt.

Calcd. for C$_{39}$H$_{66}$N$_6$O$_7$S$_2$.C$_6$H$_8$O$_7$.1.56 H$_2$O (MW 1015.31): C, 53.23; H, 7.60; N, 8.28 Found C, 53.22; H, 7.71; N, 8.05.

EXAMPLE 65

A solution of 2.0 g (2.88 mmole) of DNMA-LYS-STA-NHCH$_2$CH(CH$_3$)CH$_2$CH$_3$, 0.39 g (2.88 mmole) of methylmercaptoacetic acid, and 0.44 g (3.16 mmole) of HOBT in 20 ml DMF was cooled in ice and treated with 0.66 g (3.16 mmole) of DCC. After 0.5 hour at 0°, the mixture was stirred at room temperature for 18 hours. The mixture was filtered and the solvent removed under high vacuum. The residue was taken up in EtOAc and washed with saturated NaHCO$_3$, then saturated NaCl. Drying and removal of the solvent under reduced pressure gave the crude product which was chromatographed on silica gel, eluting with CHCl$_3$/MeOH (98/2). There was obtained 1.7 g of product. The structure was confirmed by NMR and mass spectroscopy.

Calcd. for C$_{46}$H$_{62}$N$_4$O$_5$S.0.17 CHCl$_3$.0.18 H$_2$O (MW 806.53): C, 68.75; H, 7.82; N, 6.95; Cl, 2.24 Found C, 68.05; H, 8.03; N, 6.99; Cl, 2.30.

EXAMPLE 66

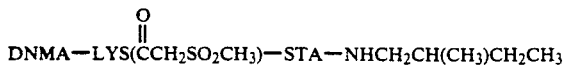

To a cold solution of 1.24 g (1.58 mmole) of

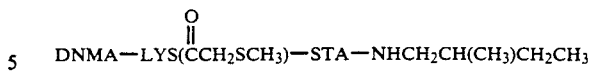

in 30 ml CHCl$_3$ was added 0.47 g (2.45 mmole) of m-chloroperbenzoic acid and the solution stirred at room temperature overnight. The solution was then washed with saturated NaHCO and saturated NaCl. Drying and removal of the solvent under reduced pressure gave the crude material which was purified by chromatography on silica gel, eluting with a gradient of 2-5% MeOH in CHCl$_3$. There was obtained 0.4 g of the product. The structure was confirmed by NMR and mass spectroscopy.

Calcd. for C$_{46}$H$_{62}$N$_4$O$_7$S.0.3 CHCl$_3$ (MW 850.91): C, 65.35; H, 7.38; N, 6.58 Found C, 65.30; H, 7.39; N, 6.39.

EXAMPLE 67

Continued elution from the chromatography column from Example 66 gave 0.5 g of the sulfoxide. The structure was confirmed by NMR and mass spectroscopy.

Calcd. for C$_{46}$H$_{62}$H$_4$O$_6$S.0.45 CHCl$_3$ (MW 852.77): C, 65.42; H, 7.38; N, 6.57 Found C, 65.61; H, 7.54; N, 6.53.

EXAMPLE 68

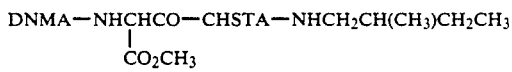

A solution of 0.91 g (2 mmole) of

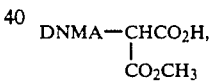

0.55 g(2 mmole) of CHSTA—NHCH$_2$CH(CH$_3$)CH$_2$CH$_3$, and 0.28 g (2 mmole) of HOBT in 20 ml CH$_2$Cl$_2$ was cooled in ice and treated with a solution of 0.42 g (2 mmole) of DCC in 5 ml CH$_2$Cl$_2$. The mixture was stirred at room temperature for 24 hours and filtered. The filtrate was diluted with CH$_2$Cl$_2$ and washed with H$_2$O, saturated NaHCO$_3$, and brine. After drying and removal of the solvent under reduced pressure, the residue was chromatographed on silica gel, eluting with CHCl$_3$/MeOH (95/5). There was obtained 0.4 g of product. The structure was confirmed by NMR and mass spectroscopy.

Calcd. for C$_{43}$H$_{53}$N$_3$O$_6$.0.6 H$_2$O (MW 716.6): C, 71.88; H, 7.38; N, 5.85 Found C, 71.54; H, 7.60; N, 6.13.

EXAMPLE 69

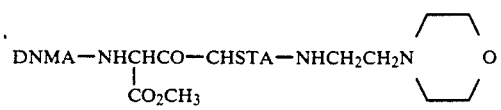

Following the same procedure as for Example 68 but replacing

CHSTA—NHCH₂CH(CH₃)CH₂CH₃ with

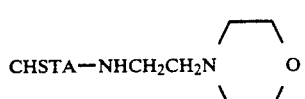

gave the title compound. The structure was confirmed by NMR and mass spectroscopy.

Calcd. for C₄₄H₅₄N₄O₇·0.6 H₂O (MW 761.1): C, 69.37; H, 7.25; N, 7.35 Found C, 69.12; H, 7.46; N, 7.30.

EXAMPLE 70

A solution of 1.7 g (2.36 mmole) of DNMA-LYS-CHSTA-NHCH₂CH(CH₃)CH₂CH₃ in 40 ml of CHCl₃ was cooled in ice and 1.26 g (12 mmole) of Et₃N added followed by 0.17 g (2.36 mmole) of methyl isothiocyanate. After stirring at room temperature for 18 hours, the solvent was removed under reduced pressure and the residue chromatographed on silica gel, eluting with EtOAc/MeOH (95/5). There was obtained 0.8 g of product. The structure was confirmed by NMR and mass spectroscopy.

Calcd. for C₄₇H₆₃N₅O₄S (MW 794.01): C, 71.12; H, 8.03; N, 8.83 Found C, 70.96; H, 8.15; N, 8.87.

EXAMPLE 71

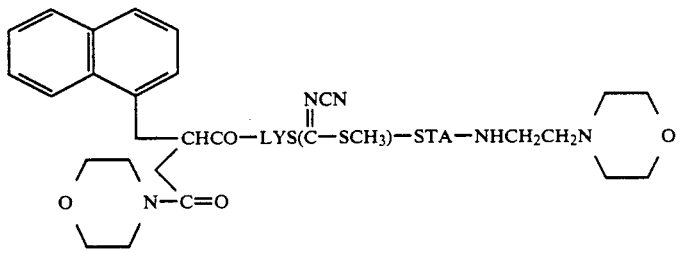

A solution of 0.59 g (0.81 mmole) of

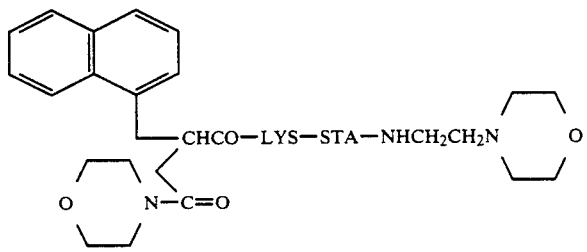

in 40 ml of CH₂Cl₂ was treated with 0.14 g (0.85 mmole) of dimethyl N-cyanodithioiminocarbonate and 0.58 ml (3.26 mmole) of diisopropylethylamine and stirred at room temperature for two days. The solvent was removed under reduced pressure and the residue was taken up in CHCl₃ and washed with saturated NaHCO₃. Drying and removal of the solvent under reduced pressure gave the crude product. Chromatography on silica gel, eluting with CHCl₃/MeOH (9/1) gave 0.52 g of the product as a foam. The structure was confirmed by NMR and mass spectroscopy.

Calcd. for C₄₂H₆₂N₈O₇S·1.0 CHCl₃ (MW 942.43): C, 54.79; H, 6.73; N, 11.89; S, 3.40 Found C, 54.42; H, 6.58; N, 11.74; S, 3.67.

EXAMPLE 72

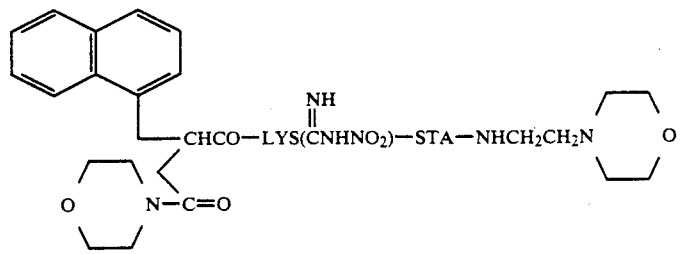

A solution of 1.2 g (1.66 mmole) of

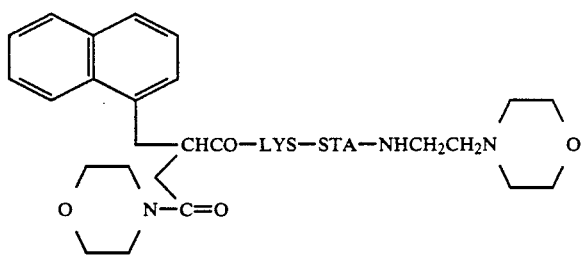

in 45 ml of EtOH was treated with 0.96 ml (5.46 mmole) of diisopropylethylamine and 0.235 g (1.74 mmole) of 2-methyl-1-nitro-2-thiopseudourea and stirred at room temperatures for three days. The solvent was then removed under reduced pressure and the residue chromatographed on silica gel, eluting with CHCl₃/MeOH (9/1). The appropriate fractions were combined, the product taken up in CHCl₃/EtOAc and washed with saturated NaHCO₃. Drying and removal of the solvent under reduced pressure gave 1.19 g of the product. The structure was confirmed by NMR and mass spectroscopy.

Calcd. for $C_{40}H_{61}N_9O_9 \cdot 2\ H_2O$ (MW 847.99): C, 56.65; H, 7.72; N, 14.87 Found C, 56.69; H, 7.82; N, 13.81.

EXAMPLE 73

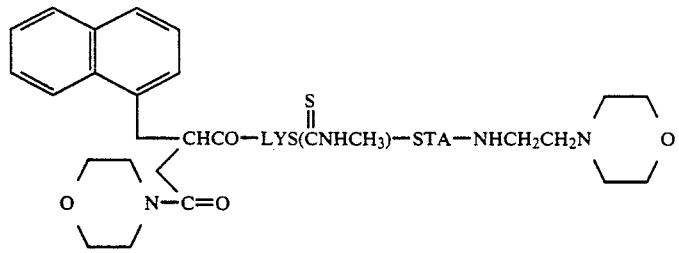

A cold solution of 1.2 g (1.66 mmole) of

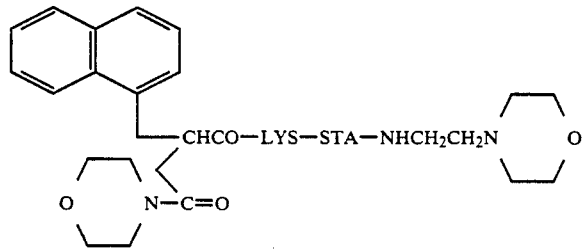

in 40 ml CH₂Cl₂ was treated with 1.18 ml (6.62 mmole) of diisopropylethylamine and 0.145 g (1.99 mmole) of methyl isothiocyanate. After two hours at 0°, the solution was allowed to stir at room temperature for two days. Removal of the solvent under reduced pressure gave the crude product which was chromatographed on silica gel, eluting with a gradient of 5–10% MeOH in CHCl₃. There was obtained 1.26 g of product as a foam. The structure was confirmed by NMR and mass spectroscopy.

Calcd. for $C_{41}H_{63}N_7O_7S \cdot 1.0\ CHCl_3$ (MW 917.41): C, 54.98; H, 7.03; N, 10.69 Found C, 54.78; H, 6.90; N, 10.59.

EXAMPLE 74

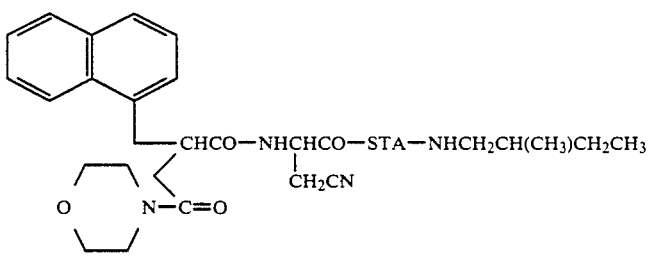

A solution of 0.982 g (3.0 mmole) of

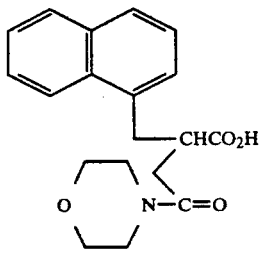

in 15 ml DMF was cooled in ice and treated successively with 419 mg (3.1 mmole) of HOBT, 640 mg (3.1 mmole) of DCC and 1.05 g (3.1 mmole) of

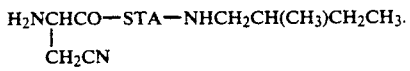
H₂NCHCO—STA—NHCH₂CH(CH₃)CH₂CH₃.
|
CH₂CN

The solution was kept at 0° for one hour, then stirred at room temperature overnight. The mixture was filtered and the solvent removed under high vacuum. The residue was taken up in EtOAc and washed with 1N citric acid, saturated NaHCO₃, and brine. Drying and removal of the solvent under reduced pressure gave the crude product which was purified by chromatography on silica gel, eluting with CHCl₃/MeOH (95/5). There was obtained 1.25 g of product. The structure was confirmed by NMR and mass spectroscopy.

Calcd. for $C_{36}H_{51}N_5O_6.0.4$ CHCl₃ (MW 697.57): C, 62.66; H, 7.43; N, 10.04 Found C, 62.49; H, 7.54; N, 10.16.

EXAMPLE 75

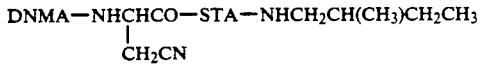
DNMA—NHCHCO—STA—NHCH₂CH(CH₃)CH₂CH₃
|
CH₂CN

Using the procedure of Example 74 and substituting 1-naphthylmethyl)acetic acid for

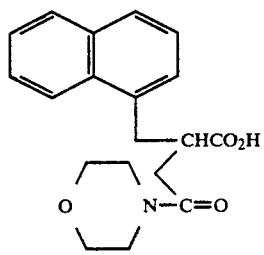

gave the title compound. The structure was confirmed by NMR and mass spectroscopy.

Calcd. for $C_{41}H_{50}N_4O_4.0.6$ H₂O (MW 673.65): C, 73.09; H, 7.66; N, 8.32 Found C, 73.08; H, 7.63; N, 8.45.

EXAMPLES 76 AND 77

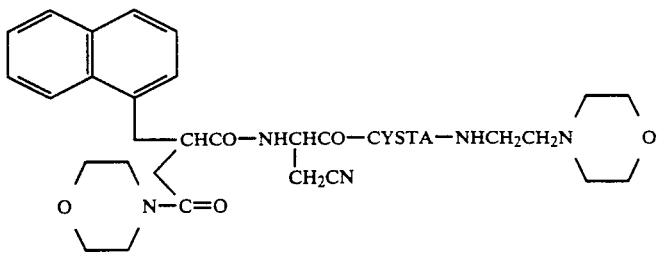

A solution of 1.31 g (4.0 mmole) of

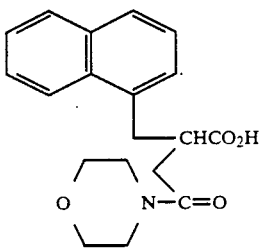

in 20 ml DMF was Cooled iD ice and treated successively with 542 mg (4.0 mmole) of HOBT, 825 mg (4.0 mmole) of DCC and then with a solution of 1.7 g (4.0 mmole) of

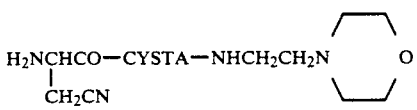
H₂NCHCO—CYSTA—NHCH₂CH₂N   O
|
CH₂CN in 15 ml DMF. After 1.5 hours at 0°, the solution was stirred at room temperature overnight. The mixture was then filtered, and the DMF removed under high vacuum. The residue was taken up in EtOAc and washed with saturated NaHCO₃, H₂O, then brine. Drying and removal of the solvent under reduced pressure left the crude product. Chromatography on silica gel, eluting with CHCl₃/MeOH (95/5) gave the fast moving diastereomer. The structure was confirmed by NMR and mass spectroscopy. The material was converted to the citrate salt in water and then freeze-dried.

Calcd. for $C_{40}H_{56}N_6O_7.C_6H_8O_7.0.5$ H₂O (MW 934.04): C, 59.15; H, 7.01; N, 9.00 Found C, 58.97; H, 7.08; N, 9.33.

Continued elution from the column gave the slow eluting diastereomer. The structure was confirmed by NMR and mass spectroscopy. The material was converted to the citrate salt in H₂O and freeze-dried.

Calcd. for $C_{40}H_{56}N_6O_7.C_6H_8O_7.2.2$ H₂O (MW 964.67): C, 57.27; H, 7.15; N. 8.71 Found C, 57.16; H, 6.78; N, 8.88.

EXAMPLE 78

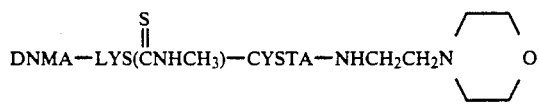

A solution of 1.8 g of di-(1-naphthylmethyl)acetic acid, 0.5 g HOBT, and 0.76 g DCC in 25 ml DMF was stirred at room temperature for 15 minutes. To this was then added a solution of 1.93 g

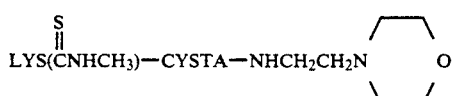

in 10 ml CH$_2$Cl$_2$ and the mixture stirred for two days. The mixture was then filtered and the fitrate evaporated in vacuo. The residue was taken up in CH$_2$Cl$_2$ and washed with 5% K$_2$CO$_3$. Drying and removal of the solvent under reduced pressure gave the crude product which was purified by chromatography on silica gel, eluting with CHCl$_3$/MeOH (97/3). The structure was confirmed by mass spectroscopy.

EXAMPLE 79

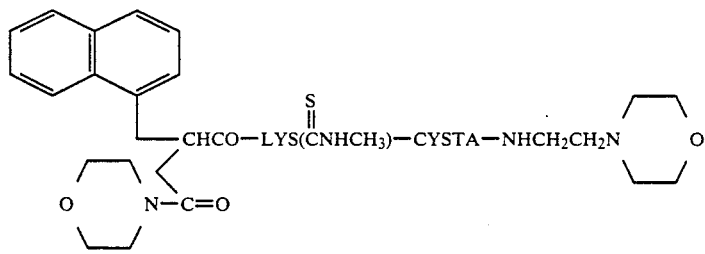

Using the procedure for Example 78 and substituting

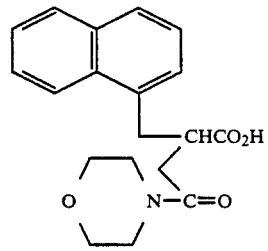

for di-(1-naphthylmethyl)acetic acid gave the title compound. The structure was confirmed by mass spectroscopy.

EXAMPLE 80

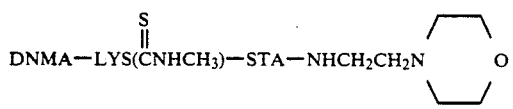

A solution of 0.39 g (0.52 mmole) of

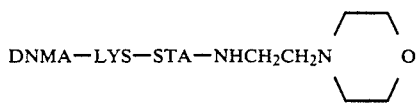

in 15 ml CH$_2$Cl$_2$ at 0° was treated with a solution of 38 mg (0.52 mmole) of methyl isothiocyanate and the solution stirred at room temperature overnight. The solvent was evaporated and the crude product chromatographed on silica gel, eluting with a gradient of 3–10% MeOH in CHCl$_3$. The appropriate fractions were combined to give 0.3 g of the product as a white foam. The structure was confirmed by NMR and mass spectroscopy.

Calcd. for C$_{46}$H$_{62}$N$_6$O$_5$S.0.3 CHCl$_3$ (MW 846.92): C, 64.89; H, 7.32; N, 9.79; S, 3.73 Found C, 64.82; H, 7.43; N, 9.56; S, 3.52.

EXAMPLE 81

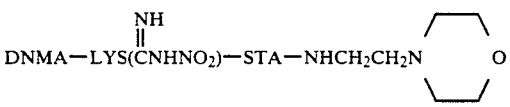

To a solution of 1.5 g (2.0 mmole) of DNMA-LYS-STA-

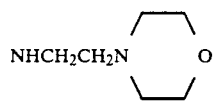

in 50 ml EtOH was added 305 mg (2.2 mmole) of 2-methyl-1-nitro-2-thiopseudourea and the mixture stirred at room temperature for 72 hours. The solvent was evaporated and the residue chromatographed on silica gel using a gradient elution of 5–12% MeOH in CHCl$_3$. The appropriate fractions were combined to give 0.82 g of a white foam. The structure was confirmed by NMR and mass spectroscopy.

Calcd. for C$_{45}$H$_{60}$O$_7$N$_8$.0.4 CHCl$_3$ (MW 872.78): C, 62.47; H, 6.98; N, 12.84; Cl, 5.47 Found C, 62.44; H, 7.12; N, 12.83; Cl, 5.14.

EXAMPLE 82

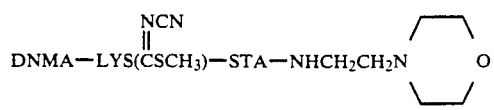

To a solution of 1.26 g (1.71 mmole) of

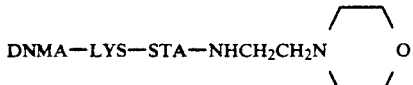

in 50 ml CHCl$_3$ was added 277 mg (1.71 mmole) of dimethyl N-cyanodithioiminocarbonate and the solution stirred at room temperature for 24 hours. Since the reaction was not yet complete, 0.2 ml (0.85 mmole) of Et$_3$N was added and the stirring continued for an additional 24 hours. The solvent was evaporated and the residue chromatographed on silica gel, eluting with a gradient 5–12% MeOH in CHCl$_3$. The appropriate fractions were combined to give a white foam, 0.55 g. The structure was confirmed by NMR and mass spectroscopy.

Calcd. for C$_{47}$H$_{61}$N$_7$O$_5$S.0.5 CHCl$_3$ (MW 895.80): C, 63.69; H, 6.92; N, 10.95; S, 3.58; Cl, 6.66 Found C, 63.70; H, 6.98; N, 10.65; S, 4.61; Cl, 7.86.

EXAMPLE 83

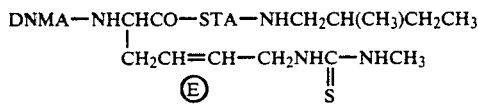

A solution of 1.0 g (1.37 mmole) of

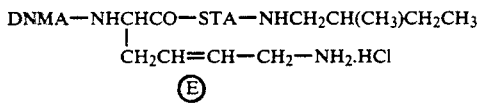

in 10 ml CH$_2$Cl$_2$ was cooled to $-10°$ with 0.21 ml (1.51 mmole) of Et$_3$N followed by a solution of 0.1 g (1.37 mmole) of methyl isothiocyanate in 5 ml CH$_2$Cl$_2$. After stirring at room temperature overnight the solvent was evaporated and the residue taken up in EtOAc. The EtOAc was washed with H$_2$O then brine. Drying and removal of the solvent under reduced pressure gave the crude product which was chromatographed on silica gel, eluting with CHCl$_3$/MeOH (98/2). There was obtained 0.45 g of product as a white foam. The structure was confirmed by NMR and mass spectroscopy.

Calcd. for C$_{45}$H$_{59}$N$_5$OS.0.07 CHCl$_3$ (MW 774.42): C, 69.90; H, 7.69; N, 9.04; S, 4.14 Found C, 69.92; H, 7.81; N, 8.66; S, 4.23.

EXAMPLE 84

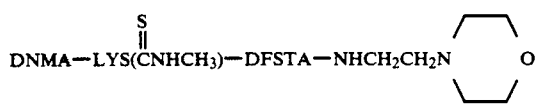

A solution of 1.03 g (1.33 mmole) of

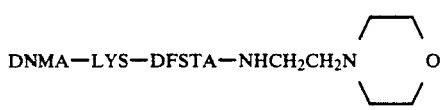

in 20 ml CH$_2$Cl$_2$ at 0° was treated with 107 mg (1.46 mmole) of methyl isothiocyanate in 5 ml of CH$_2$Cl$_2$ and the solution stirred at room temperature overnight. 0.1 ml (0.67 mmole) of Et$_3$N was then added and the solution stirred for an additional 24 hours. The solvent was removed under reduced pressure and the residue chromatographed on silica gel, eluting with a gradient of 5–8% MeOH in CHCl$_3$. There was obtained 0.62 g of the product as a white foam. The structure was confirmed by NMR and mass spectroscopy.

Calcd. for C$_{46}$H$_{60}$N$_6$O$_5$SF$_2$.0.15 CHCl (MW 864.99): C, 64.08; H, 7.05; N, 9.72; F, 4.39 Found C, 64.43; H, 7.08; N, 9.31; F, 4.50.

EXAMPLE 85

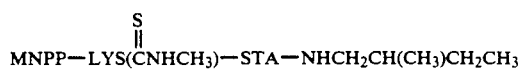

MNPP-LYS-STA-NHCH$_2$CH(CH$_3$)CH$_2$CH$_3$ (0.98 g, 1.52 mmole) was dissolved in 20 ml CHCl$_3$, to which was added methyl isothiocyanate (0.112 g, 1.53 mmole). After stirring at 23° overnight the mixture was evaporated in vacuo to a foam. Chromatography on silica gel, eluting with a gradient of 0–2% MeOH in CHCl$_3$ gave the product as a white foam, 0.91 g. The structure was confirmed by NMR and mass spectroscopy.

Calcd. for C$_{41}$H$_{59}$N$_5$O$_4$S.0.08 CHCl$_3$ (727.57): C, 67.82; H, 8.18; N, 9.62; S, 4.41; Cl, 1.17 Found C, 67.58; H, 8.27; N, 9.33; S, 4.22; Cl, 1.08.

EXAMPLE 86

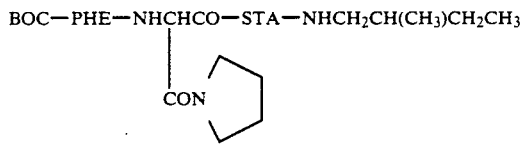

BOC-PHE-NHCH(CO$_2$CH$_3$)CO-STA-NHCH$_2$CH(CH$_3$)CH$_2$CH$_3$ (1.19 g, 1.98 mmole) (Example 35) was dissolved in 5 ml MeOH and pyrrolidine (2 ml, 23.9 mmole) was added, and the solution stirred at 23° overnight. The mixture was evaporated to a foam, redissolved in EtOAc and washed with 1N citric acid, saturated NaCl, saturated NaHCO$_3$ and saturated NaCl. After drying over MgSO$_4$ the solution was evaporated in vacuo to a white foam, 1.20 g. Chromatography on silica gel, eluting with CHCl$_3$/MeOH (9/1) gave the product as a white foam, 1.16 g. The structure was confirmed by NMR and mass spectroscopy.

Calcd. for C$_{34}$H$_{55}$N$_5$O$_7$.0.5 H$_2$O.0.1 CHCl$_3$ (MW 666.79): C, 61.47; H, 8.41; N, 10.52; Cl, 1.59; H$_2$O, 1.35 Found C, 62.53; H. 8.72; N, 10.71; Cl, 1.62; H$_2$O, 1.14.

EXAMPLE 87

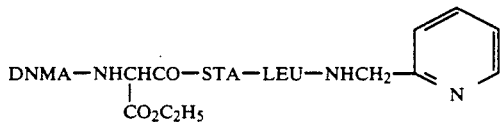

DNMA-NHCH(CO$_2$C$_2$H$_5$)CO$_2$H (1.47 g, 3.0 mmole) and HOBT (0.42 g, 3.09 mmole) were dissolved in 25 ml DMF and cooled to 0°. A solution of

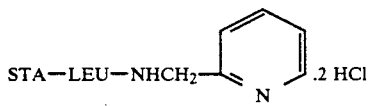

(1.37 g, 3.0 mmole) in 15 ml DMF and Et₃N (0.625 g, 6.18 mmole) were added, followed by DCC (0.64 g, 3.09 mmole). The mixture was stirred four hours at 0°, then at 23° overnight. The mixture was filtered and the DMF was removed under high vacuum. The residue was suspended in EtOAc, filtered, and washed with 1N citric acid, saturated NaCl, saturated NaHCO₃ and saturated NaCl. After drying over MgSO₄, the solution was evaporated to a glass, 2.15 g. Chromatography on silica gel, eluting with a gradient of 0–2% MeOH in CHCl₃ gave the product as a white foam, 1.07 g. The structure was confirmed by NMR and mass spectroscopy.

Calcd. for C₄₉H₅₉N₅O₇.0.1 CHCl₃.0.5 H₂O (MW 850.99): C, 69.30; H, 7.12; N, 8.23; Cl, 1.25; H₂O, 1.06 Found C, 69.46; H, 7.13; N, 8.14; Cl, 1.00; H₂O, 0.91.

EXAMPLE 88

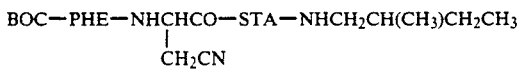

Following the procedure of Example 74, and substituting BOC-PHE for

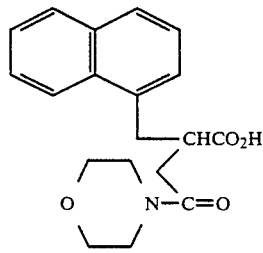

gave the title compound. The structure was confirmed by NMR and mass spectroscopy.

Calcd. for C₃₁H₄₉N₅O₆.0.3 CHCl₃ (MW 623.56): C, 60.29; H, 7.97; N, 11.23 Found C, 60.12; H, 7.86; N, 11.14.

INTERMEDIATES FOR EXAMPLE 1

BOC-PHE-ARG(NO₂)-OCH₃

A solution of 3.7 g ARG(NO₂)-OCH₃.HCl in 50 ml DMF was cooled in ice and treated with 1.85 ml of Et₃N. To this was then added successively 1.85 g HOBT, 3.64 g BOC-PHE, and then 2.83 g DCC. The solution was kept at 0° for one hour, then at room temperature for five days. The solvent was removed under reduced pressure, and the residue taken up in EtOAc. Insolubles were filtered off, and the filtrate washed with Na₂CO₃ solution, citric acid solution, then brine. After drying over MgSO₄ and removal of the solvent under reduced pressure, the residue was chromatographed on silica gel, eluting with CH₂Cl₂/MeOH (97:3). The appropriate fractions were combined to give 4.79 g (72.7%) of the product as a white foam.

BOC-PHE-ARG(NO₂)

A solution of 3.92 g of BOC-PHE-ARG(NO₂)-OCH₃ in 50 ml of MeOH was treated with 9 ml of 1N NaOH solution and stirred at room temperature for one hour. The solvent was removed under reduced pressure, and the residue taken up in H₂O and washed with EtOAc. The aqueous phase was acidified with citric acid and extracted with EtOAc. The EtOAc was washed with brine and dried over MgSO₄. After filtering, removal of the solvent under reduced pressure gave 3.66 g (96%) of the product as a white foam.

INTERMEDIATES FOR EXAMPLES 2, 3, 5–13, AND 65

BOC-LYS(Z)-STA-NHCH₂CH(CH₃)CH₂CH₃

BOC-LYS(Z) (1.98 g), STA-NHCH₂CH(CH₃)CH₂CH₃.HCl (1.5 g), hydroxybenzotriazole (0.72 g), and triethyl amine (0.74 ml) were mixed together in dimethylformamide (15 ml) and cooled to 0°. Dicyclohexylcarbodiimide (1.1 g) was added, and the mixture was allowed to warm slowly to 25° and then stir for 72 hours. The mixture was filtered, and the filtrate was extracted with EtOAc and water. The organic phase was washed with water, sodium bicarbonate solution, and brine. The organic phase was dried over sodium sulfate, filtered, and evaporated. The residue was eluted from silica gel with 1:1 EtOAc/hexane to give 2.7 g of product.

LYS(Z)-STA-NHCH₂CH(CH₃)CH₂CH₃

BOC-LYS(Z)-STA-NHCH₂CH(CH₃)CH₂CH₃ (2.7 g) was dissolved in dichloromethane (30 ml), and trifluoroacetic acid (4 ml) was added. The mixture was stirred for two hours at 25°. The solvent was evaporated, and the residue was extracted with EtOAc and sodium carbonate solution. The organic phase was washed with brine, dried over sodium sulfate, filtered, and evaporated to give 2.1 g of the product.

DNMA-LYS(Z)-STA-NHCH₂CH(CH₃)CH₂CH₃

LYS(Z)-STA-NHCH₂CH(CH₃)CH₂CH₃ (2.1 g), di-(1-naphthylmethyl)acetic acid (1.51 g), and hydroxybenzotriazole (0.6 g) were dissolved in dimethylformamide (20 ml) and cooled to 0°. Dicyclohexylcarbodiimide (0.92 g) was added, and the mixture was allowed to warm slowly to 25° and stir for 24 hours. The mixture was filtered, and the filtrate was extracted with ethyl acetate and water. The organic phase was washed with water, sodium bicarbonate, and brine. The organic phase was dried over sodium sulfate, filtered, and evaporated. The crude product was recrystallized from chloroform to give 1.95 g of product. The residue from the mother liquor was purified by chromatography on silica gel, eluting with CHCl₃/EtOAc (3:1). Combining the appropriate fractions gave an additional 0.5 g of product.

DNMA-LYS-STA-NHCH₂CH(CH₃)CH₂CH₃

DNMA-LYS(Z)-STA-NHCH₂CH(CH₃)CH₂CH₃ (1.95 g) was dissolved in methanol (30 ml) and palladium on carbon (20%) (0.2 g) was added. The flask was flushed with hydrogen and stirred for six hours. The flask was flushed with nitrogen, and the mixture was filtered. The solvent was evaporated to give 1.6 g of product.

INTERMEDIATES FOR EXAMPLE 4

Z-ORN(PHT)-STA-LEU-NHCH₂Ph

Z-ORN(PHT) (French Pat. 1,430,140) (1.60 g, 4.03 mmole) and HOBT.H₂O (0.544 g, 4.23 mmole) were dissolved in 10 ml DMF, diluted to 90 ml with CH₂Cl₂ and cooled to −5°. DCC (0.87 g, 4.23 mmole) was charged as a solution in 20 ml of cooled CH₂Cl₂ followed by a cooled suspension of STA-LEU-NHCH₂Ph.HCl (1.67 g, 4.03 mmole) in a mixture of 40 ml CH₂Cl₂ and Et₃N (0.56 ml, 4.23 mmole). After stirring 16 hours at 25°, the mixture was filtered, stripped, and resuspended in EtOAc. The suspension was washed with 1N citric acid, brine, saturated NaHCO₃ solution, and brine. The suspension was stripped to a paste, triturated with H₂O, filtered, and dissolved in THF. The THF solution was dried over MgSO₄, filtered, and stripped to a solid, 3.14 g. Recrystallization from THF/Et₂O gave 2.8 g of the product as a solid. IR, NMR, and mass spectral analyses confirmed the structure.

ORN(PHT)-STA-LEU-NHCH₂Ph

Z-ORN(PHT)-STA-LEU-NHCH₂Ph (2.59 g, 3.43 mmole) was dissolved in 60 ml HOAc. Twenty percent palladium on charcoal catalyst (0.10 g) was added, and the mixture was purged with hydrogen gas overnight. The mixture was filtered, stripped, and the residue dissolved in EtOAc. The solution was washed with 5% NaOH and then brine. The solution was dried over MgSO₄, filtered, and stripped to a foam, 2.03 g. The foam was chromatographed on silica gel eluting with a gradient of 0 to 5% MeOH in CHCl₃, giving a white foam, 1.52 g. NMR, IR, and mass spectral analyses confirmed the structure.

INTERMEDIATES FOR EXAMPLE 8

BOC-CYSTA-NHCH₂CH(CH₃)CH₂CH₃

A solution of 6.78 g (21.5 mmole) of BOC-CYSTA and 2.9 g (21.5 mmole) of HOBT in 100 ml DMF was cooled in ice and 4.48 g (21.5 mmole) of DCC in 10 ml DMF added, followed by 1.88 g (21.5 mmole) of S-(−)-1-amino-2-methylbutane. Keep at 0° for one-half hour, then let stir at room temperature overnight. The mixture was filtered and the solvent removed under high vacuum. The residue was taken up in EtOAc and washed with 1N HCl, saturated NaHCO₃, and saturated NaCl. Drying and removal of the solvent under reduced pressure gave the crude product. Chromatography on silica gel, eluting with CHCl₃/MeOH (99/1) gave 8.2 g of the product as an oil. The structure was confirmed by mass spectroscopy.

CYSTA-NHCH₂CH(CH₃)CH₂CH₃.HCl

A solution of 8.2 g (21.3 mmole) of BOC-CYSTA-NHCH₂CH(CH₃)CH₂CH₃ in 85 ml of CH₂Cl₂ was saturated with HCl gas, stirred for one hour, then resaturated with HCl gas and allowed to stir for an additional three hours. The solution was diluted with Et₂O and the precipitated solid collected and dried. There was obtained 5.47 g of the product as a white solid. The structure was confirmed by mass spectroscopy.

BOC-LYS(Z)-CYSTA-NHCH₂CH(CH₃)CH₂CH₃

A solution of 1.7 g (4.6 mmole) of BOC-LYS(Z), 1.5 g (4.7 mmole) of CYSTA-NHCH₂CH(CH₃)CH₂CH₃.HCl, and 0.63 g (4.7 mmole) of HOBT in 20 ml DMF was cooled in ice and treated with 0.85 ml (6.1 mmole) of Et₃N followed by 0.96 g (4.7 mmole) of DCC. The mixture was allowed to stir at room temperature for two days. The mixture was filtered and the filtrate diluted with EtOAc. The organic phase was washed with H₂O, saturated NaHCO₃, and saturated NaCl. Drying and removal of the solvent under reduced pressure gave the crude product which was purified by chromatography on silica gel, eluting with EtOAc/hexane (1/1), then EtOAc/hexane (3/1). There was obtained 2.6 g of product, of sufficient purity for using in the next reaction.

DNMA-LYS(Z)-CYSTA-NHCH₂CH(CH₃)CH₂CH₃

A solution 2.6 g (3.3 mmole) of BOC-LYS(Z)-CYSTA-NHCH₂CH(CH₃)CH₂CH₃ in 20 ml of CH₂Cl₂ was treated with 5 ml of TFA and stirred at room temperature for five hours. The solvent was removed under reduced pressure and the residue taken up in EtOAc and washed with saturated NaHCO₃, then saturated NaCl. Drying and removal of the solvent under reduced pressure gave crude LYS(Z)-CYSTA-NHCH₂CH(CH₃)CH₂CH₃.

This was taken up in 20 ml DMF and 1.12 g (3.3 mmole) of di-(1-naphthylmethyl)acetic acid and 0.45 g (3.3 mmole) of HOBT added. The solution was cooled in ice and 0.68 g (3.3 mmole) of DCC added and the solution allowed to warm to room temperature overnight. The mixture was filtered and the filtrate diluted with EtOAc. The solution was washed with H₂O, saturated NaHCO₃, and saturated NaCl. Drying and removal of the solvent under reduced pressure gave the crude material which could be purified by recrystallization from EtOAc. There was obtained 2.8 g of product. The structure was confirmed by NMR spectroscopy.

DNMA-LYS-CYSTA-NHCH₂CH(CH₃)CH₂CH₃

A solution of 2.8 g of DNMA-LYS(Z)-CYSTA-NHCH₂CH(CH₃)CH₂CH₃ in 30 ml MeOH was treated with 0.2 g of 20% Pd/C and stirred under a hydrogen atmosphere for six hours. The mixture was filtered, and the solvent removed under reduced pressure to give 2.0 g of the product. The structure was confirmed by NMR and mass spectroscopy.

INTERMEDIATES FOR EXAMPLE 14

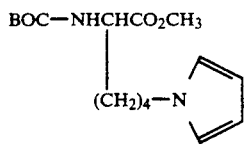

A solution of 1.7 g (6.5 mmole) of α-BOC-LYS-OCH₃ in 30 ml HOAc was treated with 0.86 g (6.5 mmole) of 2,5-dimethoxyfuran and heated to reflux while allowing 15 ml of HOAc to distill off. The remainder of the HOAc was removed under reduced pressure. The residue was taken up in EtOAc and washed with saturated NaHCO₃, then saturated NaCl. Drying and removal of the solvent under reduced pressure gave the crude product which was purified by chromatography on silica gel, eluting with hexane/EtOAc (4/1). There was obtained 0.9 g of product. The structure was confirmed by NMR spectroscopy.

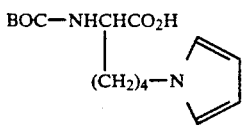

A solution of 0.9 g (2.9 mmole) of

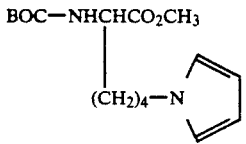

in 15 ml dioxane was cooled to −15° and 0.12 g (3.0 mmole) of NaOH in 10 ml H₂O added, and the solution allowed to stir at room temperature for two hours. The solution was acidified with citric acid and extracted with EtOAc. The EtOAc was washed with H₂O, then saturated NaCl. Drying and removal of the solvent under reduced pressure gave 0.75 g of product, of sufficient purity for use in the following step. The structure was confirmed by NMR spectroscopy.

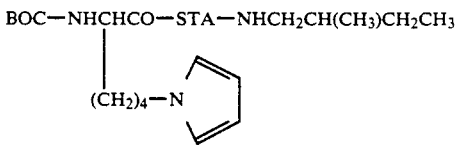

A solution of 0.75 g (2.5 mmole) of

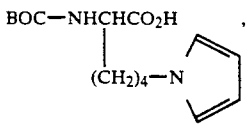

0.34 g (2.5 mmole) of HOBT, and 0.71 g (2.5 mmole) of STA-NHCH₂CH(CH₃)CH₂CH₃.HCl in 15 ml of DMF was cooled in ice and 0.35 ml (2.5 mmole) of Et₃N added, followed by 0.52 g (2.5 mmole) of DCC. The cooling was removed and the solution allowed to stir at room temperature overnight. The mixture was filtered and the filtrate diluted with EtOAc and washed with H₂O, saturated NaHCO₃, and saturated NaCl. Drying and removal of the solvent under reduced pressure gave the crude product which was chromatographed on silica gel, eluting with EtOAc/hexane (1/1). There was obtained 0.8 g of product. The structure was confirmed by NMR spectroscopy.

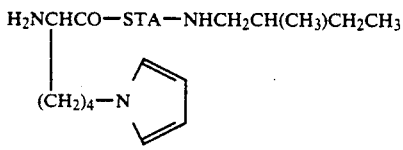

A solution of 0.8 g of

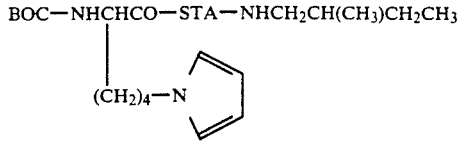

in 25 ml MeOH was treated with 10% HCl until the solution became cloudy. The mixture was allowed to stir at room temperature for eight hours. The solvent was removed under reduced pressure and the residue mixed with sodium carbonate solution and extracted with EtOAc. The solution was washed with saturated NaCl, dried, and the solvent removed under reduced pressure to give 0.5 g of product of sufficient purity for use in the following step. The structure was confirmed by NMR spectroscopy.

INTERMEDIATES FOR EXAMPLE 15

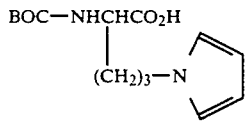

A solution of 1.2 g (5.2 mmole) of α-BOC-ORN in 30 ml of HOAc was treated with 0.8 g (6.1 mmole) of 2,5-dimethoxyfuran and heated to reflux while allowing 15 ml of HOAc to distill off. The remainder of the HOAc was removed under reduced pressure. The residue was taken up in dilute NaOH, acidified with 1N citric acid and extracted with CHCl₃. The CHCl₃ was dried and the solvent removed under reduced pressure giving the crude product which was purified by taking up in EtOAc and filtering through a plug of silica gel. Removal of the solvent under reduced pressure gave 0.7 g of the product as a yellow oil. The structure was confirmed by NMR spectroscopy.

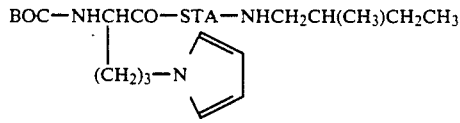

A solution of 0.55 g (1.9 mmole) of

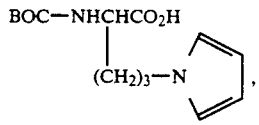

0.54 g (1.9 mmole) of STA-NHCH₂CH(CH₃)CH₂CH₃.HCl, and 0.25 g (1.9 mmole) of HOBT in 15 ml DMF was cooled in ice and 0.27 ml (1.9 mmole) of Et₃N was added, followed by 0.4 g (1.9 mmole) of DCC. The solution was allowed to warm to room temperature and stir overnight. The mixture was filtered and the filtrate diluted with EtOAc and washed with H₂O, saturated NaHCO₃, and saturated NaCl. Drying and removal of the solvent under reduced pressure gave the crude product which was chromatographed on silica gel, eluting with EtOAc/hexane (1/1). There was obtained 0.76 g of product, mp 136°-139°. The structure was confirmed by NMR spectroscopy.

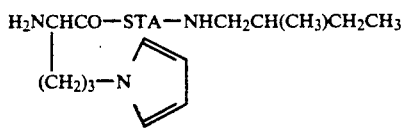

A solution of 0.76 g (1.5 mmole) of

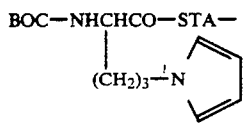

in 20 ml MeOH was treated with 15 ml 10% HCl and stirred at room temperature for three hours. The solvent was removed under reduced pressure, and the residue was mixed with saturated NaHCO$_3$ and extracted with EtOAc. Drying and removal of the solvent under reduced pressure gave 0.61 g of product, of sufficient purity for use in the following reaction. The structure was confirmed by NMR spectroscopy.

INTERMEDIATES FOR EXAMPLE 16

BOC-LYS(Z)-STA-LEU-NHCH$_2$Ph

A solution of 4.0 g (10.5 mmole) of BOC-LYS(Z), 4.35 g (10.5 mmole) of STA-LEU-NHCH$_2$Ph.HCl, and 1.42 g (10.5 mmole) of HOBT in 30 ml DMF was cooled in ice and 1.46 ml (10.5 mmole) of Et$_3$N added, followed by 2.2 g (10.7 mmole) of DCC. The solution was stirred at room temperature for three days. The mixture was filtered and the filtrate diluted with EtOAc and washed with H$_2$O, saturated NaHCO$_3$, and saturated NaCl. Drying and removal of the solvent under reduced pressure gave the crude product which was purified by chromatography on silica gel, eluting with EtOAc/hexane (1/1), then EtOAc. There was obtained 6.6 g of product. The structure was confirmed by NMR spectroscopy.

LYS(Z)-STA-LEU-NHCH$_2$Ph

A solution of 6.6 g (8.9 mmole) of BOC-LYS(Z)-STA-LEU- NHCH$_2$Ph in 100 ml CH$_2$Cl$_2$ was treated with 15 ml TFA and stirred at room temperature for two hours. The solvent was removed under reduced pressure and the residue mixed with sodium carbonate solution and extracted with EtOAc. The EtOAc was washed with saturated NaCl, dried, and the solvent removed under reduced pressure to give 5.6 g of the product, of sufficient purity to use in the following reaction.

INTERMEDIATE FOR EXAMPLES 17-22

DNMA-LYS-STA-LEU-NHCH$_2$Ph

A solution of 2.0 g (2.1 mmole) of DNMA-LYS(Z)-STA-LEU-NHCH$_2$Ph in 30 ml MeOH was treated with 0.2 g 20% Pd/C and stirred under a hydrogen atmosphere for five hours. The mixture was filtered and the solvent removed under reduced pressure to give 1.8 g of the product, sufficiently pure for use in the following reactions.

INTERMEDIATES FOR EXAMPLE 20

CH$_3$SO$_3$(CH$_2$)$_5$-NHZ

A solution of 4.0 g (16.9 mmole) of HO-(CH$_2$)$_5$-NHZ in 70 ml CHCl$_3$ was cooled to $-20°$ and 2.35 ml (16.9 mmole) of Et$_3$N added followed by the dropwise addition of 1.3 ml (16.9 mmole) of methanesulfonyl chloride. The solution was stirred at $-20°$ for two hours, then washed with saturated NaHCO$_3$ and saturated NaCl. Drying and removal of the solvent under reduced pressure left 5.6 g of the crude product, sufficiently pure for use in the following reaction.

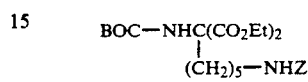

0.85 g (17.7 mmole) of NaH (50% in mineral oil) was washed free of oil and suspended in 20 ml of DMSO. To this was added 4.8 g (17.4 mmole) of BOC-NHCH(CO$_2$Et)$_2$ in portions and the suspension stirred until the evolution of hydrogen had ceased. This was then treated with 5.6 g (17.8 mmole) of CH$_3$SO$_3$-(CH$_2$)$_5$-NHZ and 2.0 g of KI and stirred at room temperature for four days. The mixture was diluted with EtOAc and washed with 1N citric acid, H$_2$O, saturated NaHCO$_3$, then saturated NaCl. Drying and removal of the solvent under reduced pressure left 9.7 g of the crude product, sufficiently pure for use in the following step.

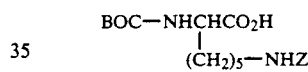

A solution of 9.7 g (19.6 mmole) of

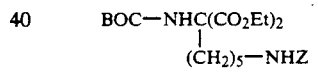

in 20 ml of dioxane was treated with 1.6 g (40 mmole) of NaOH in 10 ml of H$_2$O and the solution stirred at room temperature for three hours. The solution was diluted with H$_2$O and extracted with Et$_2$O. The aqueous phase was brought to pH 1 and extracted with EtOAc. This was washed with H$_2$O and saturated NaCl. Drying and removal of the solvent under reduced pressure gave the malonic acid.

This was dissolved in 100 ml toluene and heated at reflux for four hours. The toluene was removed under reduced pressure and the residue chromatographed on silica gel, eluting with hexane/EtOAc (5/1). There was obtained 1.9 g of product. The structure was confirmed by NMR spectroscopy.

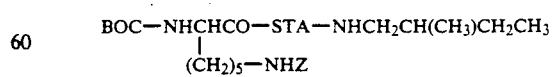

A solution of 1.9 g (4.8 mmole) of

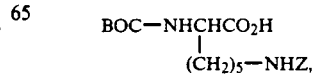

1.1 g (4.5 mmole) of STA-NHCH$_2$CH(CH$_3$)CH$_2$CH$_3$, and 0.65 g (4.8 mmole) of HOBT in 20 ml DMF was cooled in ice and 0.94 g (4.6 mmole) of DCC added and the solution stirred at room temperature overnight. The mixture was filtered and the filtrate diluted with EtOAc and washed with H$_2$O, saturated NaHCO$_3$, then saturated NaCl. Drying and removal of the solvent under reduced pressure left the crude product which was chromatographed on silica gel, eluting with hexane/EtOAc (1/1). There was obtained 2.1 g of product, sufficiently pure for use in the following step.

INTERMEDIATE FOR EXAMPLE 21 AND 22

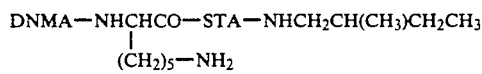
DNMA—NHCHCO—STA—NHCH$_2$CH(CH$_3$)CH$_2$CH$_3$
|
(CH$_2$)$_5$—NH$_2$ A solution of 0.4 g (0.5 mmole) of

DNMA—NHCHCO—STA—
|
(CH$_2$)$_5$—NHZ in 20 ml MeOH was treated with 0.1 g of 20% Pd/C and stirred under hydrogen for three hours. The mixture was then filtered and the solvent removed under reduced pressure to give 0.3 g of the product, sufficiently pure for use in the following reactions.

INTERMEDIATES FOR EXAMPLE 25

CH$_3$SO$_3$(CH$_2$)$_6$-NHZ

A solution of 4.0 g (15.9 mmole) of HO-(CH$_2$)$_6$-NHZ in 70 ml CHCl$_3$ was cooled to $-20°$ and 2.35 ml (16.9 mmole) of Et$_3$N added followed by the dropwise addition of 1.3 ml (16.9 mmole) of methanesulfonyl chloride. The solution was stirred at $-20°$ for two hours, then washed with saturated NaHCO$_3$ and saturated NaCl. Drying and removal of the solvent under reduced pressure left 5.8 g of the crude product, sufficiently pure for use in the following reaction.

BOC—NHC(CO$_2$Et)$_2$
|
(CH$_2$)$_6$—NHZ 0.85 g (17.7 mmole) of NaH (50% in mineral oil) was washed free of the oil and suspended in 20 ml DMSO. To this was added 4.8 g (17.4 mmole) of BOC-NHCH(CO$_2$Et)$_2$ in portions and the suspension stirred until the evolution of hydrogen had ceased. This was then treated with 5.8 g (17.6 mmole) of CH$_3$SO$_3$-(CH$_2$)$_6$-NHZ and 2.0 g of KI and stirred at room temperature for four days. The mixture was diluted with EtOAc and washed with 1N citric acid, H$_2$O, saturated NaHCO$_3$, and saturated NaCl. Drying and removal of the solvent under reduced pressure gave 9.0 g of crude product, sufficiently pure for use in the following reaction.

BOC—NHCHCO$_2$H
|
(CH$_2$)$_6$—NHZ

A solution of 9.0 g (17.7 mmole) of

BOC—NHC(CO$_2$Et)$_2$
|
(CH$_2$)$_6$—NHZ in 30 ml dioxane was treated with 1.5 g (37.5 mmole) of NaOH in 10 ml H$_2$O and the solution stirred at room temperature for three hours. The solution was diluted with H$_2$O and extracted with Et$_2$O. The pH was brought to 1 and the mixture extracted with EtOAc, and the EtOAc washed with H$_2$O and saturated NaCl. Drying and removal of the solvent under reduced pressure gave the malonic acid. This was taken up in 100 ml toluene and heated at reflux for four hours. The solvent was removed under reduced pressure and the residue chromatographed on silica gel, eluting with hexane/EtOAc (5/1), to give 1.1 g of product.

BOC—NHCHCO—STA—NHCH$_2$CH(CH$_3$)CH$_2$CH$_3$
|
(CH$_2$)$_6$—NHZ

A solution of 1.1 g (2.9 mmole) of

BOC—NHCHCO$_2$H
|
(CH$_2$)$_6$—NHZ, 0.71 g (2.9 mmole) of STA-NHCH$_2$CH(CH$_3$)CH$_2$CH$_3$, and 0.39 g (2.9 mmole) of HOBT in 20 ml DMF was cooled in ice and 0.6 g (2.9 mmole) of DCC added and the solution left stirring at room temperature overnight. The mixture was then filtered and the filtrate diluted with EtOAc. The EtOAc was washed with H$_2$O, saturated NaHCO$_3$, and saturated NaCl. Drying and removal of the solvent under reduced pressure gave the crude product which was chromatographed on silica gel, eluting with EtOAc/hexane (1/1). There was obtained 1.3 g of product.

INTERMEDIATE FOR EXAMPLES 26 AND 27

DNMA—NHCHCO—STA—NHCH$_2$CH(CH$_3$)CH$_2$CH$_3$
|
(CH$_2$)$_6$—NH$_2$

A solution of 0.5 g (0.6 mmole) of

DNMA—NHCHCO—STA—
|
(CH$_2$)$_6$—NHZ in 20 ml MeOH was treated with 0.1 g of 20% Pd/C and stirred under hydrogen for four hours. The mixture was filtered and the solvent removed under reduced pressure to give 0.42 g of the crude product, sufficiently pure to use in the following steps.

INTERMEDIATE FOR EXAMPLE 28

BOC—NHCHCO—STA—LEU—NHCH$_2$Ph
|
(CH$_2$)$_6$—NHZ

A solution of 0.86 g (2.3 mmole) of

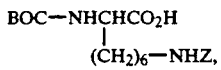
(CH₂)₆—NHZ, 0.86 g (2.1 mmole) of STA-LEU-NHCH₂Ph.HCl, and 0.3 g (2.2 mmole) of HOBT in 15 ml DMF was cooled in ice and treated with 0.4 ml (2.9 mmole) of Et₃N followed by 0.5 g (2.4 mmole) of DCC. The solution was allowed to stir at room temperature overnight. The mixture was filtered and the filtrate diluted with EtOAc and washed with H₂O, saturated NaHCO₃, and saturated NaCl. Drying and removal of the solvent under reduced pressure gave the crude product which was chromatographed on silica gel, eluting with EtOAc/hexane (1/1). There was obtained 1.0 g of product. The structure was confirmed by NMR spectroscopy.

INTERMEDIATES FOR EXAMPLE 29

ClCH₂C≡C—CH₂NHZ

A solution of 1.0 g (7.1 mmole) of ClCH₂C≡C—CH₂NH₂HCl (Ann Chim. 13, 656 (1958)) in 20 ml of THF/H₂O (1/1) was cooled in ice and treated with 0.3 g (7.5 mmole) of NaOH in 5 ml of H₂O, then treated dropwise with 1.0 ml (7.1 mmole) of benzyl chloroformate while simultaneously adding dropwise a solution of 0.3 g (7.5 mmole) of NaOH in 5 ml H₂O. The solution was allowed to stir at 0° for two hours, then was extracted with EtOAc. The EtOAc was washed with saturated NaHCO₃ and saturated NaCl. Drying and removal of the solvent under reduced pressure gave 1.8 g of the product as an oil which solidified on standing. The structure was confirmed by NMR spectroscopy.

0.33 g (6.9 mmole) of NaH (50% in mineral oil) was washed free of the oil and suspended in 15 ml DMSO. To this was added 1.9 g (6.8 mmole) of BOC-NHCH(CO₂Et)₂ and the suspension stirred until the evolution of hydrogen had ceased. This was then treated with 1.8 g (6.6 mmole) of ClCH₂C≡C—CH₂NHZ and 2.0 g KI and stirred at room temperature overnight. The solution was diluted with EtOAc and washed with H₂O, saturated NaHCO₃, and saturated NaCl. Drying and removal of the solvent under reduced pressure gave the crude product which was chromatographed on silica gel, eluting with hexane/EtOAc (9/1). There was obtained 2.5 g of product. The structure was confirmed by NMR spectroscopy.

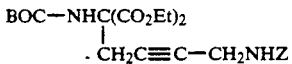

A solution of 2.5 g (5.4 mmole) of

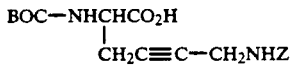

in 20 ml THF was treated with 1.0 g (25.0 mmole) of NaOH in 20 ml H₂O and the solution stirred at room temperature for six hours. The solution was acidified with 1N citric acid and extracted with EtOAc. The EtOAc was washed with H₂O and saturated NaCl. Drying and removal of the solvent under reduced pressure gave the malonic acid.

This was taken up in 25 ml toluene and heated at reflux for two hours. The solvent was removed under reduced pressure to give the crude product which was chromatographed on silica gel, eluting with hexane/EtOAc (3/1). There was obtained 1.6 g of product, sufficiently pure for use in the following reaction.

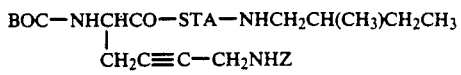

A solution of 1.6 g (4.3 mmole) of

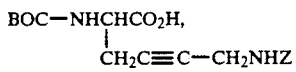

1.0 g (4.1 mmole) of STA-NHCH₂CH(CH₃)CH₂CH₃, and 0.57 g (4.2 mmole) of HOBT in 15 ml DMF was cooled in ice and treated with 0.88 g (4.3 mmole) of DCC and the solution allowed to stir at room temperature for four days. The mixture was filtered and the filtrate diluted with EtOAc and washed with H₂O, saturated NaHCO₃, and saturated NaCl. Drying and removal of the solvent under reduced pressure gave the crude product which was chromatographed on silica gel, eluting with EtOAc/hexane (1/1). There was obtained 2.5 g of product.

INTERMEDIATES FOR EXAMPLES 30 AND 31

BOC-ORN(Z)-STA-NHCH₂CH(CH₃)CH₂CH₃

A solution of 1.3 g (3.5 mmole) of BOC-ORN(Z), 1.0 g (3.6 mmole) of STA-NHCH₂CH(CH₃)CH₂CH₃.HCl, and 0.48 g (3.6 mmole) of HOBT in 20 ml DMF was cooled in ice and 0.5 ml (3.6 mmole) of Et₃N added followed by 0.74 g (3.6 mmole) of DCC. The solution was allowed to stir at room temperature overnight. The mixture was filtered and the filtrate diluted with EtOAc and washed with H₂O, saturated NaHCO₃, then saturated NaCl. Drying and removal of the solvent under reduced pressure gave the crude product which was chromatographed on silica gel, eluting with EtOAc/hexane (1/1). There was obtained 1.5 g of product. The structure was confirmed by NMR and mass spectroscopy.

ORN(Z)-STA-NHCH₂CH(CH₃)CH₂CH₃

A solution of 1.25 g (2.1 mmole) of BOC-ORN(Z)-STA-NHCH₂CH(CH₃)CH₂CH₃ in 50 ml CH₂Cl₂ was treated with 6 ml TFA and stirred at room temperature for two hours. The solvent was removed under reduced pressure and the residue taken up in EtOAc and washed with saturated NaHCO₃ and saturated NaCl. Drying and removal of the solvent under reduced pressure left 1.0 g of product. The structure was confirmed by NMR spectroscopy.

DNMA-ORN(Z)-STA-NHCH₂CH(CH₃)CH₂CH₃

A solution of 0.72 g (2.1 mmole) of di-(1-naphthylmethyl)acetic acid, 1.0 g (2.0 mmole) of ORN(Z)-STA-NHCH₂CH₂(CH₃)CH₂CH₃, and 0.29 g (2.1 mmole) of HOBT in 20 ml DMF was cooled in ice and treated with 0.44 g (2.1 mmole) of DCC and the solution stirred at room temperature for three days. The mixture was filtered and the filtrate diluted with EtOAc and washed with H₂O, saturated NaHCO₃, and saturated NaCl. Drying and removal of the solvent under reduced pressure gave the crude product which was chromatographed on silica gel, eluting with EtOAc/hexane (1/1), then EtOAc. There was obtained 1.27 g of product. The structure was confirmed by NMR and mass spectroscopy.

DNMA-ORN-STA-NHCH₂CH(CH₃)CH₂CH₃

A solution of 1.1 g of DNMA-ORN(Z)-STA-NHCH₂CH(CH₃)CH₂CH₃ in 20 ml MeOH was treated with 0.1 g 20% Pd/C and stirred under hydrogen for five hours. The mixture was filtered and the solvent removed under reduced pressure to give 1.0 g of product, sufficiently pure for use in the following reactions.

INTERMEDIATES FOR EXAMPLE 33

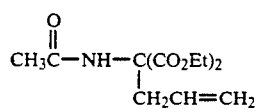

To 150 ml absolute EtOH was added 4.6 g (0.2 g.atom) of sodium. When all had reacted, the solution was treated with 43.5 g (0.2 mole) of diethyl acetylaminomalonate. The solution was warmed to 50° for one hour, then recooled and treated dropwise with a solution of 17.4 ml (0.2 mole) of allyl bromide in 100 ml absolute EtOH. The mixture was kept at 50° for twenty-four hours, then stripped to an oily solid. The material was taken up in Et₂O and washed twice with H₂O, then saturated NaCl. Drying and removal of the solvent under reduced pressure left 42.4 g of the crude product. The structure was confirmed by NMR spectroscopy.

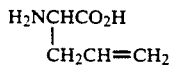

A solution of 42.4 g of

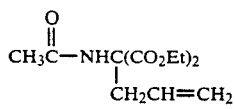

in 200 ml of
A solution of 42.4 g of

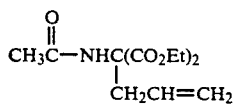

concentrated HCl was heated at reflux for seven hours, then stripped under reduced pressure to a viscous oil. This was taken up in 140 ml absolute EtOH and concentrated NH₄OH was added until basic to litmus. The solution was cooled and the precipitated product collected by filtration. There was obtained 16.3 g of product. The structure was confirmed by NMR spectroscopy.

A suspension of 16.1 g (0.14 mole) of

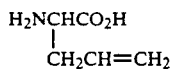

in 150 ml dioxane was treated with 70 ml (0.14 mole) of 2N NaOH causing solution. Di-t-butyldicarbonate (34.0 g, 0.15 mole) was added and the solution stirred at room temperature for two hours. The pH was adjusted to 8.5 and the solution diluted with H₂O and washed twice with Et₂O. The pH was then brought to 2.0 and washed twice with Et₂O. The Et₂O was washed with saturated NaCl, dried, and the solvent removed under reduced pressure giving 19.7 g of the product as a clear oil. The structure was confirmed by NMR and mass spectroscopy.

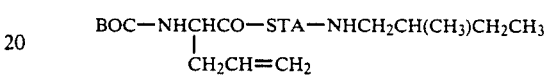

A solution of 2.16 g (10.0 mmole) of

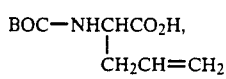

1.35 g (10.0 mmole) of HOBT and 2.81 g (10.0 mmole) of STA-NHCH₂CH(CH₃)CH₂CH₃.HCl in 30 ml DMF was cooled in ice and 1.4 ml (10.0 mmole) of Et₃N added, followed by 2.1 g (10.0 mmole) of DCC and the solution allowed to stir at room temperature overnight. The mixture was filtered and the solvent removed under high vacuum. The residue was taken up in EtOAc and washed with 1N HCl, saturated NaHCO₃, and saturated NaCl. Drying and removal of the solvent under reduced pressure gave the crude product which was chromatographed on silica gel, eluting with CHCl₃/MeOH (98/2). There was obtained 1.94 g of the product as a white foam. The structure was confirmed by NMR and mass spectroscopy.

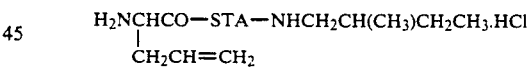

A solution of 1.94 g (4.4 mmole) of

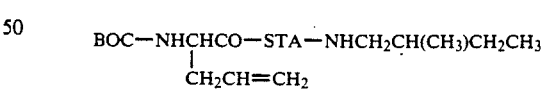

in 20 ml CH₂Cl₂ was treated with 10 ml TFA and stirred for one hour. The solvent was removed under reduced pressure and the residue taken up in CH₂Cl₂ and the solvent removed again. The residue was then taken up in CH₂Cl₂ and treated with HCl gas. The solvent was removed under reduced pressure to give 1.66 g of the product, of sufficient purity to use in the following step.

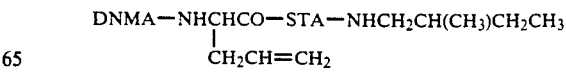

A solution of 1.5 g (4.4 mmole) of di-(1-naphthylmethyl) acetic acid and 0.6 g (4.4 mmole) of HOBT in 20 ml DMF was cooled in ice and 0.92 g (4.4 mmole) of DCC added and the solution stirred at 0° for fifteen minutes.

To this was added a cold solution of 1.66 g (4.4 mmole) of

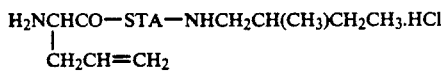

and 0.62 ml (4.4 mmole) of Et$_3$N in 20 ml DMF. The solution was allowed to stir at room temperature overnight. The mixture was poured into H$_2$O and extracted three times with EtOAc. The EtOAc was washed with H$_2$O, 1N HCl, saturated NaHCO$_3$, and saturated NaCl. Drying and removal of the solvent under reduced pressure gave the crude product which was chromatographed on silica gel, eluting with CHCl$_3$/MeOH (98/2). There was obtained 2.4 g of product contaminated with some starting di-(1-naphthylmethyl)acetic acid. The residue was taken up in Et$_2$O and washed twice with 1N NaOH, H$_2$O, then saturated NaCl. Drying and removal of the solvent under reduced pressure gave 2.12 g of the product as a white foam. The structure was confirmed by NMR and mass spectroscopy.

INTERMEDIATES FOR EXAMPLES 34 AND 35

AMINOMALONIC ACID, METHYL BENZYL ESTER

Methyl, benzyl, isonitrosomalonate was prepared from 97 g of methyl, benzyl malonate by the procedure described in Org. Syn. Coll. Vol. 5, p. 373. The 100 g of crude product obtained was reduced to the amino derivative by the procedure described in J. Am. Chem. Soc., 75, 1970 (1953). The 94 g of crude product was used in the following step without further purification.

BOC-AMINOMALONIC ACID, METHYL BENZYL ESTER

A solution of 94 g of aminomalonic acid, methyl benzyl ester in 75 ml Et$_2$O was cooled to 5° and treated with 91.66 g of di-t-butyldicarbonate. After standing at 4° overnight, the solvent was removed under reduced pressure giving an oil. Chromatography on silica gel, eluting with hexane/EtOAc (85/15) gave 66.97 g (49% yield) of the product as an oil which solidified on standing. The structure was confirmed by NMR and mass spectroscopy.

BOC-AMINOMALONIC ACID, METHYL ESTER

To a solution of 16.17 g (13.5 mmole) of BOC-aminomalonic acid, methyl benzyl ester in 250 ml MeOH was added 0.66 g of 20% Pd/C catalyst. The suspension was purged with hydrogen gas for one and one-half hours, after which the suspension was filtered and the solvent removed under reduced pressure at 30°, giving a syrup, 12.5 g. The product was kept at 4° until use in the following reaction.

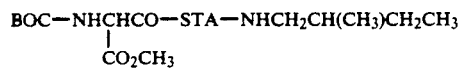

A solution of 2.50 g (10.7 mmole) of BOC-aminomalonic acid, methyl ester and 1.52 g (11 mmole) of HOBT in 50 ml DMP was combined with a solution of 3.01 g (10.7 mmole) of STA-NHCH$_2$CH(CH$_3$)CH$_2$CH$_3$.HCl and 1.57 ml (11.0 mmole) Et$_3$N in 25 ml DMF. To the mixture was added 2.32 g (11.0 mmole) DCC, and the mixture stirred for five hours at room temperature, then kept at 4° overnight. The mixture was filtered, and the filtrate evaporated under high vacuum to a glass, 4.29 g. The crude product was chromatographed on silica gel, eluting with EtOAc. Combination of the appropriate fractions gave a white foam, 3.09 g, of sufficient purity for use in the following reaction. The structure was confirmed by NMR and mass spectroscopy.

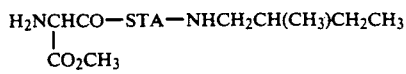

To a solution of 2.86 g (6.22 mmole) of

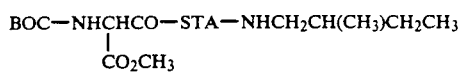

in 75 ml CH$_2$Cl$_2$ was added 10 ml TFA. After two hour temperature the solvent was removed under reduced pressure, and the residue partitioned between Et$_2$O and saturated NaCl which had been adjusted to pH 9.5 with solid sodium carbonate. The organic phase was washed with saturated NaCl, dried, and evaporated to a foam, 1.62 g. The material was sufficiently pure for use in the following reaction.

INTERMEDIATE FOR EXAMPLE 36

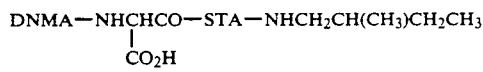

To a solution of 1.79 g (2.63 mmole) of

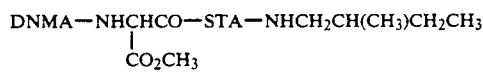

in 25 ml MeOH was added 5.0 ml 1N NaOH. After stirring one and one-half hours at room temperature, 4.9 ml 1N HCl was added. The solvent was removed under reduced pressure and the residue was taken up in EtOAc. The mixture was filtered and the filtrate was washed with 1N HCl, saturated NaCl, and dried. Removal of solvent under reduced pressure gave a foam, 1.78 g. The structure was confirmed by NMR and mass spectroscopy.

Calcd. for C$_{40}$H$_{49}$N$_3$O$_6$.0.25C$_4$H$_8$O$_2$ (MW 689.84): C, 71.38; H, 7.45; N, 6.09 Found C, 71.03; H, 7.46; N, 6.16.

INTERMEDIATES FOR EXAMPLE 40

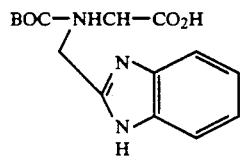

A solution of 5.45 g (19.6 mmole) of 2-(2-benzimidazole) alanine.2HCl (J. Chem. Soc., 1600 (1951)) in 100 ml CH$_2$Cl$_2$ was treated with 4.49 g (20.6 mmole) of di-t-butyldicarbonate and 8.6 ml (61.7 mmole) of Et$_3$N and stirred at room temperature overnight. The solvent was removed under reduced pressure and the residue taken up in 1N NaOH. Adjusting the pH to 3.0 gave a white solid which was collected and washed with H₂O. There was obtained 4.92 g of product, sufficiently pure to use in the following reaction. The structure was confirmed by NMR and mass spectroscopy.

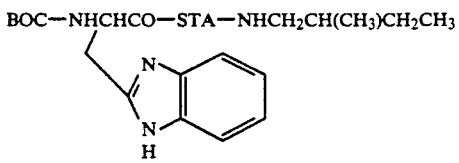

A suspension of 1.09 g (3.56 mmole) of BOC-2-(2-benzimidazole)alanine, 0.5 g (3.74 mmole) of HOBT, and 1.0 g (3.56 mmole) of STA-NHCH₂CH(CH₃)CH₂CH₃·HCl in 15 ml DMF was treated dropwise with Et₃N until solution occurred. The solution was then treated with 0.77 g (3.74 mmole) of DCC and stirred at room temperature overnight. The mixture was filtered and the DMF removed under high vacuum. The residue was taken up in EtOAc and washed with 1N citric acid, saturated NaHCO₃, and saturated NaCl. Drying and removal of the solvent under reduced pressure gave the crude product which was chromatographed on silica gel, eluting with CHCl₃/MeOH (98/2). There was obtained 1.6 g of product sufficiently pure for use in the following step. The structure was confirmed by NMR and mass spectroscopy.

A solution of 1.6 g of

in 20 ml CH₂Cl₂ was treated with 20 ml TFA and allowed to stir at room temperature for two hours. The solvent was removed under reduced pressure and the residue redissolved in CH₂Cl₂ and the solvent removed again. The residue was taken up in EtOAc and washed with 1N NaOH, then saturated NaCl. Drying and removal of the solvent under reduced pressure gave the crude product which was chromatographed on silica gel, eluting with CHCl₃/MeOH (95/5). There was obtained 0.77 g of product of sufficient purity to use in the following step. The structure was confirmed by mass spectroscopy.

INTERMEDIATES FOR EXAMPLE 41

BOC-LYS(TOS)-STA-NHCH₂CH(CH₃)CH₂CH₃

To a solution of 0.72 g (1.83 mmole) of BOC-LYS(-TOS) and 0.3 g (2.1 mmole) of HOBT in 15 ml DMF at −5° was added a solution of 0.56 g (2.0 mmole) of STA-NHCH₂CH(CH₃)CH₂CH₃·HCl and 0.29 ml (2.1 mmole) Et₃N in 20 ml DMF, and the combined solutions treated with 0.43 g (2.1 mmole) DCC. After stirring at room temperature overnight, the mixture was filtered, the solvent removed under high vacuum, and the residue taken up in EtOAc. The solution was washed with 1N citric acid, saturated NaCl, saturated NaHCO₃, and saturated NaCl. After drying, the solvent was removed under reduced pressure and the residue was chromatographed on silica gel, eluting with a gradient of 0 to 5% MeOH in CHCl₃. The product was recovered by combination of the appropriate fractions giving a white foam, 0.80 g, of suitable purity for use in the following reaction. The structure was confirmed by mass spectroscopy.

LYS(TOS)-STA-NHCH₂CH(CH₃)CH₂CH₃

To a solution of 0.80 g (1.3 mmole) of BOC-LYS(-TOS)-STA-NHCH₂CH(CH₃)CH₂CH₃ in 30 ml CH₂Cl₂ was added 15 ml TFA. After stirring at 25° for one and one-half hours the mixture was evaporated to an oil, taken into EtOAc and washed with 5N NaOH, and saturated NaCl. After drying, the solution was evaporated under reduced pressure to a foam, 0.67 g, of sufficient purity for use in the following reaction. The structure was confirmed by mass spectroscopy.

INTERMEDIATE FOR EXAMPLE 42

N-(METHYLOXYCARBONYL)SUCCINIMIDE

To a solution of 19.8 g (200 mmole) of succinimide and 22 ml (200 mmole) of N-methylmorpholine in 350 ml THF at −5° was added 15.5 ml (200 mmole) methylchloroformate over 20 minutes. After stirring for two hours at 25°, the solvent was removed under reduced pressure and the residue was taken up in EtOAc. The suspension was filtered, and washed with saturated NaCl, saturated NaHCO₃, and saturated NaCl. After drying, the solution was concentrated under reduced pressure and Et₂O was added, giving the product as a crystalline solid, 10.0 g. The structure was confirmed by NMR and mass spectroscopy.

INTERMEDIATES FOR EXAMPLE 43

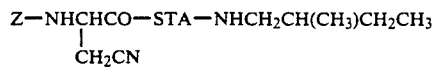

A solution of 1.54 g (6.2 mmole) of (R,S)-Z-β-cyanoalanine (J. Org. Chem. 26, 3356 (1961)) and 0.88 g (6.51 mmole) of HOBT in 5 ml DMF and 45 ml CH₂Cl₂ was cooled in ice and 1.34 g (6.51 mmole) of DCC added, followed by 1.85 g (6.2 mmole) of STA-NHCH₂CH(CH₃)CH₂CH₃·HCl and 1.36 ml (9.7 mmole) of Et₃N. The solution was stirred at room temperature overnight. The mixture was filtered and the solvent removed under reduced pressure. The residue was taken up in EtOAc and washed with 1N citric acid, saturated NaCl, saturated NaHCO₃, and saturated NaCl. Drying and removal of the solvent under reduced pressure gave the crude product which could be crystallized from EtOAc/Et₂O. There was obtained 2.31 g of the product as a white solid. The structure was confirmed by NMR and mass spectroscopy.

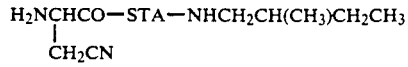

A solution of 2.11 of

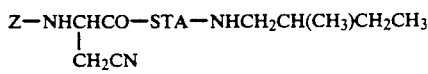

in 80 ml MeOH was treated with 0.2 g of 20% Pd/C and stirred under a hydrogen atmosphere for one and one-half hours. The mixture was filtered and the solvent removed under reduced pressure giving 1.47 g of the product. The structure was confirmed by NMR and mass spectroscopy.

INTERMEDIATES FOR EXAMPLE 44

Z-AMINOMALONIC ACID, METHYL t-BUTYL ESTER

Methyl, t-butyl isonitrosomalonate was prepared from 50 g of methyl, t-butylmalonate by the procedure described in Org. Syn. Coll. Vol. 5, p. 373. The 54 g of crude product thus obtained was reduced to aminomalonic acid methyl, t-butyl ester by the procedure described in J. Am. Chem. Soc., 75, 1970 (1953). To the filtrate of this reaction mixture was added 64.4 g (258 mmoles) N-(benzyloxycarbonyloxy)succinimide. The mixture was stirred overnight at 25°, filtered, and the solvent removed under reduced pressure. The residue was taken up in EtOAc and washed with 1N citric acid, saturated NaCl, saturated NaHCO$_3$, and saturated NaCl. After drying, the solvent was removed under reduced pressure and the residue was chromatographed on silica gel, eluting with hexane/EtOAc (75/25). The appropriate fractions were combined to give an oil, 30.1 g, of sufficient purity for use in the following reaction. The structure was confirmed by NMR and mass spectroscopy.

AMINOMALONIC ACID, METHYL t-BUTYL ESTER

To a solution of 3.23 g (10 mmole) of Z-aminomalonic acid, methyl t-butyl ester in 25 ml THF was added 0.1 g of 20% Pd/C catalyst. The mixture was purged with hydrogen gas over five hours, filtered, and the solvent removed in vacuo giving an oil, 1.79 g, of sufficient purity for use in the next reaction.

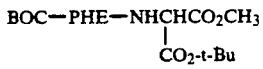

A solution of 2.65 g (10 mmole) of BOC-PHE, 1.39 g (10.3 mmole) of HOBT, and 1.89 g (10 mmole) of aminomalonic acid methyl, t-butyl ester in 80 ml DMF was cooled in ice, and 2.12 g (10.3 mmole) of DCC added. The solution was stirred at 0° for three hours, then at room temperature overnight. The mixture was filtered, and the solvent evaporated under high vacuum. The residue was taken up in EtOAc, and washed with 1N citric acid, saturated NaCl, saturated NaHCO$_3$, and saturated NaCl. The solvent was evaporated under reduced pressure and the residue was chromatographed on silica gel, eluting with hexane/EtOAc (75/25). The appropriate fractions were combined giving a white foam, 3.69 g. The material was sufficiently pure for use in the following reaction. The structure was confirmed by NMR and mass spectroscopy.

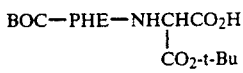

To a solution of 3.44 g (7.88 mmole) of

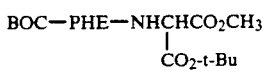

in 20 ml dioxane was added 8.0 ml 1N NaOH. After one hour, 1 ml 1N HCl was added, and the solvent was removed under reduced pressure at 25°. The residue was taken up in EtOAc and washed with 1N citric acid and saturated NaCl. After drying, the solvent was removed under reduced pressure giving a foam, 2.92 g, sufficiently pure for use in the following reaction. The structure was confirmed by NMR and mass spectroscopy.

INTERMEDIATES FOR EXAMPLES 45 AND 87

MALONIC ACID, ETHYL, BENZYL ESTER

To a solution of 17.22 g (114 mmole) of ethyl malonyl chloride in 150 ml THF at 10° was added a solution of 12.19 ml (118 mmole) benzyl alcohol and 16.4 ml (118 mmole) Et$_3$N in 25 ml THF over thirty minutes. The mixture was stirred overnight, filtered, and the solids washed with THF. The filtrate was evaporated under reduced pressure to an oil, taken up in EtOAc, and washed with 1N citric acid, saturated NaCl, saturated NaHCO$_3$, and saturated NaCl. After drying, the solvent was removed at reduced pressure, and the residue was distilled. Collecting the fraction boiling from 118° to 122° at 0.4 mmHg gave the product as an oil, 19.5 g, of sufficient purity for use in the following reaction. The structure was confirmed by NMR and mass spectroscopy.

BOC-AMINOMALONIC ACID, ETHYL, BENZYL ESTER

Ethyl, benzyl isonitrosomalonate was prepared from 19 g of ethyl benzyl malonate by the procedure described in Org. Syn. Coll. Vol. 5, p. 373. The 24.5 g of crude product thus obtained was reduced to aminomalonic acid, ethyl, benzyl ester by the procedure described in J. Am. Chem. Soc., 75, 1970 (1953), and was immediately converted to BOC-aminomalonic acid, ethyl, benzyl ester by the addition of 19.2 g (88 mmole) of di-t-butyldicarbonate to the reduction mixture. The crude product was chromatographed on silica gel, eluting with hexane/EtOAc (75/25), giving an oil 15.54 g. The product was of sufficient purity for use in the following reaction. The structure was confirmed by NMR and mass spectroscopy.

AMINOMALONIC ACID, ETHYL BENZYL ESTER.HCl

A solution of 8.29 g (24.6 mmole) BOC-aminomalonic acid, ethyl benzyl ester in 100 ml CH$_2$Cl$_2$ was purged with HCl gas occasionally over five hours. The solvent was removed under reduced pressure and the residue was triturated with Et$_2$O. After decanting the Et$_2$O, the residue was stripped of volatiles under high vacuum, giving a crystalline solid, 6.5 g, of sufficient purity for use in the following reaction. The structure was confirmed by NMR and mass spectroscopy.

DI-(1-NAPHTHYLMETHYL)ACETYL CHLORIDE

A solution of 14.4 g (42 mmole) of di-(1-naphthylmethyl) acetic acid in 100 ml thionyl chloride was stirred at 22° overnight and the solvent removed under reduced pressure. The resulting solid was recrystallized from Et₂O and hexane, giving the product as a beige solid, 13.5 g of sufficient purity for use in the following reaction.

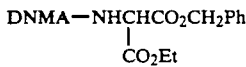

A solution of 3.93 g (11 mmole) of di-(1-naphthylmethyl) acetyl chloride and 3.0 g (11 mmole) of aminomalonic acid, ethyl benzyl ester, hydrochloride in 125 ml THF was cooled to 5° and 3.3 ml (22.6 mmole) Et₃N was added. After stirring overnight at 22°, the mixture was filtered and the solvent removed under reduced pressure. The residue was taken up in EtOAc and washed with 1N citric acid, saturated NaCl, saturated NaHCO₃, and saturated NaCl. After drying, the solvent was removed under reduced pressure and the residue was chromatographed on silica gel, eluting with hexane/EtOAc (60/40). Combination of the appropriate fractions gave the product as a glassy solid, 5.49 g. The structure was confirmed by NMR and mass spectroscopy.

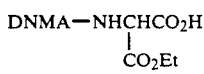

To a solution of 5.3 g (9.47 mmole) of

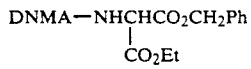

in 100 ml absolute ethanol was added 0.5 g of 20% Pd/C catalyst. The suspension was purged with hydrogen for four hours, filtered, and the solvent removed under reduced pressure giving a white foam, 4.58 g, of sufficient purity for use in the following reaction.

INTERMEDIATES FOR EXAMPLE 47

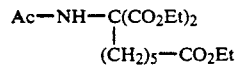

Sodium (2.67 g; 0.116 g.atom) in 115 ml of EtOH was heated until dissolved, and the resulting solution treated dropwise with 26.7 g (0.123 mole) of diethyl acetamidomalonate. The solution was refluxed for one-half hour and then treated dropwise with 25.8 g (0.116 mole) of ethyl 6-bromohexanoate and the resulting solution heated at reflux for eighteen hours. The solution was then filtered and concentrated under reduced pressure. The residue was taken up in Et₂O and washed with H₂O and saturated NaCl. Drying and removal of the solvent under reduced pressure gave 40.4 g of the product as an oil, sufficiently pure to use in the following reaction.

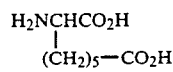

A solution of 39.8 g (0.11 mole) of

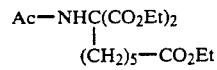

in 200 ml of 6N HCl was heated at reflux for four days. After cooling the solution was brought to pH 3 with concentrated NH₄OH, and the resulting solid collected and recrystallized from boiling H₂O to give 11.5 g of the product as a white solid, mp 246°-248°.

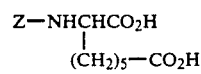

A solution of 40.2 g (0.21 mole) of

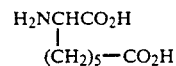

in 470 ml of 1.8M NaOH was cooled in ice and treated dropwise over twenty minutes with 46.8 ml (0.32 mole) of benzyl chloroformate. After four hours at 0°, the solution was allowed to stir at room temperature overnight. The solution was washed with Et₂O and then brought to pH 2. This solution was extracted with Et₂O and the Et₂O dried and concentrated under reduced pressure. There was obtained 14.48 g of the product as a white solid, mp 112°-115°.

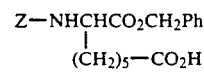

A solution of 16.45 g (0.051 mole) of

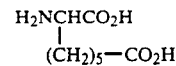

in 10 ml DMF was treated with 5.14 g (0.051 mole) of Et₃N followed by 10.4 g (0.061 mole) of benzyl bromide. The solution was stirred at room temperature overnight, then diluted with H₂O and extracted with EtOAc. The EtOAC was washed with 5% NaHCO₃, the NaHCO₃ acidified to pH 2, and extracted with EtOAc. The EtOAc was dried and the solvent removed under reduced pressure to give 8.53 g of the product, mp 75°-75°.

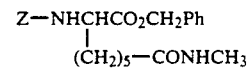

A solution of 2.5 g (6.0 mmole) of

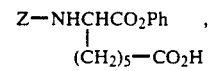

0.41 g (6.0 mmole) of methylamine, hydrochloride, and 0.82 g (6.0 mmole) of HOBT in 30 ml DMF was cooled in ice and 0.61 g (6.0 mmole) Et₃N added followed by 1.24 g (6.0 mmole) of DCC in 10 ml DMF and the solution stirred at room temperature overnight. The mixture was filtered and the solvent removed under high vacuum. The residue was taken up in EtOAc, filtered, and washed with 1N HCl, saturated NaHCO₃, and saturated NaCl. Drying and removal of the solvent under reduced pressure gave the crude product which was chromatographed on silica gel, eluting with CHCl₃/MeOH (97/3). There was obtained 2.04 g of the product as a white foam.

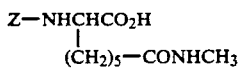

A solution of 1.54 g (3.6 mmole) of

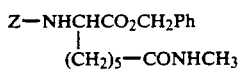

in 30 ml MeOH was treated with 288 mg (7.2 mmole) of NaOH in 5 ml H₂O and the solution stirred at room temperature for one and one-half days. The solvent was removed under reduced pressure and the residue taken up in CH₂Cl₂ and washed with 1N HCl, then saturated NaCl. Drying and removal of the solvent under reduced pressure gave the crude product which was chromatographed on silica gel, eluting with EtOAc, then MeOH. There was obtained 0.89 g of the product as an oil which crystallized on standing.

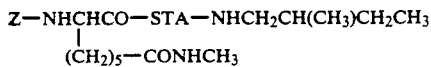

A solution of 0.71 g (2.2 mole) of

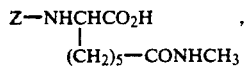

0.57 g (2.2 mmole) of STA-NHCH₂CH(CH₃)CH₂CH₃, and 0.3 g (2.2 mmole) of HOBT in 30 ml DMF was cooled in ice and 0.45 g (2.2 mmole) of DCC added, and the solution allowed to stir at room temperature overnight. The mixture was filtered and the solvent removed under high vacuum. The residue was taken up in EtOAc and washed with 1N HCl, saturated NaHCO₃, and saturated NaCl. Drying and removal of the solvent under reduced pressure gave 0.69 g of the product as a white foam.

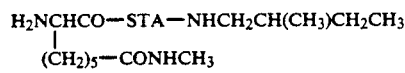

A solution of 0.54 g of

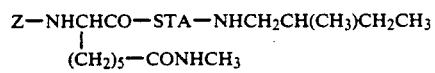

in 250 ml MeOH was treated with 0.5 g of 20% Pd/C and stirred under hydrogen for two hours. The mixture was filtered and the solvent removed under reduced pressure given 0.43 g of the product as a colorless gum, sufficiently pure for use in the following reaction.

INTERMEDIATES FOR EXAMPLES 48 AND 49

To a solution of 14.5 g (0.053 mole) of α-BOC-aminomalonic acid, diethyl ester in 100 ml EtOH was added 25.6 g (0.079 mole) of a 21% solution of NaOEt in EtOH, followed by 9.37 ml (0.079 mole) of 5-bromo-1-pentene. The solution was refluxed under a nitrogen atmosphere for twenty hours, and was then concentrated under reduced pressure. The residue was diluted with Et₂O, washed with H₂O and saturated NaHCO₃, dried, and concentrated under reduced pressure to give 14.7 g of the product as an orange oil. The structure was confirmed by NMR spectroscopy.

BOC-NHCH(CH₂CH₂CH₂CH=CH₂)CO₂H

To a solution of 12.8 g (0.037 mole) of BOC-NHC(CH₂CH₂CH₂CH=CH₂)(CO₂Et)₂ in 100 ml of THF was added 112 ml 0.112 mole) of 1N NaOH and 30 ml EtOH. The solution was refluxed for fifteen hours, cooled, and concentrated under reduced pressure. The residue was diluted with EtOAc, washed with H₂O, dried, and concentrated under reduced pressure to an oil. This was dissolved in 200 ml xylene and heated at reflux for two hours. The organic solution was washed with saturated NaHCO₃, acidified to pH 3 with solid citric acid, and extracted with EtOAc. After drying, removal of the solvent under reduced pressure gave 6.85 g of the product as a white solid. The structure was confirmed by NMR spectroscopy.

BOC-NHCH(CH₂CH₂CH₂CH=CH₂)CO-STA-LEU-NHCH₂Ph

To a solution of 2.46 g (10.1 mmole) of BOC-NHCH(CH₂CH₂CH₂CH=CH₂)CO₂H and 3.82 g (10.1 mmole) of STA-LEU-NHCH₂Ph in 50 ml of CH₃CN was added 1.43 g (10.6 mmole) of HOBT followed by 2.19 g (10.6 mmole) of DCC. The mixture was stirred for two days at room temperature and filtered. The filtrate was concentrated and diluted with EtOAc. The organic layer was washed with saturated NaHCO₃, H₂O, and 10% citric acid solution. Drying and removal of the solvent under reduced pressure gave 5.7 g of the product. The structure was confirmed by NMR spectroscopy.

H₂NCH(CH₂CH₂CH₂CH=CH₂)CO-STA-LEU-NHCH₂Ph

To a solution of 5.5 g (9.61 mmole) of BOC-NHCH(CH₂CH₂CH₂CH=CH₂)CO-STA-LEU-NHCH₂Ph in 200 ml of CH₂Cl₂ was added 200-ml TFA, and the solution stirred at room temperature for one hour. The solvent was removed under reduced pressure and the residue taken up in EtOAc and washed with saturated NaHCO₃. After drying and removal of the solvent under reduced pressure there was obtained 4.9 g of the product. The structure was confirmed by NMR spectroscopy.

INTERMEDIATES FOR EXAMPLES 52-54

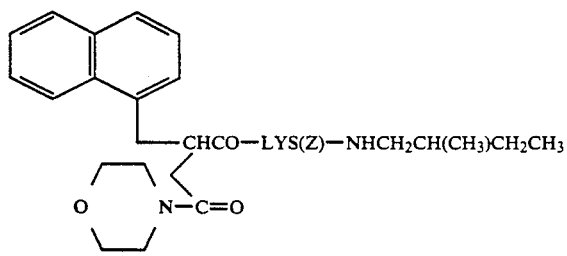

Using the procedure described for preparing intermediates for Example 2, but substituting

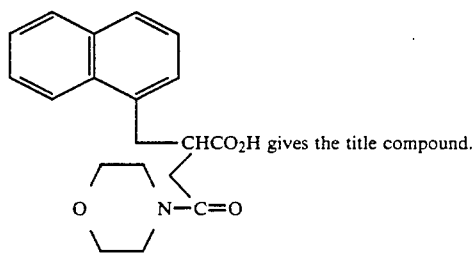

Treatment of

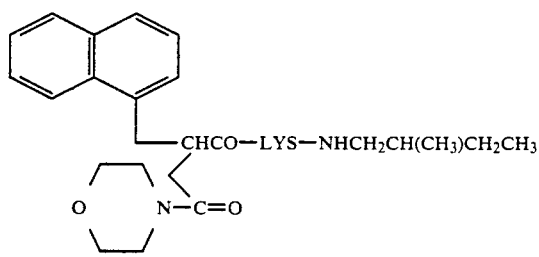

with hydrogen in the presence of Pd/C in MeOH gives the title compound.

INTERMEDIATES FOR EXAMPLE 55

BOC-AMINOMALONIC ACID, ISOPROPYL BENZYL ESTER

Following the procedure for intermediates for Example 45 but substituting ISOPROPYL, BENZYL MALONATE for ETHYL BENZYL MALONATE gave 12.2 g of the title compound as an oil. The structure was confirmed by NMR and mass spectroscopy.

AMINOMALONIC ACID, ISOPROPYL BENZYL ESTER.HCl

Treatment of BOC-AMINOMALONIC ACID, ISOPROPYL BENZYL ESTER with HCl gas in $CH_2Cl_2$ according to the procedure described for the intermediates for Example 45 gave 9.37 g of the title compound as a white solid. The structure was confirmed by NMR and mass spectroscopy.

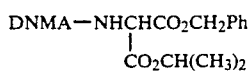

Following the procedure described in the intermediate for Example 45 but substituting AMINOMALONIC ACID, ISOPROPYL BENZYL ESTER.HCl for AMINOMALONIC ACID, ETHYL BENZYL ESTER.HCl gave 5.83 g of the title compound. The structure was confirmed by NMR and mass spectroscopy.

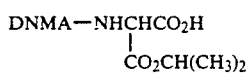

Treatment of

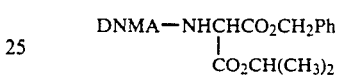

with hydrogen in the presence of 20% Pd/C according to the procedure described in the intermediates for Example 45 gave 4.69 g of the title compound as a white foam. The structure was confirmed by NMR and mass spectroscopy.

INTERMEDIATES FOR EXAMPLES 56 AND 57

$$ClCH_2C\equiv C-CH_2NHCOCH_3$$

A suspension of 8.5 g (0.06 mole) of $ClCH_2C\equiv C-CH_2NH_2 \cdot HCl$ in 10 ml $H_2O$ was treated with 5.8 ml (0.06 mole) of acetic anhydrid, then 8.3 g (0.06 mole) of $NaOAc \cdot 3\ H_2O$. Solution occurred and the solution was stirred for 1.5 hours. The solution was washed twice with EtOAc, and the EtOAc washed twice with saturated $NaHCO_3$. Drying and removal of the solvent under reduced pressure gave the product as an oil which solidified on standing. The structure was confirmed by NMR and mass spectroscopy. The material was sufficiently pure for use in the following step.

DNMA-NHCH(CO$_2$C$_2$H$_5$)$_2$

A suspension of 4.13 g (0.0195 mole) of diethyl aminomalonate.HCl in 100 ml of $CH_2Cl_2$ was treated with 7.0 g (0.0195 mole) of DNMA-Cl and cooled in ice. This was then treated dropwise with 5.5 ml (0.039 mole) of $Et_3N$, and the mixture allowed to stir at room temperature overnight. $Et_3N \cdot HCl$ was filtered off and the solvent removed under reduced pressure. The residue was taken up in EtOAc and washed with 1N HCl, $H_2O$, saturated $NaHCO_3$, and saturated NaCl. Drying and removal of the solvent under reduced pressure gave 9.26 g of the product, mp 118°–120°. The structure was confirmed by NMR and mass spectroscopy.

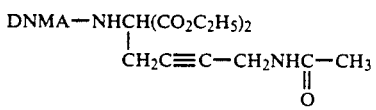

Under a nitrogen atmosphere, 0.44 g (9.0 mmole) of NaH.oil (50%) was washed free of the oil with hexane, then suspended in 25 ml of DMSO. 4.5 g (9.0 mmole) of DNMA-NHCH(CO₂C₂H₅)₂ was added in portions and the solution stirred for 2 hours, at which time hydrogen evolution had ceased. 1.32 g (9.0 mmole) of ClCH₂C≡C—CH₂NHCOCH₃ was then added, followed by 1.0 g of KI. After stirring for three days, the mixture was diluted with EtOAc and washed twice with H₂O, saturated NaHCO₃, then saturated NaCl. Drying and removal of the solvent under reduced pressure gave the crude product. Chromatography on silica gel, eluting with CHCl₃/MeOH (99/1) gave 3.8 g of product sufficiently pure for use in the following step. The structure was confirmed by mass spectroscopy.

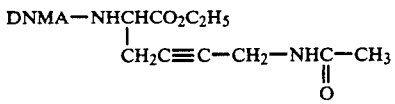

A solution of 3.08 g (5.1 mmole) of

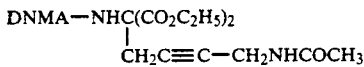

in 35 ml MeOH was treated with 0.47 g (11.8 mmole) of NaOH in 10 ml H₂O and stirred for 3.5 hours. The MeOH was removed under reduced pressure and the residue diluted with H₂O. After extracting with Et₂O the pH was adjusted to 2.0 with dilute HCl, and extracted twice with EtOAc. The EtOAc was washed with saturated NaCl, dried, and stripped. The residue was taken up in 50 ml toluene and heated at reflux for 2 hours. On cooling a solid separated. The mixture was dilute with hexane and 1.89 g of the product collected. The structure was confirmed by NMR spectroscopy. The material was sufficiently pure for use in the following step.

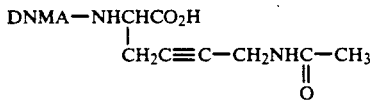

A solution of 1.89 g (3.6 mmole) of

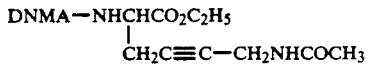

in 20 ml dioxane and 20 ml MeOH was treated with 0.2 g (5.0 mmole) of NaOH in 10 ml H₂O and the solution stirred at room temperature for 2 hours. The solvent was removed under reduced pressure and the residue diluted with H₂O. Acidifying with dil. HCl to pH 2 caused a solid to precipitate. There was obtained 1.7 g of the product, mp 218°-222°. The structure was confirmed by mass spectroscopy.

INTERMEDIATES FOR EXAMPLE 59

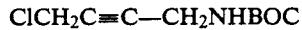

A suspension of 2.89 g (20.6 mmole) of ClCH₂C≡C—CH₂NH₂.HCl in 30 ml of dioxane was cooled in ice and 4.5 g (20.6 mmole) of di-tert-butyldicarbonate added, followed by 10.4 ml (20.8 mmole) of 2N NaOH. The cooling was removed and the solution allowed to stir at room temperature for 2 hours. The solution was diluted with EtOAc and the layers separated. The EtOAc layer was washed with H₂O, 1N citric acid, H₂O, saturated NaHCO₃, and saturated NaCl. Drying and removal of the solvent under reduced pressure left 4.2 g of the product. The material was of sufficient purity for use in the following step.

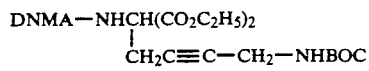

Under a nitrogen atmosphere, 1.7 g (34.9 mmole) of NaH.oil (50%) was washed free of the oil with hexane, then suspended in 100 ml of DMSO. 17.38 g (34.9 mmole) of DNMA-NHCH(CO₂C₂H₅)₂ was added in portions and the solution stirred for 3 hours, at which time hydrogen evolution had ceased. A solution of 8.0 g (34.9 mmole) of ClCH₂C≡C—CH₂NHBOC in 20 ml DMSO was added together with 2.0 g of KI, and the solution stirred at room temperature for 3 days. The mixture was diluted with EtOAc and washed two times with H₂O, then saturated NaHCO₃, then saturated NaCl. Drying and removal of the solvent under reduced pressure gave the crude product which was purified by chromatography on silica gel, eluting with CHCl₃. There was obtained 6.2 g of product. The structure was confirmed by mass spectroscopy.

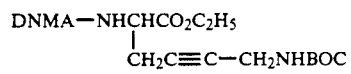

A solution of 6.2 g (9.3 mmole) of

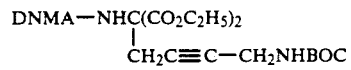

in 40 ml EtOH and 40 ml dioxane was treated with a solution of 0.9 g (22.5 mmole) of NaOH in 18 ml H₂O and stirred at room temperature overnight. The solvent was removed under reduced pressure and the residue taken up in H₂O. The solution was brought to pH 2 and extracted twice with EtOAc. The EtOAc was washed with saturated NaCl, dried, and the solvent removed under reduced pressure. The residue was taken up in 85 ml dioxane and 85 ml toluene and heated at reflux for 3 hours. Cooling and removal of the solvent under reduced pressure left 6.13 g of the crude product. Thin layer chromatography showed that both the product and the corresponding acid were present. The mixture was used directly in the following step.

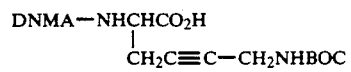

A solution of 6.13 g (15.6 mmole) of

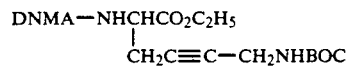

in 50 ml dioxane and 20 ml MeOH was treated a solution of 0.7 g (17.5 mmole) of NaOH in 20 ml H₂O and stirred at room temperature for 3 hours. The solvent was removed under reduced pressure and the residue taken up in H₂O. The pH was brought to 2 and the mixture extracted twice with EtOAc. The EtOAc was washed with saturated NaCl, dried, and the solvent removed under reduced pressure leaving 5.0 g of the product. The structure was confirmed by NMR spectroscopy. The material was sufficiently pure for use in the next reaction.

INTERMEDIATE FOR EXAMPLES 60–63

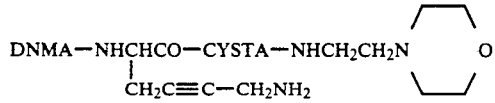

A solution of 3.5 g (4.0 mmole) of

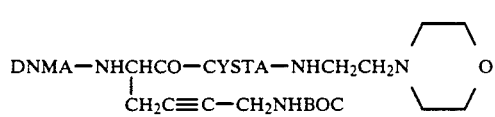

in 75 ml of CH₂Cl₂ was treated with HCl gas and allowed to stir for 1 hour. HCl gas was again bubbled in and the solution allowed to stir an additional hour. The solution was concentrated under reduced pressure, CH₂Cl₂ added, and the solution concentrated again. The residue was taken up in CH₂Cl₂ and treated with CH₂Cl₂ which had been saturated with NH₃ gas. The NH₄Cl was filtered off and the filtrate concentrated under reduced pressure to give 2.8 g of the product as a foam. The material was sufficiently pure for use in the following steps.

INTERMEDIATES FOR EXAMPLE 64

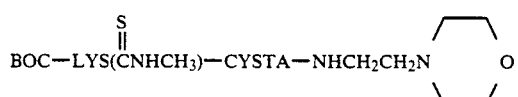

To a solution of 1.5 g (2.7 mmole) of

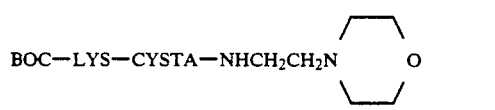

in 50 ml CH was added 0.41 ml (2.97 mmole) of Et₃N followed by the dropwise addition of a solution of 220 mg (2.97 mmole) of methyl isothiocyanate in 20 ml CH₂Cl₂. After stirring at room temperature for 16 hours, the solvent was removed under reduced pressure and the residue chromatographed on silica gel, eluting with a gradient of 2–8% MeOH in CHCl₃. There was obtained 1.41 g of product. The structure was confirmed by NMR and mass spectroscopy.

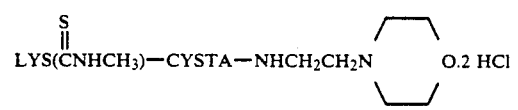

A solution of 1.41 g (2.23 mmole) of

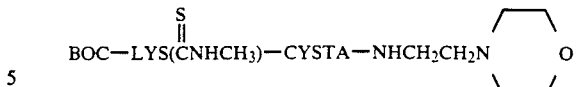

in 50 ml of CH₂Cl₂/MeOH (2/1) was cooled to 0° and HCl gas bubbled into the solution for 10 minutes. The solvent was removed under reduced pressure and the residue taken up in toluene and the solvent again removed under reduced pressure to give 1.34 g of the product.

INTERMEDIATES FOR EXAMPLES 68–70

S-CYCLOHEXYLGLYCINE, METHYL ESTER, HYDROCHLORIDE

A solution of 3.74 g of phenylglycine, methyl ester, hydrochloride in 100 ml MeOH containing 1.0 g of 10% Rh/C was shaken in an atmosphere of hydrogen until the hydrogen uptake was complete. The mixture was filtered and the solvent removed under reduced pressure to give 3.7 g of the product. The material was sufficiently pure for use in the following step.

S-N-(2-CARBOXYACETYL)CYCLOHEXYLGLYCINE, METHYL ESTER

A solution of 2.7 g (18 mmole) of ethylmalonyl chloride in 7 ml of CH₂Cl₂ was added dropwise to a cold solution of 3.74 g (18 mmole) of S-cyclohexylglycine, methyl ester, hydrochloride containing 4.0 ml of Et₃N. The solution was stirred for 4 hours at room temperature, then poured into H₂O, and the organic phase separated. The organic phase was washed with brine, dried, and the solvent removed under reduced pressure to give 3.48 g of the product as a tan solid. The material was sufficiently pure to use in the following step.

S-3-ETHOXYCARBONYL-4-HYDROXY-5-CYCLOHEXYL-3-PYRROLIDINE-2-ONE

A solution of 3.9 g (12 mmole) of NaOEt in 8 ml of EtOH was added to a solution of 3.48 g (12 mmole) of S-N-(2-carboxyacetyl)cyclohexylglycine, methyl ester in 8 ml of EtOH and the solution stirred at room temperature for 2 hours. The precipitated solid was collected and washed with Et₂O. The solid was dissolved in H₂O, the pH brought to 2.0, and the mixture extracted with EtOAc. The EtOAc was dried and the solvent removed under reduced pressure leaving 2.0 g of the product. The material was sufficiently pure for use in the following step.

S-5-CYCLOHEXYL-2,4-PYRROLIDINEDIONE

A solution of 2.0 g of S-3-ethoxycarbonyl-4-hydroxy-5-cyclohexyl-3-pyrrolidine-2-one in 2 ml of EtOH was added all at once to a boiling solution of EtOH/H₂O (1:1) with vigorous stirring. Refluxing was continued for 10 minutes at which time CO₂ evolution had ceased. The solution was cooled, saturated with NaCl, and extracted three times with EtOAc. Drying and removal of the solvent under reduced pressure gave the crude product. This was taken up in EtOAc and filtered through a plug of silica gel to give 0.8 g of the product, $[\alpha]_D^{23} -68°$ (C, 1.08, CHCl₃).

Calcd. for C₁₀H₁₅NO₂ (MW 181.23): C, 66.30; H, 8.28; N, 7.73 Found C, 66.31; H, 8.64; N, 7.66.

S,S-4-HYDROXY-5-CYCLOHEXYL-2-PYRROLIDONE

A solution of 0.8 g of S-5-cyclohexyl-2,4-pyrrolidinedione in 100 ml EtOH was treated with 0.5 g of Raney nickel and stirred under hydrogen at 50 psi. After hydrogen uptake had ceased, the mixture was filtered and the filtrate evaporated under reduced pressure. The residue was triturated with EtOAc to give 0.6 g of the product, mp 145°-156°; $[\alpha]_D^{23} -5.24°$ (C, 1.05, CHCl$_3$).

Calcd. for $C_{10}H_{17}NO_2$ (MW 183.24): C, 65.57; H, 9.29; N, 7.65 Found C, 65.00; H, 9.49; N, 7.25.

S,S-4-(2-TETRAHYDROPYRANYL)OXO-5-CYCLOHEXYL-2-PYRROLIDONE

A solution of 14.1 g (77 mmole) of S,S-4-hydroxy-5-cyclohexyl-2-pyrrolidone, 7.8 ml (84 mmole) of dihydropyran, and 0.5 g p-toluenesulfonic acid in 320 ml of CH$_2$Cl$_2$ was stirred overnight at room temperature. The solution was then washed twice with saturated NaHCO$_3$, then H$_2$O. Drying and removal of the solvent under reduced pressure gave the crude product. Trituration with hexane gave 15.2 g of product, mp 135°-140°; $[\alpha]_D^{23} +11°$ (C, 0.28, CHCl$_3$).

Calcd. for $C_{15}H_{25}NO_3$ (MW 267.36): C, 67.42; H, 9.36; N, 5.24 Found C, 67.34; H, 9.45; N, 5.56.

RS,S,S-4-(2-TETRAHYDROPYRANYL)OXY-5-CYCLOHEXYL-N-BOC-2-PYRROLIDONE

A solution of 15.2 g (57 mmole) of S,S-4-(2-tetrahydropyranyl)oxo-5-cyclohexyl-2-pyrrolidone and 24.8 g (114 mmole) of di-tert-butyldicarbonate in 300 ml of THF was treated with 6.7 g (57 mmole) of DMAP and stirred at room temperature for 24 hours. The solvent was removed under reduced pressure and the residue chromatographed on silica gel, eluting with hexane/EtOAc (2/1). There was obtained 20.6 g of product, $[\alpha]_D^{23} +55°$ (C, 1.3, CHCl$_3$).

Calcd. for $C_{20}H_{33}NO_5$ (MW 367.47): C, 65.39; H, 8.99; N, 3.81 Found C, 65.58; H, 9.14; N, 3.84.

CHSTA-NHCH$_2$CH(CH$_3$)CH$_2$CH$_3$

A solution of 5.5 g (14.5 mmole) of RS,S,S-4-(2-tetrahydropyranyl)oxo-5-cyclohexyl-N-BOC-2-pyrrolidone and 2.1 g (17.5 mmole) of S-2-methylbutylamine in 12.5 ml of Et$_3$N was heated at reflux under nitrogen for 6 hours. The solvent was removed under reduced pressure to give 7.6 g of a viscous oil.

Part of this oil (1.4 g) was dissolved in 35 ml of CH$_2$Cl$_2$ and treated with a 10% solution of HCl gas in EtOH. After stirring for 4 hours, the solvent was removed under reduced pressure. The residue was taken up in 0.5N HCl and washed with Et$_2$O. The solution was made basic and extracted five times with Et$_2$O. Drying and removal of the solvent under reduced pressure gave a gum which was triturated with hexane/Et$_2$O to give 0.4 g of the product. The material was sufficiently pure to use in the next reaction.

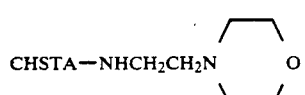

Replacing S-2-methylbutylamine with 4-(2-aminoethyl) morpholine and following the procedure outlined in the previous example gave the title compound. The structure was confirmed by NMR and mass spectroscopy.

INTERMEDIATES FOR EXAMPLE 70

DNMA-LYS(Z)-CHA-NHCH$_2$CH(CH$_3$)CH$_2$CH$_3$

Following the same procedure as in Example 68 and replacing

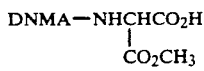

with DNMA-LYS(Z) gave the title compound. The structure was confirmed by NMR and mass spectroscopy.

DNMA-LYS-CHSTA-NHCH$_2$CH(CH$_3$)CH$_2$CH$_3$

A solution of 2.5 g of DNMA-LYS(Z)-CHSTA-NHCH$_2$CH(CH$_3$)CH$_2$CH$_3$ in 100 ml MeOH was treated 0.2 g of 20% Pd/C and stirred in a hydrogen atmosphere until thin layer chromatography showed the complete removal of the Z-group. The mixture was filtered and the filtrate evaporated under reduced pressure to give 1.7 g of product. The structure was confirmed by NMR and mass spectroscopy.

INTERMEDIATES FOR EXAMPLES 71-73

A solution of 7.9 g (21.9 mmole) of

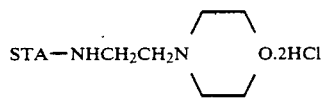

in 80 ml of DMF was cooled in ice and treated with 9.74 ml (54.8 mmole) of diisopropylethylamine, 3.11 g (23 mmole) of HOBT, 8.34 g (21.9 mmole) of BOC-LYS(Z), and 4.8 g (23 mmole) of DCC. After 3 hours at 0°, the mixture was allowed to stir at room temperature overnight. The mixture was filtered and the filtrate concentrated under high vacuum. The residue was taken up in EtOAc and washed with saturated NaHCO$_3$, then brine. Drying and removal of the solvent under reduced pressure gave the crude product which was chromagraphed on silica gel, eluting with a gradient of 5-10% MeOH in CHCl$_3$. There was obtained 6.33 g of the product as a white solid. The structure was confirmed by NMR and mass spectroscopy.

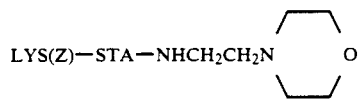

A solution of 6.3 q (9.7 mmole) of

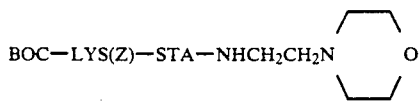

in 100 ml of CH$_2$Cl$_2$ was cooled in ice and 10 ml of TFA added. After stirring for 8 hours at room temperature the solvent was removed under reduced pressure and the residue taken up in EtOAc and washed with saturated NaHCO$_3$. The NaHCO$_3$ layer was back extracted three times with EtOAc. The EtOAc layers were combined, dried, and concentrated to give 1.86 g of the product. The structure was confirmed by NMR and mass spectroscopy.

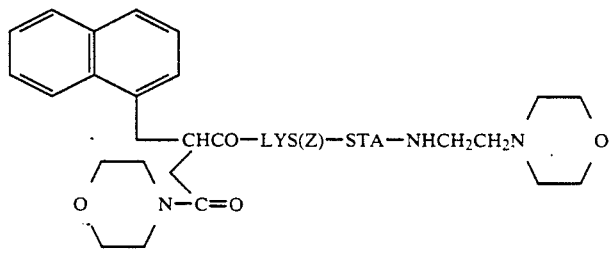

A solution of 1.17 g (3.2 mmole) of

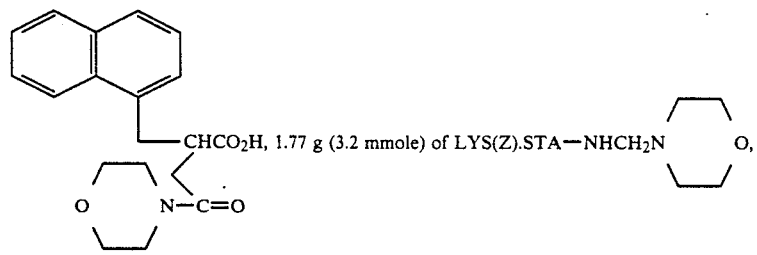

0.63 ml (3.5 mmole) of diisopropylethylamine, and 0.457 g (3.4 mmole) of HOBT in 20 ml DMF was cooled in ice and 0.705 g (3.4 mmole) of DCC added. After 3 hours at 0°, the mixture was allowed to stir at room temperature overnight. The mixture was then filtered and the filtrate concentrated under high vacuum. The residue was taken up in EtOAc, washed with saturated NaHCO$_3$, dried, and the solvent removed under reduced pressure giving the crude product. Chromatography on silica gel, eluting with a gradient of 5–10% MeOH in CHCl$_3$ gave 1.96 g of the product. The structure was confirmed by NMR and mass spectroscopy.

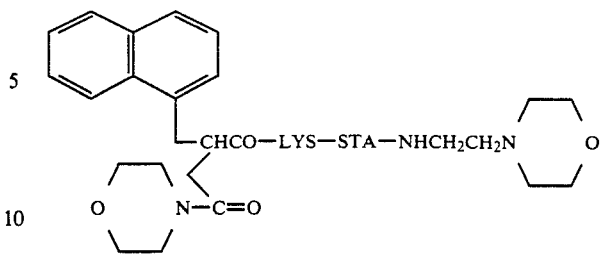

a solution of 2.5 g (2.91 mmole) of

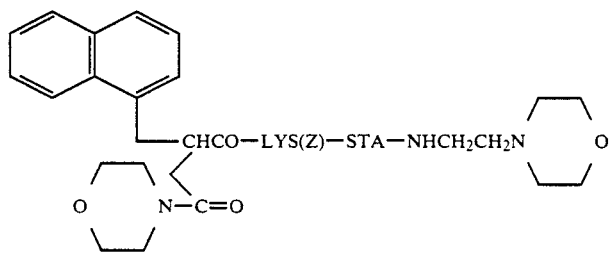

in 40 ml MeOH was treated with 0.7 g of 20% Pd/C and stirred overnight in a hydrogen atmosphere. The mixture was filtered and the filtrate evaporated under reduced pressure to give 2.14 g of the product. The structure was confirmed by NMR and mass spectroscopy.

INTERMEDIATES FOR EXAMPLES 74, 75 AND 88

To a solution of 33.6 g (0.126 mole) of Z-ASN in 250 ml pyridine was added 27.5 g (0.133 mole) of DCC and the solution stirred at room temperature for 24 hours. The solid was removed by filtration and the filtrate evaporated in vacuo to give an oil. The oil was taken up in 500 ml of H$_2$O and filtered free of solids. The filtrate was brought to pH 3 and cooled. The precipitated solid was collected to give 20.6 g of product, $[\alpha]_D^{23} -15.17°$ (C, 0.745, MeOH). The structure was confirmed by NMR and mass spectroscopy.

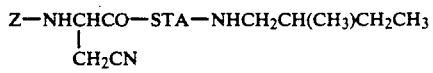

A solution of 2.98 g (12 mmole) of

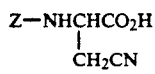

in 25 ml DMF was cooled in ice and 1.64 g (12.1 mmole) of HOBT and 2.49 g (12.1 mmole) of DCC added. After stirring for 5 minutes, 3.0 g (12.3 mmole) of STA—NHCH$_2$CH(CH$_3$)CH$_2$CH$_3$ was added and the solution stirred for 2 hours at 0°, then at room temperature overnight. The mixture was filtered and the solvent removed in vacuo. The residue was taken up in warm EtOAc and washed with 1N citric acid, saturated NaHCO$_3$, then brine. Drying and removal of the solvent under reduced pressure gave a solid which was triturated with Et$_2$O to give 4.5 g of the product. The structure was confirmed by NMR and mass spectroscopy.

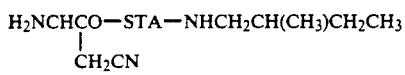

A solution of 3.6 g (7.5 mmole) of

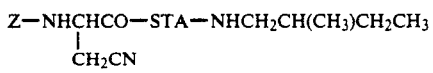

in 60 ml MeOH was treated with 0.36 g of 5% Pd/C and stirred under a hydrogen atmosphere for 1.5 hours. The mixture was filtered and the solvent removed under reduced pressure to give 2.5 g of product of sufficient purity for use in the next reaction. The structure was confirmed by NMR and mass spectroscopy.

INTERMEDIATES FOR EXAMPLES 76 AND 77

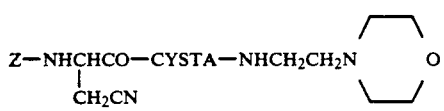

To a solution of 3.0 g (12 mmole) of

in 30 ml DMF at 0° was added successively 1.62 g (12 mmole) of HOBT, 2.48 g (12 mmole) of DCC and 3.93 g (12 mmole) of

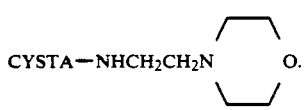

After stirring at 0° for 1 hour, the mixture was stirred at room temperature overnight. The mixture was filtered and the DMF removed under high vacuum leaving an oil. Trituration with EtOAc/Et$_2$O gave a solid which was recrystalized from EtOAc. There was obtained 5.1 g of product. The structure was confirmed by NMR and mass spectroscopy.

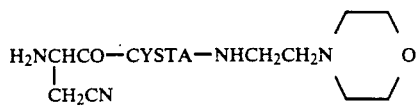

A solution of 4.6 g (8.25 mmole) of

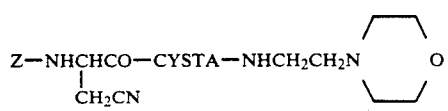

in 25 ml MeOH was treated with 0.46 g of 5% Pd/C and stirred under a hydrogen atmosphere for 6 hours. The mixture was filtered and the solvent removed under reduced pressure to give 3.4 g of product. The structure was confirmed by NMR and mass spectroscopy. The material was sufficiently pure for use in the following step.

INTERMEDIATES FOR EXAMPLES 64, 78, AND 79

A solution of 6.36 g BOC-LYS(Z) and 2.3 g HOBT in 30 ml DMF was cooled to 15° and 3.5 g DCC was added. After stirring for 15 minutes, this was treated with a solution of 5.5 g

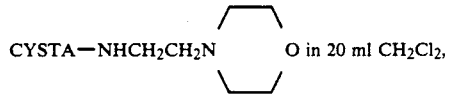

and stirring at room temperature continued for 2 days. The mixture was then filtered and the solvent removed in vacuo. The residue was taken up in CH$_2$Cl$_2$ and washed with 5% K$_2$CO$_3$. The organic layer was dried and concentrated under reduced pressure until crystallization gave a thick slurry. This was diluted with Et$_2$O and the solid collected giving 10.1 g of the product.

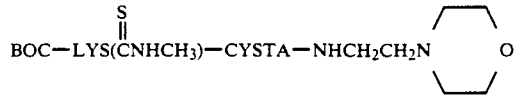

A solution of

in 200 ml MeOH was treated with 0.55 g of 20% Pd/C and stirred under an atmosphere of hydrogen for 2 hours. The mixture was then filtered and the filtrate treated with 1.1 g of methyl isothiocyanate and stirred at room temperature for 18 hours. Evaporation of the solvent under reduced pressure gave the crude product which was purified by chromatography on silica gel, eluting with $CHCl_3/MeOH$ (96/4). The structure was confirmed by mass spectroscopy.

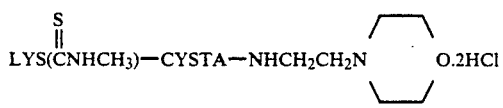

A solution of 9.0 g of

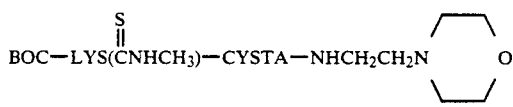

in 250 ml $CH_2Cl_2$ was treated with 200 ml of freshly prepared methanolic HCl. The resulting solution was stirred at room temperature for 3 hours and then evaporated. The residue was dissolved in 35 ml of MeOH and added to 900 ml of $Et_2O$ with vigorous stirring. The precipitate was collected and washed with $Et_2O$ giving 8.58 g of the product. The structure was confirmed by mass spectroscopy.

The free base could be generated by treating the dihydrochloride with ammonia in $CH_2Cl_2$, filtering to remove the $NH_4Cl$, and evaporating the filtrate.

INTERMEDIATES FOR EXAMPLE 83

A solution of 33.27 g (0.094 mole) of $BrCH_2CH=CHCH_2$ ($C_6H_{12}N_4$)Br [from $BrCH_2CH=CHCH_2Br$ (trans) and hexamethylenetetramine] in 65 ml 95% EtOH and 25 ml concentrated HCl was warmed to 100° for 10 minutes. The mixture was cooled and the white solid filtered off and discarded. The filtrate was evaporated and the residue taken up in 30 ml 95% EtOH and 10 ml concentrated HCl and again heated to 100° for 10 minutes. Work-up as before and then resubjecting the residue to the EtOH/HCl treatment finally gave 12.17 g of the crude product, sufficiently pure for use in the following reaction.

A suspension of 8.0 g (0.043 mole) of the crude $BrCH_2CH=CHCH_2NH_2.HCl$ in 200 ml $CH_2Cl_2$ was treated with 5.98 ml (0.043 mole) of $Et_3N$ followed by 9.28 g (0.043 mole) of di-tert-butyldicarbonate and the solution stirred overnight. The mixture was then filtered and the solvent removed under reduced pressure. The residue was taken up in EtOAc and washed with 0.5N HCl, $H_2O$, saturated $NaHCO_3$, and saturated NaCl. Drying and removal of the solvent under reduced pressure left the crude product which was chromatographed on silica gel, eluting with $CHCl_3/MeOH$ (9/1). Thee was obtained 1.7 g of product. The structure was confirmed by NMR and mass spectroscopy.

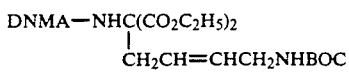

To a solution of 382 mg (9.54 mmole) of NaH.oil (50%) [washed free of the oil with petroleum ether] in 10 ml of DMSO was added in portions a solution of 3.8 g (7.63 mmole) of $DNMA-NHCH(CO_2C_2H_5)_2$ in 30 ml DMSO. The mixture was stirred for 1.5 hours then treated with a solution of 1.9 g (7.63 mmole) of $BrCH_2CH=CHCH_2NHBOC$ in 30 ml DMSO followed by 0.76 g of KI. The mixture was stirred for 60 hours, diluted with EtOAc, and washed twice with $H_2O$, saturated $NaHCO_3$, then saturated NaCl. Drying and removal of the solvent under reduced pressure left an oil which was chromatographed on silica gel, eluting with EtOAc/petroleum ether (25/75). There was obtained 3.7 g of the product as a colorless oil. The structure was confirmed by NMR and mass spectroscopy.

Calcd. for $C_{40}H_{46}N_2O_7$ (MW 666.82): C, 72.05; H, 6.95; N, 4.20 Found C, 71.87; H, 6.94; N, 3.94.

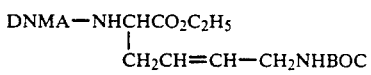

A solution of 1.0 g (1.5 mmole) of

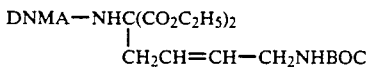

in 15 ml MeOH was treated with a solution of 0.15 g NaOH in 4 ml $H_2O$ and stirred at room temperature for 4 hours. The solution was diluted with $H_2O$ and washed with $Et_2$. The aqueous layer was brought to pH 2 with dilute HCl, and was then extracted three times with EtOAc. The EtOAc was washed with saturated NaCl, dried, and the solvent removed under reduced pressure to give 0.71 g of a white foam. This was taken up in 30 ml of toluene and refluxed for 1.5 hours. The solvent was removed under reduced pressure and the residue chromatographed on silica gel, eluting with EtOAc/petroleum ether (35/65). There was obtained 0.56 g of the product as an oil. The structure was confirmed by NMR and mass spectroscopy.

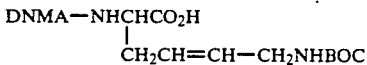

A solution of 0.56 g of

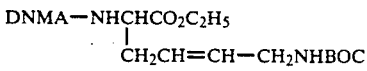

in 10 ml MeOH was treated with a solution of 0.1 g NaOH in 2 ml $H_2O$ and stirred at room temperature for 4 hours. The solution was diluted with $H_2O$ and washed with $Et_2O$. The aqueous layer was brought to pH 2 with dil. HCl, and then extracted with EtOAc. The EtOAc was washed with saturated NaCl, dried, and the solvent removed under reduced pressure leaving 0.5 g of the product as a white foam. The structure was confirmed by NMR and mass spectroscopy. The NMR showed this to be a single double bond isomer, the E-isomer.

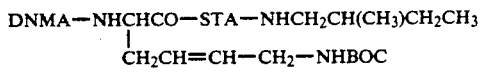

A solution of 1.48 g (2.61 mmole) of

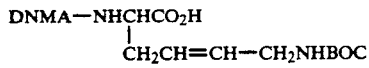

and 0.35 g (2.61 mmole) of HOBT in 60 ml CH$_2$Cl$_2$ and 5 ml of DMF was cooled in ice and a solution of 0.539 g (2.61 mmole) of DCC in 10 ml CH$_2$Cl$_2$ added. A solution of 0.639 g (2.61 mmole) of STA-NHCH$_2$CH(CH$_3$)CH$_2$CH$_3$ in 10 ml CH$_2$Cl$_2$ was then added and the solution stirred for 1 hour at 0°, then at room temperature for 16 hours. The mixture was then filtered and the filtrate evaporated. The residue was taken up in EtOAc and washed with H$_2$O and brine. Drying and removal of the solvent under reduced pressure left an oil. This was chromatographed on silica gel, eluting with CHCl$_3$/MeOH (95/5). There was obtained 1.72 g of the product as a white foam. The structure was confirmed by NMR and mass spectroscopy.

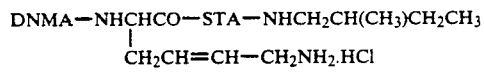

A solution of 1.7 g (2.15 mmole) of

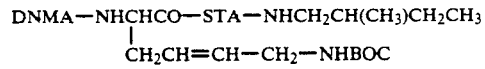

in 50 ml CH$_2$Cl$_2$ was purged with HCl for 30 minutes. The solvent was removed under reduced pressure, CHCl$_3$ added and the solvent removed again. This process was then repeated. There was obtained 1.54 g of the product as a white foam. The structure was confirmed by NMR and mass spectroscopy.

INTERMEDIATES FOR EXAMPLE 84

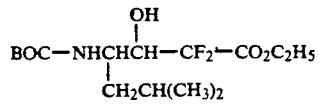

Activated Zn dust (325 mesh) was suspended in benzene and dried by distilling off the benzene. Under argon, a suspension of 0.35 g (5.35 mmole) of the Zn dust in 15 ml dioxane was treated with a crystal of I$_2$ and 0.1 ml (0.78 mmole) of ethyl bromodifluoroacetate. The mixture was subjected to ultrasonic conditions for 10 minutes. A solution of 0.55 ml (4.28 mmole) of ethyl bromodifluoroacetate and 0.49 g (1.92 mmole) BOC-LEUCINAL in 10 ml dioxane was then added over a 30 minute period and the mixture subjected to ultrasonic conditions for 45 minutes. The mixture was poured into CH$_2$Cl$_2$ and washed with 1M NaHSO$_3$. Drying and removal of the solvent under reduced pressure gave the crude product which was chromatographed on silica gel, eluting with a gradient of 10-20% EtOAc in hexane. There was obtained 0.5 g of the product. The structure was confirmed by NMR and mass spectroscopy.

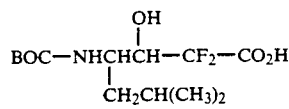

A solution of 5.2 g (15 mmole) of

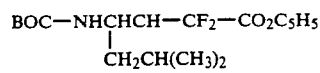

in 30 ml THF was treated with a solution of 0.62 g (15.5 mmole) of NaOH in 15 ml H$_2$O and stirred for 4 hours. The pH was then brought to 2.0 and the solution extracted three times with EtOAc. The combined EtOAc extract was washed with H$_2$O, then brine. Drying and removal of the solvent under reduced pressure left the product as a white foam. The structure was confirmed by NMR and mass spectroscopy.

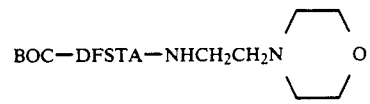

A solution of 4.23 g (13.6 mmole) of

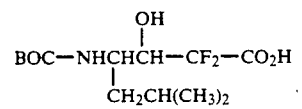

and 1.84 g (13.6 mmole) of HOBT in 50 ml DMF was cooled to 0° and a solution of 2.81 g (13.6 mmole) of DCC in 10 ml DMF added, followed by 1.77 g (13.6 mmole) of 4-(2-aminoethyl)morpholine. The mixture was stirred at 0° for 1 hour, then at room temperature for 16 hours. The mixture was filtered and the filtrate evaporated under high vacuum. The residue was taken up in EtOAc and washed with 1N NaOH, then brine. Drying and removal of the solvent under reduced pressure gave the crude product which was chromatographed on silica gel, eluting with a gradient of 5-7% MeOH in CHCl$_3$. There was obtained 3.87 g of the product as a white solid. The structure was confirmed by NMR and mass spectroscopy.

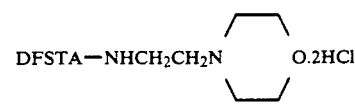

A solution of 3.3 g (7.8 mmole) of

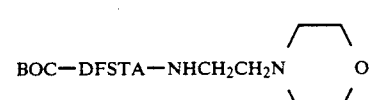

in 100 ml CHCl$_3$ and 5 ml MeOH was treated with HCl gas for 30 minutes. The solvent was removed under reduced pressure, the residue taken up in CHCl$_3$ and the solvent removed again. The process was repeated to give 3.05 g of the product as a white foam. The structure was confirmed by NMR and mass spectroscopy.

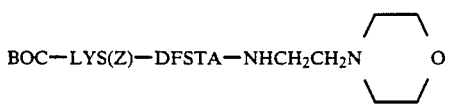

A solution of 3.09 g (7.8 mmole) of

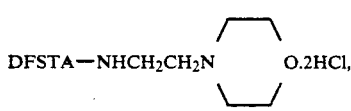

2.96 g (7.8 mmole) of BOC-LYS(Z), and 1.05 g (7.8 mmole) of HOBT in 100 ml DMF was treated with 2.17 ml (15.6 mmole) of Et₃N and cooled in ice. A solution of 1.61 g (7.8 mmole) of DCC in 10 ml DMF was then added and the mixture stirred at 0° for 1 hour, then at room temperature for 16 hours. The mixture was filtered and the filtrate evaporated under high vacuum. The residue was taken up in EtOAc and washed with 1N NaOH, then brine. Drying and removal of the solvent under reduced pressure left the crude product which was chromatographed on silica gel, eluting with a gradient of 2–5% MeOH in CHCl₃. There was obtained 3.82 g of product as a white foam. The structure was confirmed by NMR and mass spectroscopy.

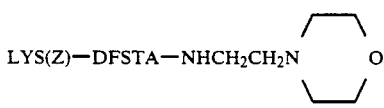

A solution of 3.8 g (5.58 mmole) of

in 40 ml CH₂Cl₂ was treated with 5.0 ml of TFA and the solution stirred at room temperature for 14 hours. The solvent was removed under reduced pressure and the residue taken up in EtOAc. The EtOAc was washed with a small amount of saturated NaHCO₃ and saturated NaCl. The aqueous washes were then extracted with EtOAc. The combined EtOAc washes were dried and the solvent removed under reduced pressure to give 3.0 g of the product as a white foam. The structure was confirmed by NMR and mass spectroscopy.

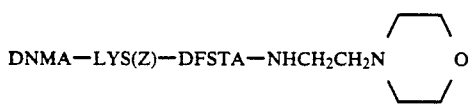

A solution of 1.5 g (2.56 mmole) of

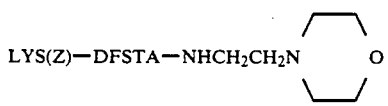

and 0.92 g (2.56 mmole) of DNMA-Cl in 100 ml CHCl₃ was cooled in ice and treated with 0.4 ml (2.86 mmole) of Et₃N. After stirring at room temperature for 24 hours, the solvent was removed and the residue chromatographed on silica gel, eluting with CHCl₃/MeOH (95/5). There was obtained 1.18 g of product. The structure was confirmed by NMR and mass spectroscopy.

Calcd. for $C_{52}H_{63}N_5O_7F_2 \cdot 0.14$ CHCl₃ (MW 924.81): C, 67.72; H, 6.81; N, 7.57; F, 4.10; Cl, 1.81. Found C, 67.42; H, 6.94; N, 7.63; F, 4.68; Cl, 1.83.

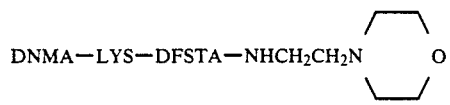

A solution of 1.18 g (1.3 mmole) of

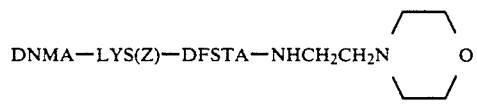

in 50 ml MeOH was treated with 50 mg of 20% Pd/C and stirred under a hydrogen atmosphere for 3 hours. The mixture was filtered and the filtrate evaporated under reduced pressure to give 1.3 g of the product as a white foam. The material was used directly in the following step.

INTERMEDIATE FOR EXAMPLE 85

2-BENZYL-3-(1-NAPHTHYL)PROPIONYL CHLORIDE

A solution of 5.0 g (17.2 mmole) of 2-benzyl-3-(1-naphthyl)propionic acid (EP-186,977) in 30 ml SOCl₂ was stirred overnight at room temperature. The mixture was stripped to 5.48 g of an oil which was used without further purification in the following reaction.

MNPP-LYS(Z)-OCH₃

2-(1-Naphthylmethyl)-3-phenylpropionyl chloride (5.2 g, 16.8 mmole) was dissolved in 100 ml CH₂Cl₂ and cooled to 0°. LYS(Z)OCH₃·HCl (5.57 g, 16.8 mmole) was added, followed by Et₃N (3.74 g, 37 mmole). After stirring at 23° overnight the mixture was evaporated to a gum and dissolved in EtOAc. The solution was washed with 1N citric acid, saturated NaCl, saturated NaHCO₃ and saturated NaCl. The solution was dried over MgSO₄ and evaporated in vacuo to a gum, 9.66 g. The structure was confirmed by NMR and mass spectroscopy.

MNPP-LYS(Z)

MNPP-LYS(Z)-OCH₃ (9.6 g, 16.94 mmole) was dissolved in 50 ml MeOH and 28 ml 1N NaOH was added. After 1.5 hours, 15 ml 1N HCl was added, and the MeOH was removed in vacuo. The residue was cooled to 5° and 13 ml 1N HCl was added. The mixture was extracted into Et₂O, washed with saturated NaCl, dried over MgSO₄ and evaporated in vacuo to a foam, 8.89 g. The structure was confirmed by NMR and mass spectroscopy.

MNPP-LYS(Z)-STA-NHCH₂CH(CH₃)CH₂CH₃

MNPP-LYS(Z) (8.87 g, 16.1 mmole) and HOBT (2.24 g, 16.6 mmole) were dissolved in 100 ml DMF and cooled to 0°. A solution of STA-NHCH₂CH(CH₃)CH₂CH₃ (3.93 g, 16.1 mmole) in 30 ml DMF was added followed by DCC (3.42 g, 16.6 mmole). The mixture was stirred at 0° for 3 hours then at 23° overnight. The mixture was filtered and the DMF was removed under high vacuum. The residue was suspended in a mixture of EtOAc and CH₂Cl₂, which was washed with 1N citric acid, saturated NaCl, saturated NaHCO₃, and saturated NaCl. After drying over MgSO₄, the product was precipitated by addition of ET₂O. The resulting solid was filtered, washed with ET₂O and dried to a white solid, 8.38 g. The structure was confirmed by NMR and mass spectroscopy.

MNPP-LYS-STA-NHCH₂CH(CH₃)CH₂CH₃

MNPP-LYS(Z)-STA-NHCH₂CH(CH₃)CH₂CH₃ (7.70 g, 9.88 mmole) was dissolved in 100 ml MeOH. 0.5 g 20% Pd/C catalyst was added, followed by hydrogen gas purging over 3 hours. The mixture was filtered and evaporated in vacuo to a white foam, 5.44 g. The structure was confirmed by NMR and mass spectroscopy.

INTERMEDIATES FOR EXAMPLE 87

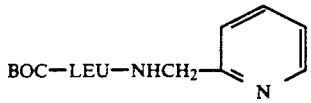

A solution of 15.52 g (62.2 mmole) BOC-LEU.H₂O in 200 ml THF/CH₂Cl₂ (50/50) was dried over anhydrous MgSO₄, filtered, and evaporated to an oil. The oil was dissolved in 200 ml DMF, to which was added 8.82 g (65.4 mmole) HOBT. After cooling to −5°, a solution of 13.48 g (65 mmole) DCC in 30 ml DMF was added, followed by 6.8 ml (62.2 mmole) of 2-aminomethylpyridine. The mixture was stirred and allowed to warm to room temperature overnight. The mixture was filtered, and the solvent was removed under high vacuum. The residue was taken into EtOAc and washed with 1N citric acid, saturated NaCl, saturated NaHCO₃, and saturated NaCl. After drying, the solvent was removed under reduced pressure, and the residue was chromatographed on silica gel, eluting with a gradient of 0–5% MeOH in CHCl₃. There was obtained 16.8 g of a solid of sufficient purity for use in the following reaction. The structure was confirmed by NMR and mass spectroscopy.

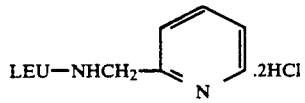

A solution of 6.41 g (19.9 mmole) of

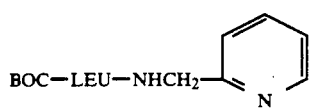

in 80 ml CH₂Cl₂ was occasionally purged with HCl gas over 3 hours, then evaporated under reduced pressure leaving a solid. The solid was triturated with ET₂O, filtered, washed with ET₂O, and dried giving 5.85 g of a white solid of sufficient purity for use in the following reaction. The structure was confirmed by NMR and mass spectroscopy.

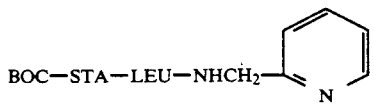

A solution of 1.84 g (6.05 mmole) BOC-STA and 0.86 g (6.35 mmole) HOBT in 20 ml DMF was cooled to −5°. A solution of 1.78 g (6.05 mmole)

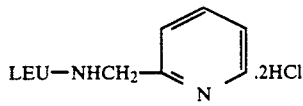

in 20 ml DMF and 1.8 ml (12.9 mmole) Et₃N was cooled to 0° and added to the previously described solution. To the combined solutions was added 1.31 g (6.35 mmole) DCC, and the solution stirred and allowed to warm to room temperature overnight. The mixture was filtered and the solvent removed under high vacuum. The residue was taken up in EtOAc and washed with 1N citric acid, saturated NaCl, saturated NaHCO₃, and saturated NaCl. After drying the solution was evaporated and the residue was chromatographed on silica gel, eluting with a gradient of 0–10% MeOH in CHCl₃. There was obtained 2.89 g of the product as a foam, of sufficient purity for use in the following reaction. The structure was confirmed by mass spectroscopy.

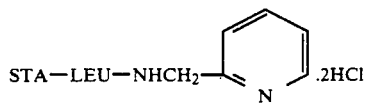

A solution of 2.2 g (4.46 mmole) of

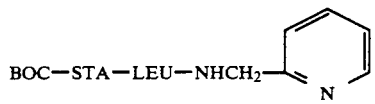

in 150 ml CH₂Cl₂ was occasionally purged with HCl gas over 3 hours. The solution was evaporated under reduced pressure and the residue was triturated with ET₂O. The solids were filtered, washed with ET₂O, and dried to give 2.05 g of a white solid, of sufficient purity for use in the following reaction. The structure was confirmed by NMR and mass spectroscopy.

COMMKIN INTERMEDIATES

BOC-STA-LEU-NHCH₂Ph 1.80 g LEU-NHCH₂Ph.HCl [Japan 83/59952], 2.27 g BOC-STA (U.S. Pat. No. 4,397,786) and 1.04 g 1-hydroxybenzotriazole-hydrate were dissolved in 125 ml dichloromethane and cooled to 0°. 1.07 ml of Et₃N was then added. A cold solution of 1.59 g dicyclohexylcarbodiimide in 20 ml dichloromethane was added, followed by the addition of 50 ml cold dimethylformamide. The mixture was stirred at 0° for two hours, followed by 12° overnight. The mixture was then filtered, stripped to a paste, and resuspended in ethyl acetate. The suspension was filtered, the filtrate washed with 1N citric acid, saturated sodium chloride solution, saturated sodium bicarbonate solution, saturated sodium chloride solution, and dried over anhydrous magnesium sulfate. The suspension was filtered and stripped to a white foam 3.77 g, which was crystallized from ethyl ether and hexane giving a white solid, 3.41 g (92% yield), mp 89°-92°. Spectral and elemental analysis confirmed the structure. $[\alpha]_D^{23} = -34.2°$ (C, 1.06, MeOH).

STA-LEU-NHCH$_2$Ph.HCl 2.77 g BOC-STA-LEU-NHCH$_2$Ph was dissolved in 100 ml dichloromethane, which was then saturated with anhydrous hydrogen chloride gas. After stirring at 25° for one hour, the solvent was removed in vacuo, and the residue resuspended in dichloromethane, giving a crystalline solid. The suspension was diluted with ethyl ether, filtered, and the solid dried in vacuo, 2.24 g, 93% yield. Spectral and elemental analyses confirmed the structure. $[\alpha]_D^{23} = -19.1°$ (C, 1.06, MeOH).

BOC-STA-NHCH$_2$CH(CH$_3$)CH$_2$CH$_3$

BOC-STA (27.53 g, 0.1 mole, U.S. Pat. No. 4,397,786) and HOBT.H$_2$O (14.2 g, 0.105 mole) were dissolved in 40 ml DMF. 300 ml CH$_2$Cl$_2$ was added, and the mixture was cooled to 0°. A solution of DCC (21.66 g, 0.105 mole) in 50 ml CH$_2$Cl$_2$ was added, followed by S-2-methylbutylamine (12 ml, 0.1 mole). After stirring at 0° for two hours, the mixture was allowed to warm to 25° over 1.5 hours. The mixture was filtered, and the solvent was removed in vacuo. The residue was dissolved in EtOAc, which was washed with 1N citric acid, brine, saturated NaHCO$_3$ solution, and brine. The organic phase was dried over MgSO$_4$, filtered, and stripped to a gum, 36.90 g. The gum was dissolved in ET$_2$O and treated with charcoal to remove colored impurities. The suspension was filtered and stripped to a gum, 35.2 g, which was suitable for use in the following procedure without further purification.

STA-NHCH$_2$CH(CH$_3$)CH$_2$CH$_3$.HCl

BOC-STA-NHCH$_2$CH(CH$_3$)CH$_2$CH$_3$ (34.4 g, 0.1 mole) was dissolved in 250 ml CH$_2$Cl$_2$, and the solution was purged occasionally with anhydrous HCl gas over three hours. A solid precipitated from solution which was filtered, washed with CH$_2$Cl$_2$, and dried at 40° in vacuo to a hygroscopic solid, 21 g. The solid was triturated with a mixture of CH$_2$Cl$_2$/ET$_2$O, filtered, and dried at 40° in vacuo to a white solid, 19.34 g. Spectral analysis confirmed the structure.

STA-NHCH$_2$CH(CH$_3$)CH$_2$CH$_3$

A solution of 38.0 g (0.11 mole) of BOC-STA-NHCH$_2$CH(CH$_3$)CH$_2$CH$_3$ in 250 ml CH$_2$Cl$_2$ was treated with HCl gas every one-half hour over a three hour period. The solvent was removed under reduced pressure and the residue taken up in 30 ml H$_2$O and 110 ml of 1N HCl. The solution was washed twice with ET$_2$O, the pH brought to 13 with 2N NaOH, and the solution extracted twice with ET$_2$O. The ET$_2$O was washed with saturated NaCl, dried, and the solvent removed under reduced pressure giving 22.3 g of the product as an oil which solidified on standing. The material was sufficiently pure for use in subsequent reactions.

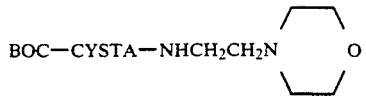

A solution of 17.7 g (0.056 mole) of BOC-STA and 7.59 g (0.056 mole) of HOBT in 250 ml of DMF was cooled in ice and treated with a solution of 11.7 g (0.056 mole) of DCC in 20 ml of DMF. After stirring for 5 minutes, the solution was treated with 7.6 ml (0.056 mole) of 4-(2-aminoethyl)morpholine. The solution was stirred for 0.5 hours at 0°, then at room temperature overnight. The dicyclohexylurea was filtered off and the solvent removed under high vacuum. The residue was taken up in EtOAc, washed with saturated NaHCO$_3$, H$_2$O, then saturated NaCl, and then dried over MgSO$_4$. Removal of the solvent under reduced pressure gave the crude product which was purified by chromatography on silica gel, eluting with CHCl$_3$/MeOH (95/5). There was obtained 24 g of pure product.

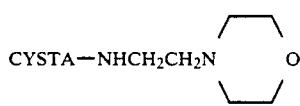

A solution of 24 g (0.056 mole) of

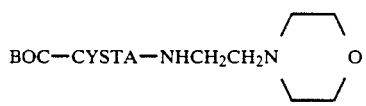

in 300 ml of CH$_2$Cl$_2$ was treated with HCl gas for 5 minutes. A gum formed which was redissolved by the addition of 100 ml of MeOH. HCl gas was bubbled in for an additional 10 minutes, and the solution allowed to stir at room temperature for 3 hours. The solvent was removed under reduced pressure and the residue taken up in CH$_2$Cl$_2$. This was treated with CH$_2$Cl$_2$ that had been saturated with NH$_3$ gas at 0°. The NH$_4$Cl was filtered off and the filtrated evaporated. There was obtained 15.2 g of an oil which solidified on standing. The structure was confirmed by NMR spectroscopy.

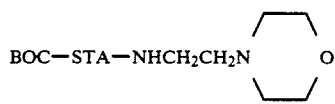

A solution of 27.53 g (0.1 mole) of BOC-STA and 13.52 g (0.1 mole) of HOBT in 200 ml DMF was cooled in ice and treated in portions with a solution of 20.9 g (0.1 mole) of DCC in 50 ml DMF, then with 13.0 g (0.1 mole) of 4-(2-aminoethyl)morpholine. The mixture was kept at 0° for 1 hour, then at room temperature for 16 hours. The mixture was then filtered and the filtrate evaporated under high vacuum. The residue was taken up in EtOAc and washed with saturated NaHCO$_3$, then saturated NaCl. Drying and removal of the solvent under reduced pressure gave the crude product which was chromatographed on silica gel, eluting with CHCl$_3$/MeOH (94/6). There was obtained 29.6 g of the product. The structure was confirmed by NMR and mass spectroscopy.

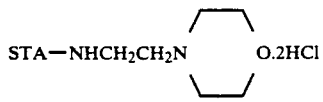

A solution of 6.1 g (16.0 mmole) of

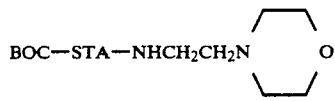

in 150 ml CH₂CH₂ and 20 ml MeOH was treated with HCl gas for 20 minutes. The solvent was then removed under reduced pressure, the residue taken up in CHCl₃, and the solvent again evaporated. This process was repeated several times to give 5.6 g of the product as a white foam. The structure was confirmed by NMR spectroscopy.

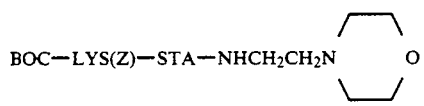

A solution of 5.7 g (16 mmole) of

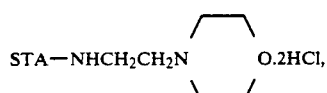

6.08 g (16 mmole) of BOC-LYS(Z) and 2.16 g (16 mmole) of HOBT in 10 ml DMF was treated with 4.39 ml (32 mmole) of Et₃N and then cooled to −10°. A solution of 3.3 g (16 mmole) of DCC in 20 ml DMF was then added slowly. After stirring at −10° for 1 hour, the mixture was left at room temperature for 16 hours. The mixture was filtered and the filtrate evaporated under high vacuum. The residue was taken up in EtOAc and washed with saturated NaHCO₃, then brine. After drying and removal of the solvent under reduced pressure, the residue was chromatographed on silica gel, eluting with CHCl₃/MeOH (92/8). There was obtained 5.25 g of product. The structure was confirmed by NMR and mass spectroscopy.

Calcd. for C₃₃H₅₅N₅O₈ (MW 649.84): C, 60.99; H, 8.53; N, 10.78 Found C, 60.89; H, 8.68; N, 10.84.

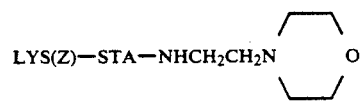

A solution of 7.15 g (11 mmole) of

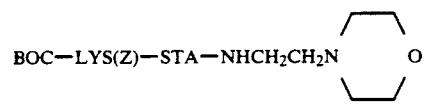

in 200 ml CH₂Cl₂ was treated with 20 ml of TFA and stirred for 5 hours at room temperature. The solvent was removed under reduced pressure and the residue taken up in EtOAc and washed with a small quantity of saturated NaHCO₃, then a small quantity of brine. Drying and removal of the solvent under reduced pressure gave 6.05 g of the product as a white foam. The structure was confirmed by NMR spectroscopy.

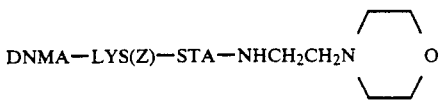

A solution of 1.5 g (2.73 mmole) of

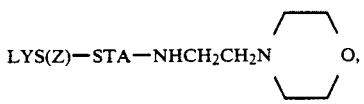

0.93 g (2.73 mmole) of di-(1-naphthylmethyl)acetic acid, and 0.37 g (2.73 mmole) of HOBT in 20 ml DMF was cooled to 0° and 0.56 g (2.73 mmole) of DCC added. The mixture was kept at 0° for 1 hour, then at room temperature for 16 hours. The mixture was then filtered and the filtrate evaporated under high vacuum. The residue was taken up in EtOAc and washed with saturated NaHCO₃, H₂O, saturated NaHCO₃, and brine. Drying and removal of the solvent under reduced pressure gave a yellow solid. Chromatography on silica gel, eluting with a gradient of 5-8% MeOH in CHCl₃, gave 1.42 g of the product as a white foam. The structure was confirmed by NMR and mass spectroscopy.

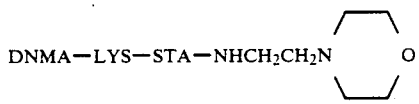

A solution of 0.46 g (0.53 mmole) of

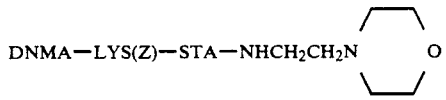

in 25 ml MeOH was treated with 50 mg of 20% Pd/C and stirred under hydrogen for 8 hours. The mixture was filtered and the filtrate evaporated under reduced pressure to give 0.39 g of the product as a white foam. The material was used without further purification in the next step.

We claim:

1. A peptide of the formula

or a pharmaceutically acceptable acid addition salt thereof, wherein

ACYL is BOC, IVA, NVA, DNMA, Z, MNPP, BMA, BBSP, or

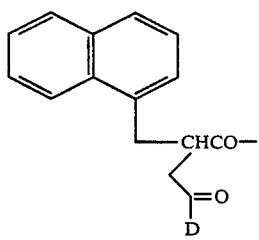
wherein D is
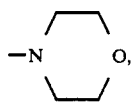
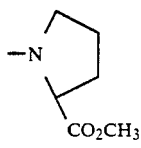
—NCH₂CO₂CH₃,
 |
 CH₃
—OCH₃,
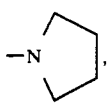
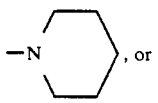, or
—N(CH₃)₂;
X is absent, PHE, HOMOPHE, NAPHTHYLALA, CYCLOHEXYLALA, O-MeTYR, TYR, or TRP, with the proviso that when ACYL is DNMA, BBSP, MNPP, or
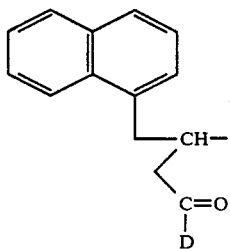 wherein D is as above,
X is absent;
Y is
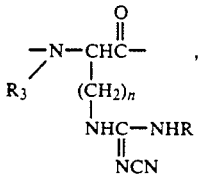
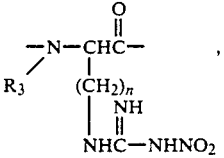
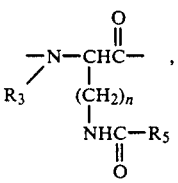
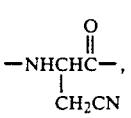
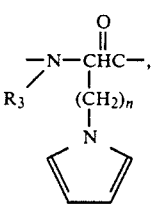
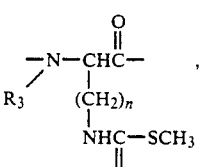
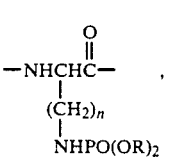
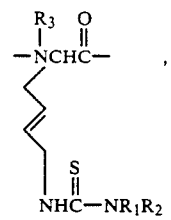
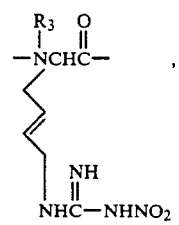
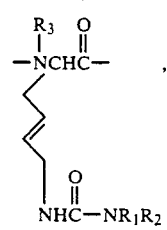

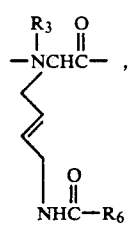
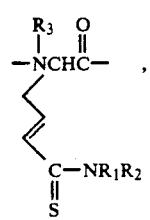
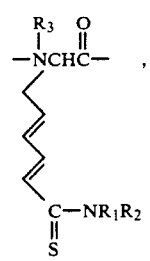
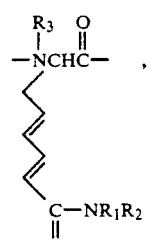
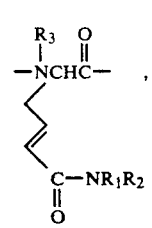
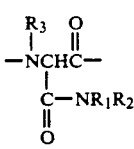
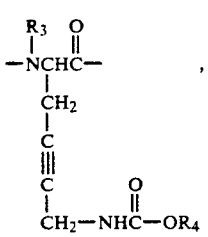
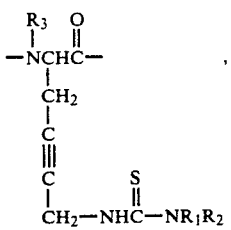
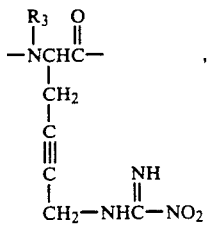
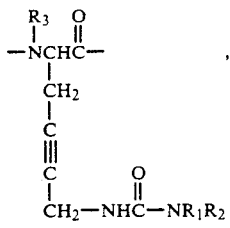
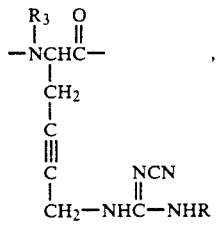
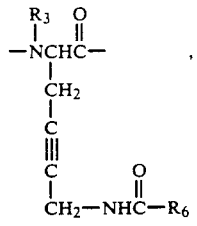
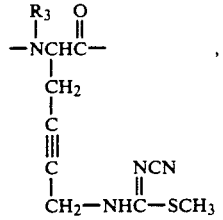
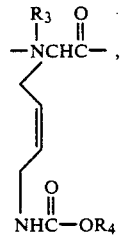

-continued

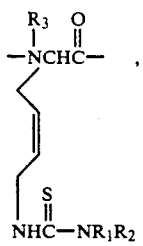

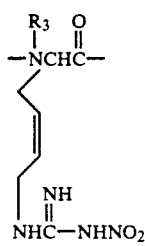

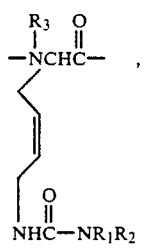

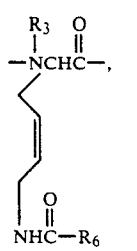

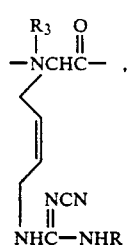

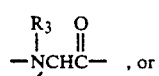

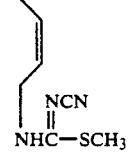

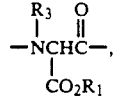

wherein n is an integer from 2 to 8, R is hydrogen or an alkyl of from 1 to 3 carbon atoms,
$R_1$ and $R_2$ are each independently hydrogen, lower alkyl of from 1 to 4 carbon atoms, or taken together form a 5 or 6 membered ring with the nitrogen to which they are attached, aralkyl, or aryl, $R_3$ is hydrogen or methyl,
$R_4$ is lower alkyl or benzyl,
$R_5$ is $CH_2SCH_3$, $CH_2SOCH_3$, or $CH_2SO_2CH_3$,
$R_6$ is $R_5$, H, or lower alkyl;
W is STA, PHSTA, CYSTA, ASTA, ACYS, CHSTA, DFSTA, DFKSTA, DFCYS, DFKCYS, DFCHS, or DFKCHS;
U is absent, LEU, ILE, VAL, N-MeLEU, N-MeILE; and
V is —NHCH$_2$Ph, —NHCH$_2$—⬡,

—NHCH$_2$—⌬—CH$_2$NHZ(BOC),

—NHCH$_2$—⌬—CH$_2$NH$_2$, —NH—⬡N—CH$_2$Ph,

—NH—⬡NH, —NHCH$_2$—⬠(N),

—NHCH$_2$CH(CH$_3$)CH$_2$CH$_3$, —OCH$_3$, —OC$_2$H$_5$,

—NHCHCH(CH$_3$)CH$_2$CH$_3$, or —NHCH$_2$CH$_2$N⬡O.
     |
     CH$_2$OH

2. A compound according to claim 1 wherein ACYL is BOC, IVA, DNMA, BMA, BBSP or

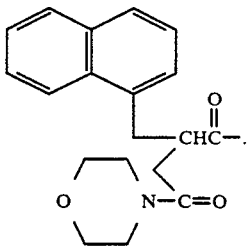

3. A compound according to claim 1 wherein V is

—NHCH$_2$Ph, —NHCH$_2$—⬠(N),

—NHCH$_2$—⌬—CH$_2$NH$_2$, —NHCH$_2$CH(CH$_3$)CH$_2$CH$_3$,

-continued

—NHCHCH(CH₃)CH₂CH₃, or —NHCH₂CH₂N⟨O⟩.
   |
   CH₂OH

4. A peptide selected from the group consisting of

BOC—PHE—ARG(NO₂)—STA—LEU—NHCH₂Ph,

DNMA—LYS(C(=NH)—NHNO₂)—CYSTA—NHCH₂CH(CH₃)CH₂CH₃,

DNMA—LYS(C(=NCN)—SCH₃)—STA—NHCH₂CH(CH₃)CH₂CH₃,

DNMA—LYS(C(=NCN)—NH₂)—STA—NHCH₂CH(CH₃)CH₂CH₃,

DNMA—LYS(C(=NCN)—NHCH₃)—STA—NHCH₂CH(CH₃)CH₂CH₃,

DNMA—NHCHCO—STA—NHCH₂CH(CH₃)CH₂CH₃,     DNMA—LYS(C(=O)—NHCH₃)—STA—LEU—NHCH₂Ph,
         |
         (CH₂)₄—N(pyrrole)

DNMA—NHCHCO—STA—NHCH₂CH(CH₃)CH₂CH₃,     DNMA—NHCHCO—STA—NHCH₂CH(CH₃)CH₂CH₃,
         |                                              |
         (CH₂)₅—NHC(=NH)—NHNO₂                          (CH₂)₆—NHC(=NCN)—NH₂

DNMA—NHCHCO—STA—NHCH₂CH(CH₃)CH₂CH₃,     DNMA—NHCHCO—STA—NHCH₂CH(CH₃)CH₂CH₃,
         |                                              |
         CH₂C≡C—CH₂—NHZ                                 CO₂CH₃

BOC—PHE—NHCHCO—STA—NHCH₂CH(CH₃)CH₂CH₃,
         |
         CO₂CH₃

DNMA—NHCHCO—STA—NHCH₂CH(CH₃)CH₂CH₃,
         |
         CON(CH₃)₂

DNMA—NHCHCO—STA—NHCH₂CH(CH₃)CH₂CH₃,
         |
         CO₂C₂H₅

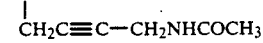

(Naphthyl)CH₂—CHCO—NHCHCO—STA—NHCH₂CH(CH₃)CH₂CH₃,
              |           |
              CH₂—N(morpholino)—C=O    CO₂CH₃

DNMA—NHCHCO—STA—NHCH₂CH(CH₃)CH₂CH₃,
         |
         CO₂CH(CH₃)₂

DNMA—NHCHCO—STA—NHCH₂CH(CH₃)CH₂CH₃ (Isomer A),
         |
         CH₂C≡C—CH₂NHCOCH₃

DNMA—NHCHCO—STA—NHCH₂CH(CH₃)CH₂CH₃ (Isomer B),
         |
         CH₂C≡C—CH₂NHCOCH₃

-continued

DNMA—NHCHCO—STA—NHCH₂CH(CH₃)CH₂CH₃,
       |
       CH₂CH=CHCH₂NHCOCH₃
              (Z)

DNMA—NHCHCO—CYSTA—NHCH₂CH₂N⟨O⟩,   DNMA—NHCHCO—CYSTA—NHCH₂CH₂N⟨O⟩,
       |                                   |
       CH₂C≡C—CH₂NHC—H                     CH₂C≡C—CH₂NHCOCH₃
                 ‖
                 O

DNMA—NHCHCO—CYSTA—NHCH₂CH₂N⟨O⟩,   DNMA—NHCHCO—CYSTA—NHCH₂CH₂N⟨O⟩,
       |                                   |
       CH₂C≡C—CH₂NHC—NHNO₂                 CH₂C≡C—CH₂NHC—NHCH₃
                 ‖                                   ‖
                 NH                                  S

O
            ‖
DNMA—LYS(CCH₂SCH₃)—STA—NHCH₂CH(CH₃)CH₂CH₃,

O
            ‖
DNMA—LYS(CCH₂SO₂CH₃)—STA—NHCH₂CH(CH₃)CH₂CH₃,

O
            ‖
DNMA—LYS(CCH₂SOCH₃)—STA—NHCH₂CH(CH₃)CH₂CH₃,

DNMA—NHCHCO—CHSTA—NHCH₂CH(CH₃)CH₂CH₃,
       |
       CO₂CH₃

DNMA—NHCHCO—CHSTA—NHCH₂CH₂N⟨O⟩,   DNMA—NHCHCO—STA—NHCH₂CH(CH₃)CH₂CH₃,
       |                                   |
       CO₂CH₃                              CH₂CN

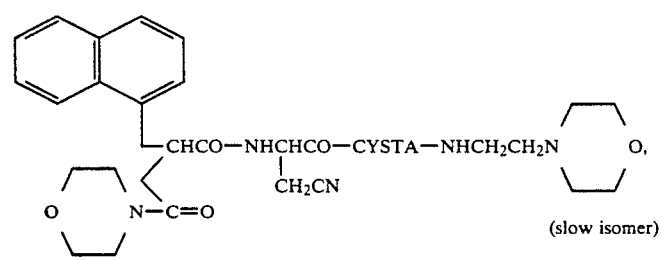
(slow isomer)

NH
         ‖
DNMA—LYS(CNHNO₂)—STA—NHCH₂CH₂N⟨O⟩,

NCN
         ‖
DNMA—LYS(CSCH₃)—STA—NHCH₂CH₂N⟨O⟩,   DNMA—NHCHCO—STA—NHCH₂CH(CH₃)CH₂CH₃,
                                           |
                                           CH₂CH=CHCH₂NHCNHCH₃
                                               (E)        ‖
                                                          S

BOC—PHE—NHCHCO—STA—NHCH₂CH(CH₃)CH₂CH₃, and
         |
         O=C—N⟩

-continued
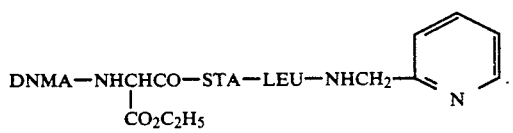
5. A pharmaceutical composition comprising a renin-inhibitory effective amount of a compound as claimed in claim 4 together with a pharmaceutically acceptable carrier.
6. A method of treating renin-associated hypertension which comprises administering to a mammal a pharmaceutical composition as claimed in claim 5.
* * * * *